United States Patent
Madsen, II et al.

(10) Patent No.: US 11,578,091 B2
(45) Date of Patent: Feb. 14, 2023

(54) PROCESS FOR THE MANUFACTURE OF MALTOSYL-ISOMALTOOLIGOSACCHARIDES (MIMO)

(71) Applicant: ISOThrive LLC, Healdsburg, CA (US)

(72) Inventors: Lee Madsen, II, Manassas, VA (US); Jack Oswald, Healdsburg, CA (US)

(73) Assignee: ISOThrive LLC, Healdsburg, CA (US)

(*) Notice: Subject to any disclaimer, the term of this patent is extended or adjusted under 35 U.S.C. 154(b) by 1 day.

(21) Appl. No.: 16/769,953

(22) PCT Filed: Dec. 7, 2018

(86) PCT No.: PCT/US2018/064480
§ 371 (c)(1),
(2) Date: Jun. 4, 2020

(87) PCT Pub. No.: WO2019/113446
PCT Pub. Date: Jun. 13, 2019

(65) Prior Publication Data
US 2020/0392175 A1    Dec. 17, 2020

Related U.S. Application Data

(60) Provisional application No. 62/596,186, filed on Dec. 8, 2017.

(51) Int. Cl.
| | |
|---|---|
| *C07H 3/06* | (2006.01) |
| *C07H 1/06* | (2006.01) |
| *C12M 1/00* | (2006.01) |
| *C12P 19/04* | (2006.01) |
| *C12P 19/18* | (2006.01) |

(52) U.S. Cl.
CPC .......... *C07H 3/06* (2013.01); *C07H 1/06* (2013.01); *C12M 47/12* (2013.01); *C12P 19/04* (2013.01); *C12P 19/18* (2013.01)

(58) Field of Classification Search
CPC . C07H 3/06; C07H 1/06; C12M 47/12; C12P 19/04; C12P 19/18

USPC .................................................. 536/127
See application file for complete search history.

(56) References Cited

U.S. PATENT DOCUMENTS

| | | | |
|---|---|---|---|
| 2004/0235789 A1 | 11/2004 | Day et al. | |
| 2009/0014386 A1* | 1/2009 | Manttari ............... | C13K 13/00 210/639 |
| 2010/0284972 A1 | 11/2010 | Naeye | |
| 2017/0202869 A1 | 7/2017 | Madsen, II et al. | |
| 2017/0275651 A1 | 9/2017 | Keasling et al. | |
| 2017/0275661 A1 | 9/2017 | Madsen, II et al. | |

FOREIGN PATENT DOCUMENTS

| | | | |
|---|---|---|---|
| WO | WO 2016/029198 | * | 2/2016 |
| WO | WO-2017180626 A1 | | 10/2017 |
| WO | WO-2019113446 A1 | | 6/2019 |

OTHER PUBLICATIONS

"International Application Serial No. PCT US2018 064480, International Preliminary Report on Patentability dated Jun. 18, 2020", 8 pgs.

"International Application Serial No. PCT/US2018/064480, International Search Report dated Mar. 25, 2019", 3 pgs.

"International Application Serial No. PCT/US2018/064480, Written Opinion dated Mar. 25, 2019", 6 pgs.

"European Application Serial No. 18885529.0, Extended European Search Report dated Aug. 10, 2021", 12 pgs.

"European Application Serial No. 18885529.0, Response filed Jan. 15, 2021 to Communication pursuant to Rules 161(2) and 162 EPC", 14 pgs.

"European Application Serial No. 18885529.0, Response filed Feb. 28, 2022 to Extended European Search Report dated Aug. 10, 2021", 21 pgs.

* cited by examiner

*Primary Examiner* — Yih-Horng Shiao
(74) *Attorney, Agent, or Firm* — Schwegman Lundberg & Woessner, P.A.

(57) ABSTRACT

Methods and systems are described herein for manufacturing oligosaccharides, including maltosyl-isomaltooligosaccharides. The methods involve removing undesired components from fermentation fluids that contain maltosyl-isomaltooligosaccharides.

23 Claims, 22 Drawing Sheets

PROCESS FOR THE MANUFACTURE OF MALTOSYL-ISOMALTOOLIGOSACCHARIDES (MIMO)

This application is a U.S. National Stage Application under 35 U.S.C. 371 from International Application Serial No. PCT/US2018/064480, filed on Dec. 7, 2018, and published as WO 2019/113446 A1 on Jun. 13, 2019, which claims the benefit of priority to the filing date of U.S. Provisional Application Ser. No. 62/596,186 filed Dec. 8, 2017, the contents of which are specifically incorporated herein by reference in their entirety.

BACKGROUND

Probiotics are made up of living cultures of bacteria, such as those in yogurt, that promote the growth of healthy gut flora by means of population support (Gilliland, S. E. et al., "Health and Nutritional Properties of Probiotics in Food including Powder Milk with Live Lactic Acid Bacteria", 2001, p. 1-34, World Health Organization). Prebiotics, however, are materials, either physical (e.g. dietary fiber) or chemical (e.g. butyrate) which can promote the growth of selected beneficial flora (Chung, C. H., et al., Poult. Sci., 2004, 83:1302-6) and/or exert some beneficial effect directly on intestinal epithelial cells (thus improving uptake of nutritive calories, vitamins, minerals, etc.). Because many prebiotics can overcome the resistance of the digestive barrier facilitating the proliferation and/or activity of desired populations of bacteria in situ (Gibson G. R. et al., J. Nutr., 1995, 125:1401-12; Van Loo, J. et al., Br. J. Nutr., 1999, 81:121-32), research and development in this area has boomed. Additionally, prebiotics are often found naturally in the food supply, especially fermented foods and are generally compatible with most food formulations (Macfarlane, S. et al., Aliment Pharmacol. Ther., 2006, 24:701-14; Manning, T. S. et al., Best Pract. Res. Clin. Gastroenterol., 2004, 18:287-98). By definition, glucooligosaccharides are prebiotic agents, and many forms are commercially available.

Glucooligosaccharides are a class of carbohydrate oligomers that include isomaltooligosaccharides (IMO). IMOs are glucosyl saccharides with a core structure based on an α-(1→6) linked backbone that may include α-(1→4), α-(1→3) (nigerooligosaccharides) and\or α-(1→2) (kojioligosaccharides) linked branches (Yun, J. et al., Biotechnol. Lett., 1994, 16:1145-1150). These glucosidic linkages are found in commercial IMO syrups (Goffin, D. et al., Crit. Rev. Food Sci. Nutr., 2011, 51:394-409). While some glucooligosaccharide agents may be available, not all types of glucooligosaccharides are excellent prebiotic agents and removal of contaminants from such agents can be problematic and expensive.

SUMMARY

Efficient, low cost methods are described herein for making prebiotics that contain maltosyl-isomaltooligosaccharides (MIMOs). The methods are particularly effective at removing excess unwanted co-products such as mannitol and fructose.

A method is described herein the includes:
(a) providing a fermentation broth comprising maltosyl-isomaltooligosaccharides, dextransucrase/alternansucrase-producing microorganisms, and culture media;
(b) removing the microorganisms from the fermentation broth to provide a cell-free fermentation broth; and
(c) passing the cell-free fermentation broth through a nanofiltration unit with at least one membrane having a molecular weight cut-off of 450-500 Da to produce a nanofiltered product.

In such a method the fermentation broth can provided by
(a) generating a culture medium comprising a sucrose to maltose ratio (S/M) of more than 2.7;
(b) initiating a fermentation reaction within the culture medium by adding 5% to 15% w/w dextransucrase/alternansucrase-producing microorganisms to the culture medium; and
(c) conducting fermentation within the culture medium for 16-24 hours to generate a fermentation broth.

For example, the culture medium can have a sucrose to maltose ratio (S/M) of about 2.90 to 2.92.

The cell-free fermentation broth or the nanofiltered product can be passed through a strong acid cation ion exchange resin, a weak anion ion exchange resin, or both to produce an ion exchange treated product. The pH of the ion exchange treated product can be adjusted to a pH less than to thereby produce a pH adjusted product. The pH adjusted product can be concentrated to produce a concentrated MIMO product. The concentrated MIMO product can be filtered through a microfilter to produce a microfiltered MIMO product. The microfiltered MIMO product can be pasteurized to produce a pasteurized MIMO product.

Optionally during such a method, one or more of the nanofiltered product, ion exchange treated product, pH adjusted product, concentrated MIMO product, or microfiltered MIMO product can be filtered through a carbon filter.

A method of producing a pasteurized nanofiltered product is also described herein, where such a method can include: concentrating the nanofiltered product to produce a concentrated nanofiltered product, optionally adjusting the pH of the nanofiltered product to produce a pH adjusted concentrated nanofiltered product, optionally filtering the concentrated nanofiltered product or the pH adjusted concentrated nanofiltered product through a carbon filter to produce a carbon filtered nanofiltered product, optionally filtering the concentrated nanofiltered product, the pH adjusted concentrated nanofiltered product, or the carbon filtered nanofiltered product through a microfilter to produce a microfiltered nanofiltered product, and pasteurizing the concentrated nanofiltered product or the microfiltered nanofiltered product to produce a pasteurized nanofiltered product.

A method of producing a pasteurized ion exchange treated product is also described herein, where the method can include concentrating the ion exchange treated product to produce a concentrated ion exchange treated product, optionally adjusting the pH of the concentrated ion exchange treated product to produce a pH adjusted concentrated ion exchange treated product, optionally filtering the concentrated ion exchange treated product or the pH adjusted concentrated ion exchange treated product through a carbon filter to produce a carbon filtered ion exchange treated product, optionally filtering the concentrated ion exchange treated product, the pH adjusted concentrated ion exchange treated product, or the carbon filtered ion exchange treated product through a microfilter to produce a microfiltered ion exchange treated product, and pasteurizing the concentrated ion exchange treated product or the microfiltered ion exchange treated product to produce a pasteurized ion exchange treated product.

The dextransucrase-producing microorganism can be of *Leuconostoc* spp., *Weissella* spp., *Lactococcus* spp., *Streptococcus* spp., *Lactobacillus* spp., or *Pediococcus* spp. In some cases, the dextransucrase-producing microorganism is

*Leuconostoc mesenteroides, Leuconostoc citreum, Leuconostoc gasicomitatum,* or *Leuconostoc kimchii.* For example, the dextransucrase-producing microorganism can be *Leuconosloc mesenteroides* ATCC 13146.

The nanofiltration unit can have at least one 500 Dalton cut-off Dalton nanofiltration membrane. For example, the nanofiltration unit can have 1 to 10 nanofiltration membranes.

In some cases, the pH adjusted product is passed one or more times through at least one microfilter with a molecular weight cut-off of 0.5 microns to 5 microns.

Pasteurizing can include heating to about 55° C. to 80° C. for about 15 minutes to about 60 minutes.

A manufacturing system is also described herein that can include:
- a cell removal unit;
- a nanofilter unit comprising at least one nanofilter comprising a molecular weight cut-off of 300 daltons to 700 daltons;
- an ion exchange resin unit comprising one or more of a strong cation ion exchange system or a weak base anion ion exchange resin unit;
- a pH adjustment unit;
- a liquid concentration unit;
- a microfiltration unit; and
- a pasteurization unit.

In some cases, the various units in the manufacturing can be operably linked together in various combinations. In addition, the manufacturing system can include a packaging unit, for example, to package the product after pasteurization.

The cell removal unit of the manufacturing system can, for example, include a cell filtration unit, a cell sedimentation unit, or a cell centrifugation unit.

The nanofilter unit of the manufacturing system can have about 1 to 10 nanofilters. For example, such a nanofilter unit can retain MIMOs with a degree of polymerization of at least three, MIMOs of greater than or equal to about 500 or 504 daltons.

A fermentation vessel can also be operably linked to the manufacturing system that, for example, includes a cell removal unit; a nanofilter unit comprising at least one nanofilter comprising a molecular weight cut-off of 300 daltons to 700 daltons; an ion exchange resin unit comprising one or more of a strong cation ion exchange system or a weak base anion ion exchange resin unit; a pH adjustment unit; a liquid concentration unit; a microfiltration unit; and a pasteurization unit.

Also described herein is a fermentation broth comprising: (a) broth components; (b) a mixture of oligosaccharides having a mass average molecular weight distribution (MWD) of 760-780 Da, oligosaccharides comprising 3 to 9 glucose subunits linked by α-(1→6) glucosyl linkages and terminated with a maltose subunit linked to the terminal glucose subunit by an α-(1→4) glucosyl linkage; and (c) fructose and mannitol in a ratio of about 1.69:1 or about 20.4:12.1%/brix.

For example, manufacturing methods described herein can include:
a. providing a fermentation broth comprising maltosyl-isomaltooligosaccharides, dextransucrase/alternansucrase-producing microorganisms, and culture media;
b. removing the microorganisms from the fermentation broth to produce a cell-free fermentation broth;
c. passing the cell-free fermentation broth through at least one 200 dalton to 700 dalton molecular weight cut-off nanofiltration unit to produce a nanofiltered product;
d. passing the nanofiltered product through a strong acid cation ion exchange resin to produce a cation exchange treated product;
e. passing the first ion exchange treated product through a weak base anion ion exchange resin to produce an anion exchange treated product;
f. adjusting the anion exchange treated product pH to a pH less than 5.5 to produce a pH adjusted product;
g. concentrating the pH adjusted product to produce a concentrated MIMO product;
h. filtering the concentrated MIMO product through a microfilter to produce a microfiltered product;
i. pasteurizing the microfiltered product to produce a pasteurized MIMO product; or
a combination thereof.

The fermentation broth can be manufactured by a method that includes one or more of the following steps:
a. generating a culture medium comprising a sucrose to maltose ratio (S/M) of greater than 2.0, or greater than 2.25, or greater than 2.5, or greater than 2.75, or greater than 2.8, or greater than 2.9, or greater than 3.0, or greater than 3.25, or greater than 3;
b. initiating a fermentation reaction within the culture medium by adding 5% to 15% w/w dextransucrase/alternansucrase-producing microorganisms to the culture medium;
c. conducting fermentation within the culture medium for 10-24 hours to generate a fermentation broth; or a combination thereof.

The pH of the culture medium during fermentation can be controlled to maintain the pH at about 5.3 to about 5.7, or at about 5.5.

DESCRIPTION OF THE FIGURES

FIG. 1A is a schematic diagram illustrating a process involving manufacture of MIMOs by fermentation, filtration cleanup of the fermentation broth, and cleanup by ion exchange. Although the diagram indicates filtration can occur after fermentation, the fermentation fluid can be centrifuged to remove particulates, and then filtration can be performed. Hence, the process can include additional steps. FIG. 1B is a schematic diagram illustrating a process that can be a continuation of the process shown in FIG. 1A involving the same ion exchange cleanup step shown in FIG. 1A, as well as filtration, concentration (e.g., by evaporation), pasteurization, and packaging of MIMO products. FIG. 1C illustrates an example of a nanofiltration unit.

DETAILED DESCRIPTION

Figure 1A:
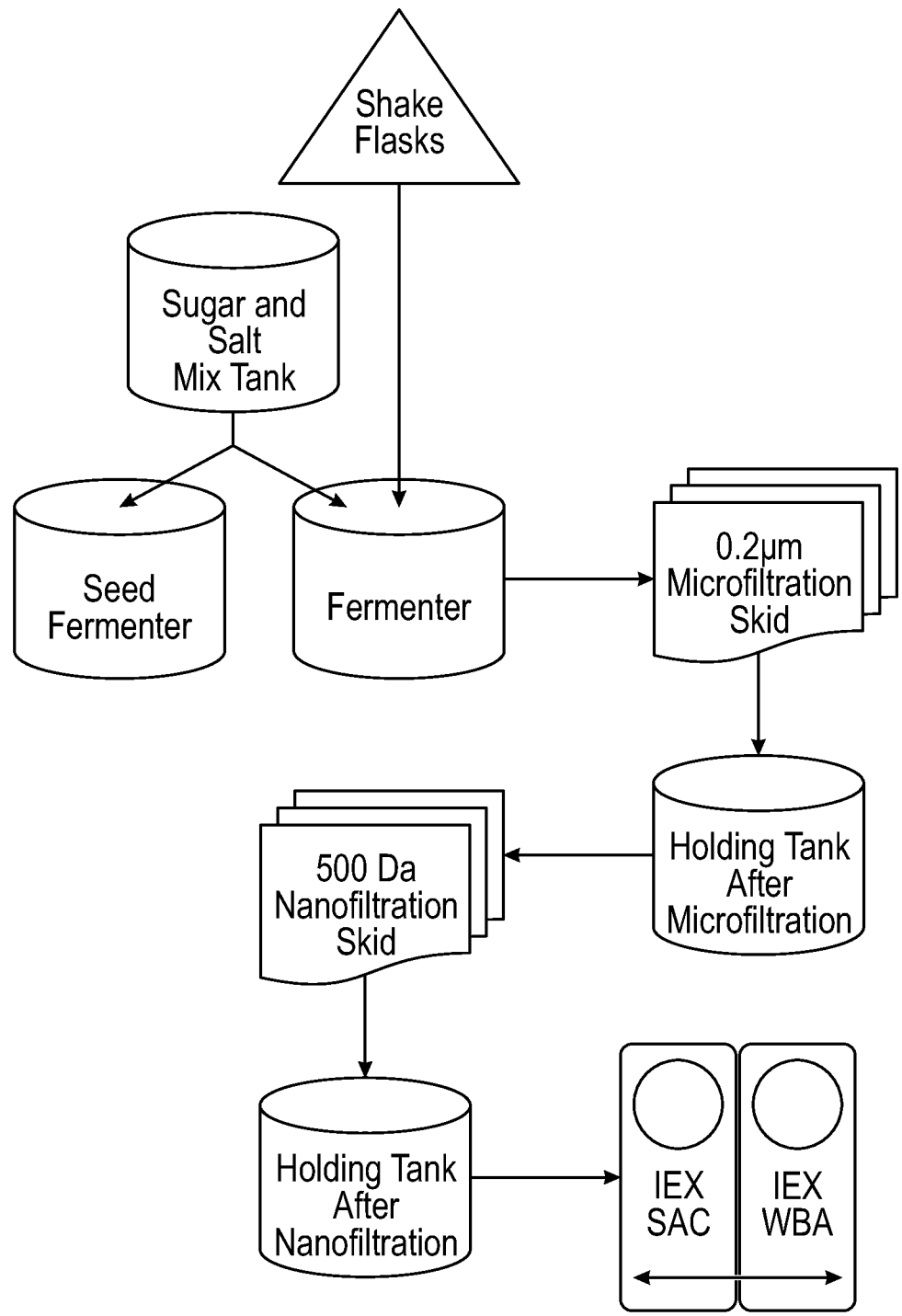
FIG. 1A-1C are schematic diagrams illustrating an example of a process for manufacturing maltosyl-isomaltooligosaccharides (MIMOs).

Methods and systems are described herein that are useful in the fermentation manufacture of oligosaccharides such as maltosyl-isomaltooligosacchrides (MIMOs). Certain metabolites, particularly D-mannitol and organic acids, are typically generated during fermentation that previously were difficult to remove from the MIMO product composition. The methods described herein solve this problem. These methods can involve several processing steps of broth from fermentation reactions where dextransucrase/alternansucrase-producing microorganisms have converted sugars (e.g., sucrose and maltose) into maltosyl-isomaltooligosacchrides (MIMO). The methods can, for example, involve steps such as centrifugation, microfiltration, nanofiltration, ion-exchange, concentration, pasteurization, and combinations thereof.

The manufacturing methods described herein are designed to produce maltosyl-isomaltooligosacchrides (MIMO) and compositions that contain MIMO. The MIMO compositions can also include other ingredients, including some of the components of the fermentation broth. By employing the manufacturing procedures described herein MIMO of desired mass average molecular weight distribution (MWD) and with selected fermentation components (e.g., some mannitol and/or other fermentation products) at desirable concentrations can be produced.

An example of an MIMO with a single maltosyl linkage [—O-α-(1,4)-] at the reducing end, and a DP of 5, can have the following chemical structure:

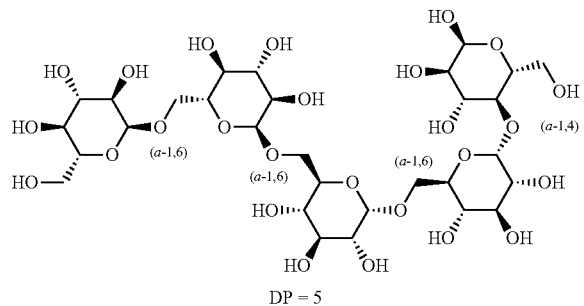 [SMILES: OC[C@H]1O[C@H](OC[C@H]2O[C@H](OC[C@H]3O[C@H](OC[C@H]4O[C@H](O[C@H]5[C@H](O)[C@@H](O)[C@@H](O)O[C@@H]5CO)[C@H](O)[C@@H](O)[C@@H]4O)[C@H](O)[C@@H](O)[C@@H]3O)[C@H](O)[C@@H](O)[C@@H]2O)[C@H](O)[C@@H](O)[C@@H]1O]

DP = 5

The MIMOs in the compositions described herein can have a number of glucose units. For example, the MIMOs in the compositions described herein can have from about 2 to about 18 glucose units, or about 2 to about 17 glucose units, or about 3 to about 16 glucose units, or about 3 to about 15 glucose units, or about 3 to about 14 glucose units, or about 3 to about 13 glucose units, or about 3 to about 12 glucose units. In general, the maltose-containing oligosaccharides have no more than about 24 (detectable) glucose units, or no more than about 22 glucose units, or no more than about 20 glucose units, or no more than about 17 glucose units, or no more than about 16 glucose units, or no more than about 15 glucose units, or no more than about 14 glucose units, or no more than about 13 glucose units, or no more than about 12 glucose units, or no more than about 11 glucose units, or no more than about 10 glucose units, for example, as detected by HPAEC-PAD or HPLC-RID.

The MIMOs in the compositions described herein can also have small numbers (e.g., one or two) of α-(1,2), α-(1,3), and α-(1,4) glucosyl linkages from the α-(1,6) backbone chain. Hence, the MIMOs in the compositions described herein can have small numbers of branch points. For example, the MIMOs in the compositions described herein can have 0-3 branch points, or 0-2 branch points, or 0-1 branch points.

Methods of Producing MIMO Compositions

On a commercial scale, the composition of the present invention can be produced as described in U.S. patent application Ser. No. 14/833,094, filed Aug. 22, 2015, entitled "Process for the Production of Isomaltooligosaccharides," and/or U.S. patent application Ser. No. 15/409,223, filed Jan. 18, 2016, entitled "Maltosyl-Isomaltooligosacchrides," both of which applications are incorporated by reference herein in their entireties.

Figure 1B:
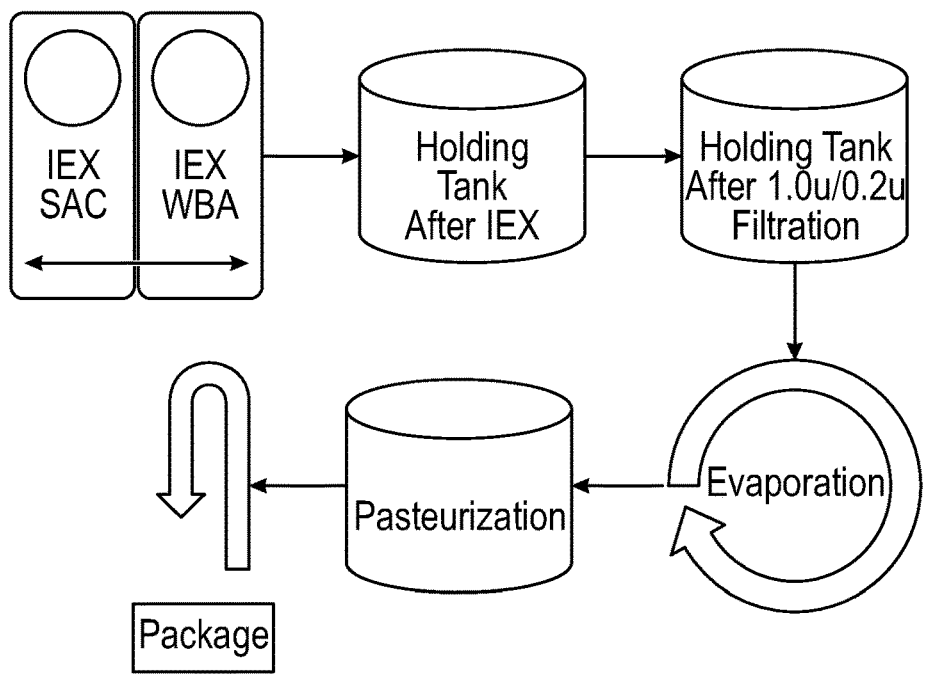

A process flow diagram of an exemplary manufacturing process is provided in FIG. 1. In general, two broad series steps are used to manufacture MIMOs. First, the MIMOs are synthesized via fermentation in a rich medium containing sugars (e.g., sucrose and maltose) and an extracellular dextransucrase enzyme expressed by a suitable organism. Second, downstream processing is performed to remove biomass, residual salts/minerals/sugars, and bacterial metabolites.

Microorganisms are used for synthesis of MIMOs that are capable of producing dextransucrase, alternansucrase, or combinations thereof. Dextransucrase is a glucosyl transferase that catalyzes the transfer of a glucose residue from sucrose to a growing polyglucan chain. Dextransucrase is often used to make dextran from sugars such as sucrose. However, in the presence an acceptor molecule (such as maltose), dextransucrase can generate MIMOs. When such an acceptor molecule (e.g., maltose) is present, dextransucrase synthesis of dextran can be "interrupted" by the acceptor molecule, causing the growth of the dextran oligosaccharide chain to terminate prematurely with an acceptor (e.g., maltose) subunit. In effect, the presence of an acceptor (such as maltose) limits the molecular weight of the oligosaccharide. When this occurs, specifically with maltose, short glucose chains terminated with maltose will result. These molecules are referred to as MIMOs or as panose-type maltosyl-isomaltooligosaccharides.

Many species of bacteria, for example *Leuconostoc* spp., produce one or more of these dextransucrases or alternansucrase enzymes. The branching pattern of dextran produced during growth of different bacteria is strain-dependent. Indeed, the branching patterns of the dextran formed by an organism can be used to speciate at strain level. Hence, the type of enzyme or microbe used to generate an oligosaccharide can significantly influence the ultimate structure of the oligosaccharide mixture produced.

For example, while *Leuconostoc mesenteroides* NRRL B-512F synthesizes dextran exopolysaccharides (EPS) that are almost completely unbranched, consisting of >95% α-(1,6) linkages, the dextran produced by *L. mesenteroides* NRRL B-1299 contains a distribution of three branched oligomers per DP [roughly 65% α-(1,6), 22% α-(1,2), and 12% α-(1,3)], and *L. citreum* NRRL B-742 produces a dextran that is somewhere in between and can contain 5%-15% α-(1,3). The differences may, in the case of NRRL B-512F, be attributed to a single sucrose glucan transferase enzyme that is responsible for α-(1,6) linkages. In the case of NRRL B-1299, the differences may be dues to at least three enzyme isoforms (Dols, et al. Appl Environ Microbiol 64(4): 1298-1302 1998). *L. mesenteroides* NRRL B-1299 is also capable of expressing glucose glucosyltransferase and fructose glucosyl transferase when grown on glucose and fructose medium, respectively (id.). These enzymes may create different branching patterns, as well.

The inventors have also observed that the same enzyme cohort (produced by *Leuconostoc mesenteroides* subsp. *mesenteroides* (Tsenkovskii) van Tieghem ATCC® 11449™ NRRL B-1299) produces a different branching pattern when immobilized than when it is native in free solution; the results were clear for DP 5 oligosaccharides.

Figure 3:
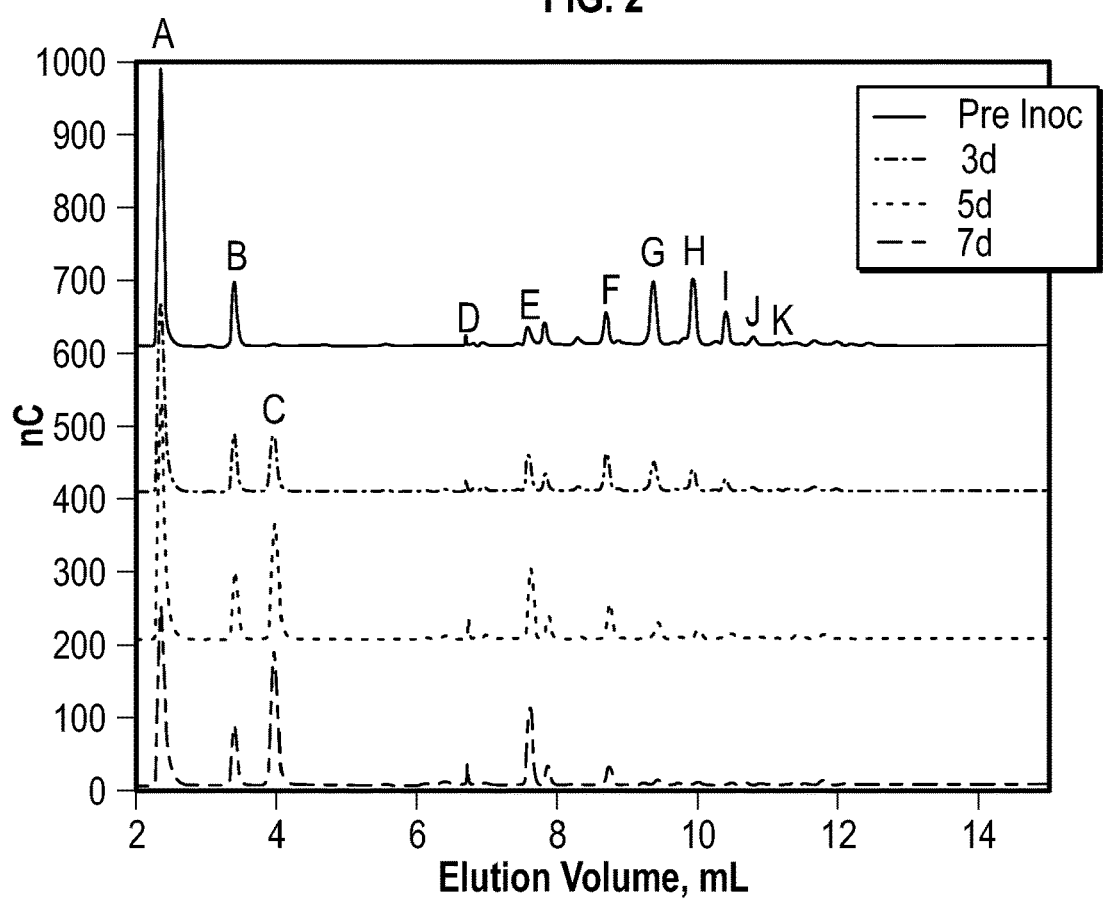
FIG. 3 shows HPAEC-PAD of (1) medium containing ISOThrive™ MIMO corresponding to "A2"-type material (see Example #1). Traces (2), (3), and (4) correspond to the same medium containing ISOThrive™ MIMO after inoculation and incubation with *L. casei* NRRL B-1922 for 3, 5, and 7 days, respectively. Labeled components are A: D-mannitol; B: L-arabinose (internal standard); C: D-glucose; D: sucrose; E: maltose; F: MIMO-DP3 (e.g., panose), and G-K: MIMO DP 4-8. Note that consumption of MIMO occurs via cleavage of maltose from the chain and depolymerization of the resulting α-(1,6) glucan backbone chain.

Both branching pattern and molecular weight can have a profound effect on the selectivity of a prebiotic composition. For example, Hu et al. (2013) noted that while *Lactobacillus reuteri* consumed shorter-chain MIMO, the longer chains (higher molecular weight) were preferred by Bifidobacteria. Further, which bacteria will eat a given prebiotic oligosaccharide depends on the glycolytic enzyme cohort expressed by that bacterial type. For example, the MIMO contained in the composition described herein [>80% linear α-(1,6); also called ISOThrive™], can be fermented by *Lactobacillus casei* NRRL B-1922. Evidence of this is provided in FIG. 3 where ISOThrive™ composite A2 (see Example #1) material is depolymerized to D-glucose and D-maltose. The compositions described herein (that include MIMOs such as those in ISOThrive™) can thus be characterized as prebiotics for *Lactobacillus casei* NRRL B-1922, which is representative of a probiotic bacterial class that is both large and popular.

Figure 4:
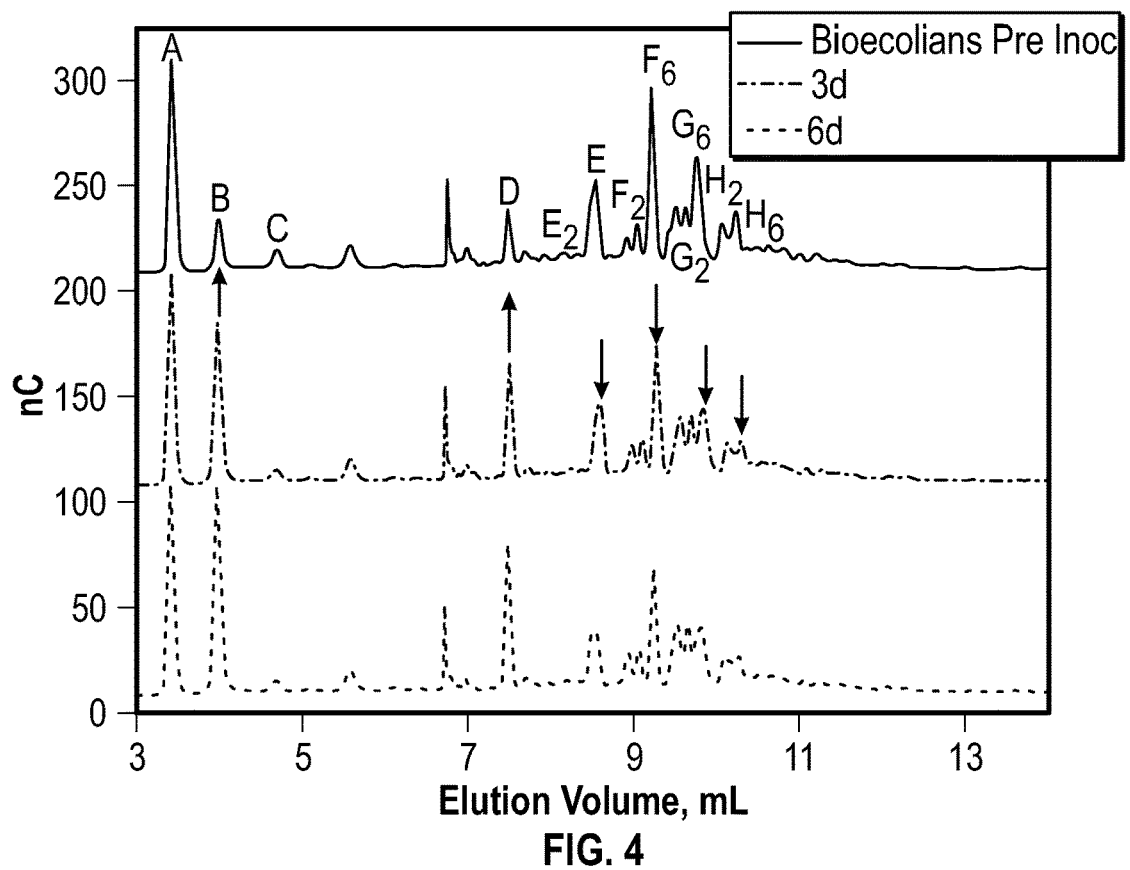
FIG. 4 shows HPAEC-PAD of (1) Fermentation medium made to contain a commercial MIMO product manufactured using an immobilized dextransucrase isolated from NRRL B-1299. Traces (2) and (3) correspond to the same medium containing the commercial MIMO product after inoculation and incubation with *L. casei* NRRL B-1922 for 3 and 6 days, respectively. Labeled components are A: L-arabinose (internal standard), B: D-glucose; C: D-fructose; D: maltose; where E, F, G, and H correspond to MIMO with linear α-(1,6) backbones ranging in DP from 3 to 6, and E2, F2, G2, and H2 correspond to MIMO with linear α-(1,6) backbones and either α-(1,2) or α-(1,3) glucosyl branches ranging in DP from 1 to 6. Note preferential consumption of the linear α-(1,6) molecules over the branched oligosaccharides.

By means of comparison with a composition containing a highly branched-type MIMO (e.g., produced via NRRL B-1299 dextransucrase), it can be demonstrated that α-(1,6) linkages are preferred by this organism, and that α-(1,2), and α-(1,3) linkages are not. This comparison is given in FIG. 4.

Examples of organisms capable of producing dextransucrase, alternansucrase, or combinations thereof include *Leuconostoc mesenteroides, L. citreum* ATCC 13146 (NRRL B-742), or combinations thereof. Bacteria known by designations such as *Leuconostoc citreum* ATCC 13146, the designation NRRL B-742, the designation *Leuconostoc citreum* Farrow. and the designation *L. amelibiosum, Leuconostoc mesenteroides* subsp. *mesenteroides* (Tsenkovskii) van Tieghem ATCC® 11449™ (NRRL B-1299) can also be employed. In addition, the inventors have also tested *L. citreum* B-1355, *Weissella confisa* B-1064, and *Lactobacillus sanfransiscensis* ATCC 27651. The B-1355 *L. citreum* B-1355 and *Weissella* bacterial strains make MIMOs and can make longer MIMO molecules.

Other useful dextransucrase/alternansucrase-producing microorganisms include, but not limited to, *Leuconostoc* spp (specifically *mesenteroides, citreum, gasicomitatum, carnosum, gelidum, inhae*, and *kimchi*), *Weissella* spp (specifically *confisa, kimchi*), *Lactococcus* spp., *Streptococcus* spp. (specifically *mutans*), *Lactobacillus* spp. (e.g. *reuteri*), *Pediococcus* spp. (specifically *pentosaceus*), and certain mutant *E. coli*.

Figure 5:
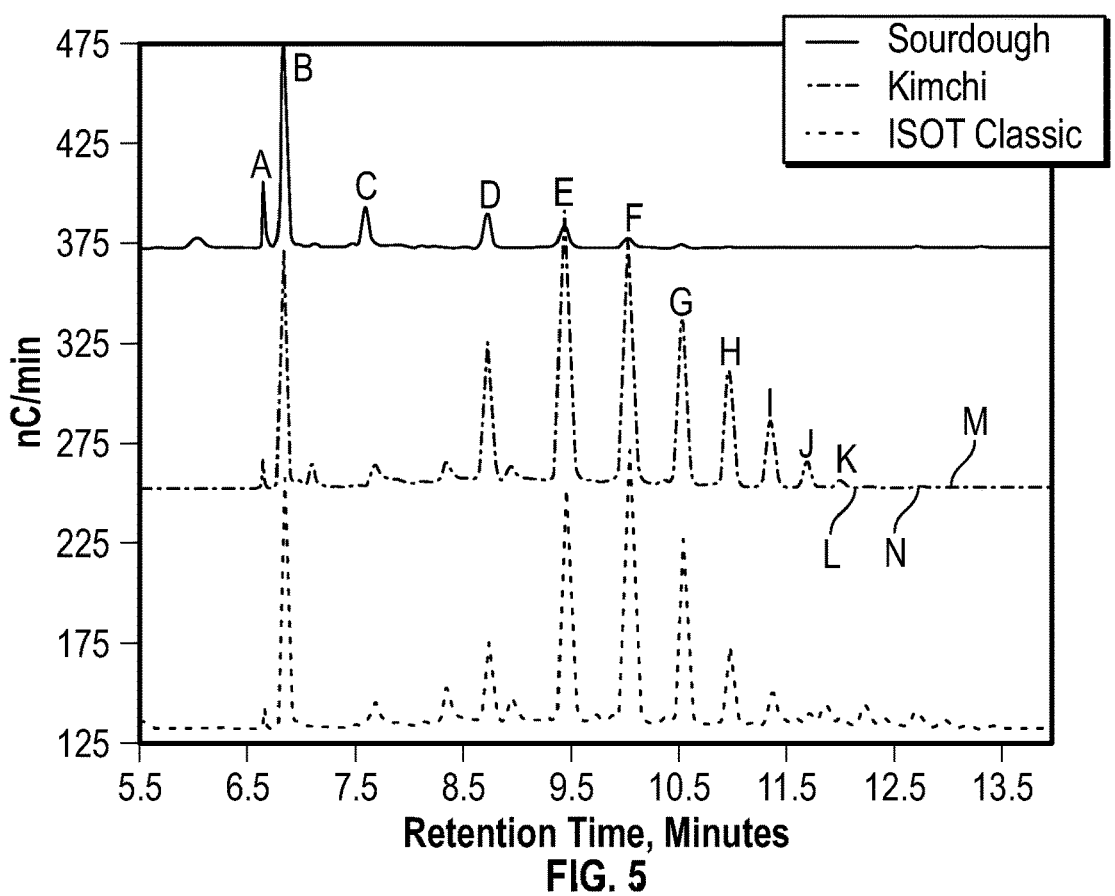
FIG. 5 HPAEC-PAD of (1) MIMO produced in a spontaneously fermented sourdough starter culture from hard red wheat (confirmed *P. pentosaceus* via sequencing of 16SrRNA); (2) Liquor separated from kimchi (found to contain several *Leuconostoc* spp., primarily *L. gasicomitatum*, via sequencing of 16SrRNA) with sucrose and maltose added at a ratio of 3:1; and (3) A sample of ISOThrive™ MIMO produced via fermentation of sucrose and maltose with NRRL B-742. Labeled components are A: sucrose; B. raffinose (internal standard), C: maltose, where D, E, F, G, H, I, L, M, and N correspond to MIMO with α-(1,6) linear backbones ranging in DP from 3 (panose) to 10.

Useful microorganisms, or mixed cultures thereof, may also be isolated from natural sources including, but not limited to, spontaneous (wild) sourdough starter cultures (the bioorganism mixture used in the production of sourdough bread) and *kimchi* see FIG. 5.

For example, the organism used in some of the Examples described herein is *Leuconostoc citreum* Farrow et al. ATCC 13146 (NRRL B-742).

The medium employed for growth and fermentation by various dextransucrase/alternansucrase-producing microorganisms can vary. However, when producing MIMOs, the mass average molecular weight distribution (MWD) of the MIMOs tends to increase with increasing sucrose:maltose (S/M) ratio present at the time of inoculation (see FIG. 6). In general, the sucrose:maltose ratio has a significant impact the MIMO molecular weight achievable in a fermentation.

Figure 6:
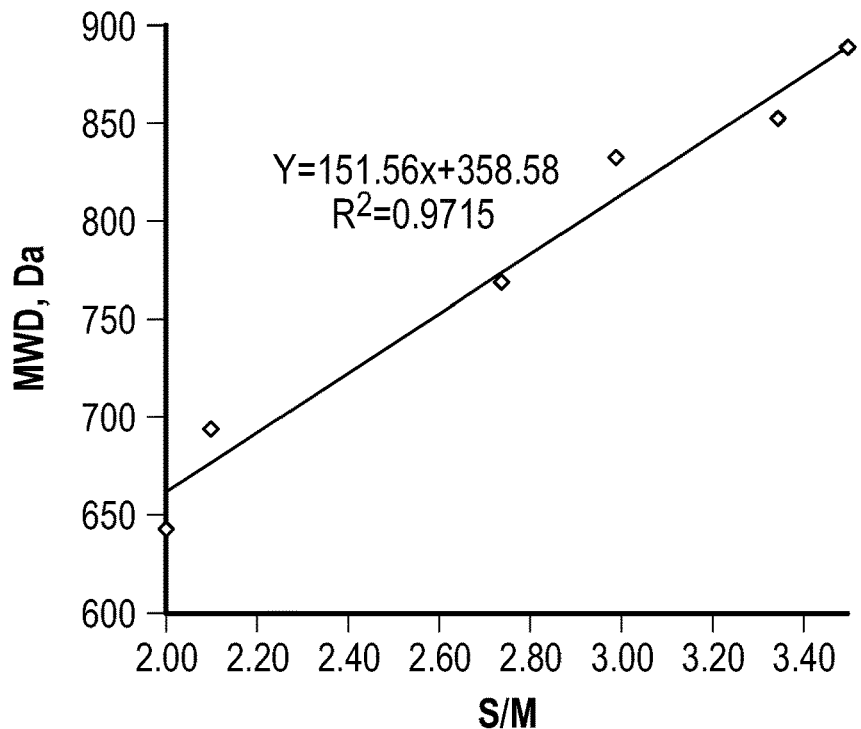
FIG. 6 shows the effect the sucrose:maltose (S/M, w/w) ratio at the time of inoculation has on the mass average molecular weight distribution (MWD) at a fixed pH of 5.5. As S/M increases, so does the molecular weight distribution.

For example, the mass average molecular weight distribution (MWD) of the MIMO tends to increase with sucrose: maltose (S/M) ratio used at the time of inoculation (see FIG. 6). The relationship between sucrose:maltose ratio and the MWD of the product can be approximated (6%, $R^2=0.9715$, N=29) as: MWD, Da=151.56*S/M+358.58.

However, experiments described herein show that a desirable starting sucrose to maltose ratio S/M can be more than 2.5, more than 2.6, more than 2.7, more than 2.8, or more than 2.9. For example, when high amounts of fermenting organism are used as an inoculum the S/M ratio at the time of inoculation can be about 2.90 to 2.92. The fermentation mixture can have a (starting) sucrose:maltose ratio of greater than 2.0, or greater than 2.25, or greater than 2.5, or greater than 2.75, or greater than 2.8, or greater than 2.9, or greater than 3.0, or greater than 3.25, or greater than 3.5.

However, it is generally desirable for the maximum total sugar in the starting medium to be less than 30% of the mass and lower than 34 brix.

Figure 7:
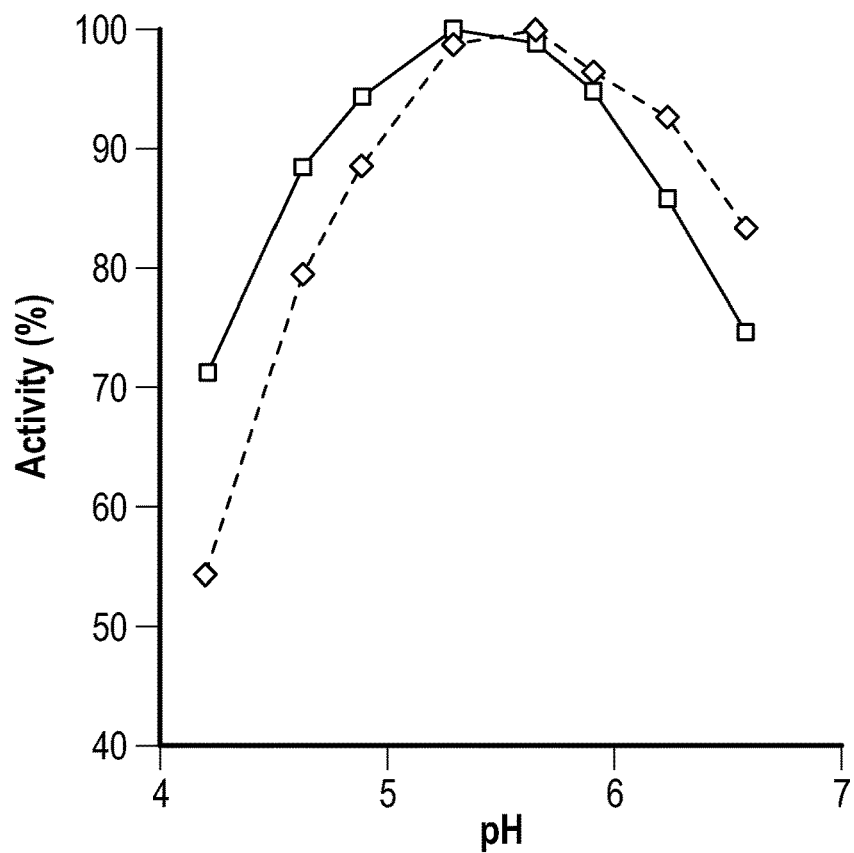
FIG. 7 shows the pH optimum for dextransucrase produced by *Leuconostoc mesenteroides* NRRL B-512F either without (white squares) or with (black squares) stabilization via added dextran T-70 (Monchois, et al. 1998). The mass average molecular weight distribution (MWD) increases as the optimum is approached.

The mass average molecular weight distribution is also dependent on the pH optimum of the dextransucrase(s) expressed by the fermenting organism. For dextransucrases from *Leuconostoc* spp. (NRRL B-512F, B-742, and B-1299), this optimum is about 5.5±0.3 (FIG. 7). This behavior with respect to pH appears to be conserved within enzymes produced by a variety of organisms. For example, the pH optimum for dextransucrase isolated from *Pediococcus pentosaceous* is 5.4 (Patel, et al. 2011) and that from *Streptococcus mutans* was optimum at 5.5 (Chludzinski et al. 1974). The pH optimum is rather broad, and can be affected by substrate concentration (Sarwat, et al. 2008), ionic strength, and the presence of certain cations such as magnesium and calcium (Patel, et al. 2011). Furthermore, gene deletions modifying the carboxy-terminus of the active site in dextransucrase from NRRL B-512F affected neither km nor the pH optimum (Monchois, et al. 1998). An example of a pH optimum curve for the B-512F dextransucrase enzyme is given in FIG. 7.

The mass average molecular weight distribution (MWD) can therefore relate to the pH employed, for example, when the sucrose:maltose ratio S/M is at about 2.00 (approximately 2.73 at time of inoculation). For example, an optimal pH may be between about pH 5.5 and 6.0 and can be approximated by the following:

$$\text{MWD, Da} = -159.1 \cdot pH^2 + 1866.1 \cdot pH - 4688.$$

The organisms generally used herein, including *Leuconostoc mesenteroides*, are capable of producing dextransucrase, and can be utilized to produce the composition containing maltosyl-isomaltooligosaccharides pursuant to the methods described herein. In another example, *L. citreum* ATCC 13146 (NRRL B-742) may be used.

In general, upon start-up of the fermentation process, the entire equipment system is flushed, cleaned and sterilized. A fermentation tank is charged with the requisite media components (typically containing vitamins, sulfates, phosphates, salts and other materials used for bacterial culture, as well as sucrose and maltose in a defined sucrose to maltose ratio). All ingredients can be non-GMO and certified Kosher/Pareve, including the bacterial vial stock.

Separately, an inoculum is obtained by growing one or more types of dextransucrase/alternansucrase-producing microorganisms (such as ATCC 13146) until achieving an optical density (OD, or absorbance observed at 660 nm via UV-VIS spectrophotometer) of at least 1-15. In some cases, the OD is at least 1.5, or at least 2.5, or at least 3.5, at least 4.5, at least 5.5, at least 26.5, at least 7.5, at least 8.5, at least 9.5, at least 10, at least 11 or at least 12. To measure optical densities greater than about 2, a sample can be diluted (e.g. serially diluted) and the OD readings can be calculated by taking the dilution factor into account. In some other cases, where pH is controlled, the OD is about 10 to about 15, or about 13. The inoculum is added to the fermentation mixture in a volume ranging from about 1% to about 15% wt/wt (in some cases 10% inoculum by mass) of the amount of bulk media.

The fermentation can take place at a temperature of about 27° C. and can be maintained at a pH of about 4.0-6.0 (5.5 in the preferred approach) via addition of a base, such as 50% w/w sodium hydroxide. The fermentation is typically not aerated, but the headspace can be pressurized with air as needed to maintain positive pressure.

The fermentation can be continued until no fructose is present, for example, for a period of approximately 5 to 60 hours, or 6 to 48 hours, or 7 to 36 hours, or 8 to 30 hours, or 9 to 25 hours, or 10 to 22 hours, or about 11 to 20 hours. In some cases, the time for optimal fermentation can be as little as about 15 to 18 hours, or about 17 hours. Hence, when conditions are optimized fermentation can be for less than 24 hours, less than 22 hours, less than 20 hours, less than 19 hours, or less than 18 hours.

Fermentation by previous methods typically takes about 25 to 60 hours, whereas when the improved methods are used the fermentation can be completed in 10-24 hours, or 16-25 hours or 17-24 hours.

Hence, the fermentation time can be reduced, especially when using the processing methods described herein.

Examples of the characteristics and behavior of the feedstock, products, and metabolites throughout the course of fermentation are given in the Examples. Most, if not all, of the sucrose and maltose are either consumed or converted to MIMO within a few hours, usually within about 10 hours.

The fermentation can be continued for a time thereafter to allow the MIMOs produced to be enzymatically rearranged to yield longer chains (higher MWD), if desired. Typically, the time required to create a product, for example, of target mass average molecular weight distribution (MWD) of 760-800 Da is less than about 60 hours, or less than about 55 hours, or less than about 50 hours, or less than about 50 hours, or less than about 48 hours, or less than about 40 hours, or less than about 36 hours, or less than about 30 hours, or less than about 24 hours, or less than about 20 hours, or less than about 18 hours, or less than about 16 hours, or less than about 14 hours.

The fermentation can be run with periodic sampling and analysis by HPAEC-PAD and/or NMR until a target MWD is reached. Once the optimal MWD is achieved impurities can be removed using the processes described herein.

In some cases, the optimal or target MWD is obtained when the broth is essentially free of fructose. In other cases, it can be obtained at any range of conversion of fructose to mannitol from no fructose to all fructose, or from no mannitol to all mannitol.

For example, as illustrated below the amount of fructose in fermentation broth corresponds to the metabolic maximum of the organism and the amount of sugar (sucrose) present (1 equivalent of fructose per mole of sucrose feed for a theoretical maximum of about 40%/brix of fructose at 100% yield and 0% conversion to mannitol). The conversion of sucrose to fructose is essentially quantitative. Conversion of fructose to mannitol can essentially be quantitative as well but some of the fructose is typically converted to metabolic products such as lactic, acetic, and formic acids, ethanol, and carbon dioxide. The quantity of mannitol at the end of the fermentation can therefore be the same as the amount of sucrose originally added to the medium (molewise) at the beginning of the fermentation minus the mole equivalent(s) of metabolic products for a theoretical maximum yield of about 28% brix. Ratios vary with the degree of conversion of fructose to mannitol. Final fermentation broths typically contain between 0 and 7%/brix fructose, and between 0 and 14%/brix of mannitol.

TABLE 1

Figure 30:
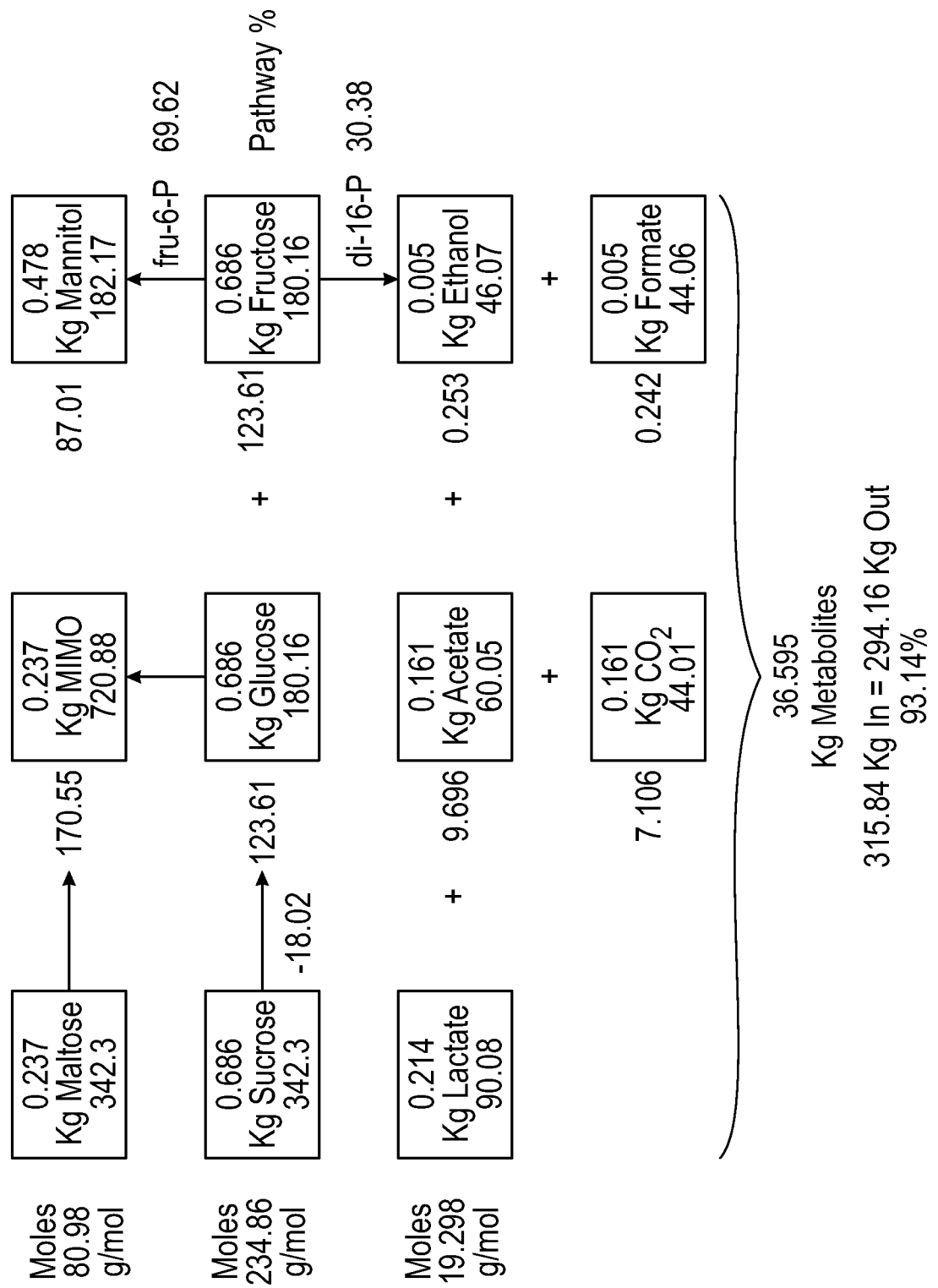
FIG. 30 illustrates pathways that can occur during fermentation with a balance of mass for such pathways shown in Table 1.

Balance of Mass for the Pathways depicted in FIG. 30

|  | kg: | % w/w: | %/brix: | Moles: |
|---|---|---|---|---|
| FEED ----->IN |  |  |  |  |
| SUCROSE | 234.86 | 20.82 | 74.36 | 686.11 |
| MALTOSE | 80.98 | 7.18 | 25.64 | 236.59 |
| TOTAL | 315.84 | 28.00 | 100.00 | 922.70 |
| ENZYMIC <----OUT #1 |  |  |  |  |
| MIMO | 170.55 | 15.12 | 54.00 | 236.59 |
| FRUCTOSE | 123.61 | 10.96 | 39.14 | 686.11 |
| TOTAL | 294.16 | 26.08 | 93.14 | 922.70 |
| METABOLIC <----OUT #2 |  |  |  |  |
| MIMO | 170.55 | 15.12 | 54.00 | 236.590 |
| MANNITOL | 87.01 | 7.71 | 27.55 | 477.652 |
| LACTATE | 19.298 | 1.71 | 6.11 | 214.230 |
| ACETATE | 9.696 | 0.86 | 3.07 | 161.470 |
| $CO_2$ | 7.106 | 0.63 | 2.25 | 161.470 |
| ETHANOL | 0.253 | 0.02 | 0.08 | 5.485 |
| FORMATE | 0.242 | 0.02 | 0.08 | 5.485 |
| TOTAL | 294.16 | 26.08 | 93.14 | 1262.38 |

However, in some cases the target MWD for the MIMO product in the final fermentation fluid can, for example, be achieved without monitoring conversion of most of the fructose to mannitol. For example, the final fermentation can have a total sugar content that is more than 20% brix, or more than 22/brix, or more than 23%/brix, or more than 24%/brix, or more than 25% brix, or more than 26 brix, or more than 27% brix, or about 27% brix to 30% brix. Some of the sugars can be fructose and some can be mannitol where the ratio of fructose to mannitol can vary.

For example, the final fermentation broth can contain 0%/brix fructose or more, 1%/brix fructose or more, 2%/brix fructose or more, 3%/brix fructose or more, 4%/brix fructose or more, 5%/brix fructose or more, 6%/brix fructose or more, or 7%/brix fructose or more, 9%/brix fructose or more, 10%/brix fructose or more, 15%/brix fructose or more, 20%/brix fructose or more, 30%/brix fructose or more, or 40%/brix fructose or more. Similarly, the final fermentation broth can contain 0%/brix mannitol or more, 10%/brix mannitol or more, 2%/brix mannitol or more, 3%/brix mannitol or more, 4%/brix mannitol or more, 5%/brix mannitol or more, 6%/brix mannitol or more, 7%/brix mannitol or more, 8%/brix mannitol or more, 9%/brix mannitol or more, 10%/brix mannitol or more, 11%/brix mannitol or more, 12%/brix mannitol or more, 13%/brix mannitol or more, 14%/brix mannitol or more, 15%/brix mannitol or more, 17%/brix mannitol or more, 20%/brix mannitol or more, 22%/brix mannitol or more, 24%/brix mannitol or more, 26%/brix mannitol or more, 27%/brix mannitol or more, 28%/brix mannitol or more, 29%/brix mannitol or more, 30%/brix mannitol or more, 33%/brix mannitol or more, 35%/brix mannitol or more, or 40%/brix mannitol or more.

During the production of maltosyl-isomaltooligosaccharides, the number of MIMO chains is established at the point where sucrose reaches its minimum and fructose reaches its maximum, which is typically 10 hr. Following this, the fructose is either metabolized or converted to mannitol. If a sample is taken at 16 hr, the MWD can be used to estimate how long it will be before the target mass average molecular weight distribution (MWD) is achieved and the batch is suitable for harvest. While this point can be correlated with fructose/mannitol, in some cases, estimation of the molecular weight distribution (MWD) as a function of time is the preferred method for determining when the fermentation step can be terminated.

In general, it can be desirable to remove some of these sugars, while leaving sufficient mannitol to be organoleptically desirable for the final product.

Because the downstream processing is so efficient, undesired amounts of fructose and other components can readily be removed. Hence, manufacturing and energy costs can be reduced while still achieving a target MWD in a short fermentation time (e.g., 16-18 hours) that would otherwise produce a fermentation broth that include significant amounts of various sugars and of other components that may not be desirable in the final product. Because the manufacturing times are so low and the downstream processing steps so efficient, the efficiency and energy cost savings can be substantial.

After fermentation has been terminated and the fermentation broth can be used as a useful product without additional purification, or it can be subjected to one or more downstream processing steps to provide a semi-purified or purified product. For example, in some cases the fermentation process produces useful products in addition to MIMOs. A product that contains both the MIMOs and other fermentation products is therefore useful.

Downstream Processing

In methods used before the development of the invention, such as those described for example in U.S. Patent Application 20170275661, the MIMO fermentation was performed with a smaller inoculum and a lower sucrose:maltose ratio. However, such older methods require longer fermentation runs, for example, of about 40 to 60 hours. In such a process, the originally added sugars, as well as the fructose cleaved from the sucrose, will typically be depleted, and while there will be mannitol in the final fermentation broth there will be little or no fructose remaining in the fermentation liquid. The longer fermentation time was partly chosen to allow the metabolic conversion of fructose to mannitol in effect as an alternative to filtering it out of the broth to bring the final product sufficiently low fructose levels.

However, when the downstream processing described herein are performed, components such a fructose, mannitol, and other components can be removed or reduced until desirable levels are obtained. Hence, the fermentation can be performed until MIMOs of an optimal or desirable molecular weight is obtained, which can occur when much shorter fermentation times are used and there may be no need to monitor fructose conversion to mannitol. For example, a fermentation of about 8 to 40 hours, or about 8 to 35 hours, or about 8 to 24 hours, or about 9 to 24 hours, or about 10 to 24 hours, or about 14 to 24 hours, or about 16 to 24 hours, or about 19 to 23.5 hours can provide a final fermentation fluid with an optimal MIMO molecular weight. However, such a short (e.g., 8-24 hour) final fermentation broth can contain fructose levels of 5% w/w or more, with the total sugar content being about 27% to 29% of the 31-33 total % brix in the solution. But this is not a problem because, if desired, the fructose and other sugars can readily be removed via the nanofiltration process.

After fermentation, the broth can be subjected to downstream processing to provide a semi-purified or purified MIMO preparation. The steps involved in downstream processing can in some cases be performed by a series of units that can be connected (e.g., be in-line). In general, the downstream processing steps can include:

(a) cell removal;
(b) cleanup by filtration;
(c) cleanup by ion exchange;
(d) filtration;
(e) acidification;
(f) concentration;
(g) pasteurization; or
(h) a combination thereof.

Each step can be performed by one or more units that accomplish that step of the process.

The cells can be separated from the fermentation broth by microfiltration, centrifugation, sedimentation, or by other broth clarification processes. The cells are typically discarded. In some cases, the cells can be removed by microfiltration, for example, by a microfiltration unit with one or more microfiltration membranes having pores of 0.1 microns to 10 microns. For example, the molecular weight cut-off within such a microfiltration unit can be at least 0.1, or 0.2, or 0.3, or 0.4, or 0.5, or 0.6 microns in size. Such microfiltration can be performed using a series of microfiltration membranes. For example, a skid of at least one, or at least two, or at least three, or at least four, or at least five, or at least six 0.1 to 0.3 (e.g. 0.2) micron microfiltration membranes can be present in a microfiltration skid. The majority (e.g., essentially all) of the MIMOs are present in the permeate of such microfiltration.

Some of the MIMO may be retained by the cell mass, retentate, and/or by the microfiltration apparatus. Hence, the cell mass and retentate can be washed, or washed and re-filtered/re-centrifuged, and/or the microfiltration apparatus can be flushed or rinsed to collect more of the MIMO. The collected fluid can be combined with the microfiltration permeate to provide a cell-free fermentation broth.

Hence, several rounds of centrifugation, washing, dilution, or combinations thereof can be performed capture more MIMO and to improve MIMO yield. For example, at least one, or at least two, or at least three, or at least four steps of washing, dilution, centrifugation or combinations thereof can be performed to provide the cell-free fermentation broth. The cell mass can also be dewatered in this step as well.

Such a cell-free fermentation broth typically contains no detectable microorganisms or cells. However, in some cases the cell-free fermentation broth may contain small numbers of cells. For example, the cell-free fermentation broth may contain less than 1000 microorganisms or cells per liter, less than 100 microorganisms or cells per liter, less than 10 microorganisms or cells per liter, or less than 5 microorganisms or cells per liter. Such small numbers of microorganisms or cells can be removed by subsequent steps in the downstream processing.

Various types of molecules can be removed from the cell-free fermentation broth by one or more cleanup steps. For example, cleanup can involve steps such as nanofiltration, ion exchange, and combinations thereof.

A first cleanup step can involve nanofiltration to provide a nanofiltered product. Nanofiltration can involve use of one or several of membranes. In some cases, nanofiltration can be performed using a number of nanofiltration membranes configured in parallel. Acceptable membrane types include: flat or tubular, cross flow, spiral wound, plate and frame, hollow fiber, capillary, gel-type, and other membrane types. In some cases, nanofiltration can be performed using a series of nanofiltration membranes.

For example, a nanofiltration skid can be used that has at least one, or at least two, or at least three, or at least four, or at least five, or at least six, or at least seven, or at least eight, or at least nine, or at least ten nanofiltration membranes (e.g., plumbed in parallel). The nanofiltration membrane(s) can have a molecular weight cut-off that retains molecules of a selected size. For example, nanofiltration membrane(s) can have a molecular weight cut-off that is larger than about 200 daltons, or larger than about 250 daltons, or larger than about 300 daltons, or larger than about 400 daltons, or larger than about 450 daltons, or larger than about 500 daltons, or larger than about 525 daltons. In some cases, the nanofiltration step and/or nanofiltration unit retains MIMOs with a degree of polymerization of at least three (e.g., a MIMO size of about 500 or 504 daltons).

Such a nanofiltration skid can have filter elements of varying lengths, for example, lengths of at least five feet, or at least seven feet, or at least eight feet, or at least ten feet, or at least eleven feet, or at least twelve feet, or at least thirteen feet, at least fourteen, at least fifteen, at least sixteen, at least seventeen, at least eighteen, at least nineteen, at least twenty, at least twenty-one, at least twenty-two, or at least twenty-three.

Such a nanofiltration unit skid is useful for removal of waste from the fermentation broth and it also de-waters the broth and hence reduces the amount of evaporation needed. The permeate of such a nanofiltration unit can contain mineral salts, organic acid salts, mannitol, residual sugars, ash, and color. Very little, if any MIMO passes the membrane. Hence, the retentate can be diluted and washed with added water or buffer to remove such salts, sugars, mannitol, ash, and color. For example, the retentate can be diluted to maintain the ideal flux rate through the membrane until the desired configuration of the retentate or the filtrate liquid is achieved.

Water as well as small molecules are removed by such nanofiltration. Fresh water can be added to the feed to further reduce the amounts of salts, sugars, ash, and other small molecules in the MIMO product retained by the nanofiltration unit (also referred to as a "nanofiltered product"). Such a first cleanup step can therefore remove water, salts, sugars (such as glucose, fructose and/or mannitol), ash, and other small molecules from the MIMOs more simply and less expensively than other methods such as liquid chromatography or crystallization.

A second cleanup step can be employed that can include passing the nanofiltered product (containing MIMOs) through one or more ion exchange resins. For example, the nanofiltered product can be contacted first with a strong acid cation (SAC) ion exchange resin, and then second with a weak base anion (WBA) IEX resin. Such a second cleanup step can remove balance of ash, organic acids, protein, color, odor, or combinations thereof.

The pH of the resulting product of ion exchange cleanup can be adjusted to a pH less than 5.5, or less than 5.3, or less than 5.0, or less than 4.8, or less than 4.7, or less than 4.6, or less than 4.5, or less than 4.4, or less than 4.3, or less than 4.1, or less than 4.0, or less than 3.9, or less than 3.5, or less than 3.2, or less than 3.0, or less than 2.9, or less than 2.8, or less than 2.7 to produce a pH-adjusted product that once concentrated will have a final pH of less than 2.0, or less than 2.28, or less than 2.3, or less than 2.4, or less than 2.5, or less than 2.6, or less than 2.7, or less than 2.8, or less than 2.9, or less than 3.0. For example, the product of the ion exchange cleanup step can have a pH of about 2.1 to about 5.0, or about 2.1 to 4.5, or about 2.1 to about 4.0, or about 2.2 to about 3.5, or about 2.2 to about 3.0, or about 2.2. to about 2.6 A variety of acidulants may be added can be used including, but not limited to, organic acids including citric, malic, lactic, tartaric, fumaric, succinic, ascorbic, benzoic, adipic, caprylic, propionic, acetic acids, and salts (mono, di- and tri-Na, Mg, Ca, etc.), stereoisomers (L/D, R/S, meso), rotamers, esters, and mixtures thereof, and mineral acids including phosphoric, hydrochloric, sulfuric, and salts, esters, and mixtures thereof, and amino acids, including lysine, cysteine, methionine, glutamic, and aspartic acids, and salts, esters, and mixtures thereof. In some cases, the acid can be phosphoric acid ($H_3PO_4$, e.g., 85% $H_3PO_4$) can be employed.

After acidification, the pH-adjusted product can be filtered through one or more microfiltration membranes or microfiltration units. For example, one or more of the microfiltration unit can have pores of 0.1, or 0.2, or 0.3, or 0.4, or 0.5 microns in size. Such microfiltration can be performed using a series of microfiltration membranes. For example, a microfiltration unit can have at least one, or at least two, or at least three, or at least four, or at least five, or at least six 0.1 to 0.5 micron, or 0.1 to 0.3 (e.g. 0.2) micron microfiltration membranes. In some cases, a 0.45 micron filter followed in serial by a 0.2 micron filter can be used. Larger filters such as 0.5-5.0 micron filters can be used before smaller pore membranes to remove solids, if present.

After such microfiltration the microfiltered product can be concentrated by evaporation to 61-70 brix (64-65 brix is preferred) to produce a concentrated MIMO product. The concentrated MIMO product can be pasteurized to yield a final MIMO product that can be packaged. Such pasteurization can be performed at about 60° C. to 75° C., or at about 70° C. The time for pasteurization can vary from about 20 minutes to about 45 minutes, or for about 30 minutes.

Previously, crystallization has been used to remove the mannitol, for example, as described in U.S. Patent Application 20170275661. In such a process, the fermentation was typically continued until fructose has been completely converted into mannitol (typically about 48-60 Hr). However, a crystallization can increase costs and the time required for manufacturing. Hence, a crystallization step is typically not performed.

However, when using nanofiltration to remove mannitol and other components with molecular weights less than 500 daltons, the fermentation can be continued until MIMOs of a desired molecular weight is achieved. When there is a typical 4-hour lag phase after inoculation with 1% w/w, the desired MIMO molecular weight can be achieved in about 48 to 56 hours). However, when the inoculum is about 10% w/w, there is essentially no lag time and the desired average MIMO molecular weight can be achieved faster. For example, the desired average M IMO molecular weight can be achieved when using a 10% inoculum in as little as about 15-19 hours.

However, it can be desirable to retain a certain amount of mannitol (for example, less than or equal to about 5% weight of product or 7.7%/brix). When using nanofiltration to clean up the MIMOs, if for example there is an approximate 1:1 ratio of fructose:mannitol in the feed, equal amounts of mannitol and fructose can be removed by the nanofiltration, and the rate of removal will also be about the same.

In some cases, the amount of mannitol remaining after nanofiltration can be about 8%/brix to substantially no (0%) mannitol. Similarly, in some cases, the amount of fructose remaining after nanofiltration can be about 8%/brix to substantially no (0%) fructose.

In some cases, the final MIMO product can contain 0%/brix fructose or more, 1%/brix fructose or more, 2%/brix fructose or more, 3%/brix fructose or more, 4%/brix fructose or more, 5%/brix fructose or more, 6%/brix fructose or more, or 7%/brix fructose or more, 9%/brix fructose or more, 10%/brix fructose or more, 15%/brix fructose or more, 20%/brix fructose or more, 30%./brix fructose or more, or 40%/brix fructose or more, or 1%/brix fructose or less, 2%/brix fructose or less, 3%/brix fructose or less, 4%/brix fructose or less, 5%/brix fructose or less, 6%/brix fructose or less, 7%/brix fructose or less, or 8%/brix fructose or less.

Similarly, the final MIMO product can contain 0%/brix mannitol or more, 1%/brix mannitol or more, 2%/brix mannitol or more, 3%/brix mannitol or more, 4%/brix mannitol or more, 5%/brix mannitol or more, 6%/brix mannitol or more, 7%/brix mannitol or more, 8%/brix mannitol or more, 9%/brix mannitol or more, 10%/brix mannitol or more, 11%/brix mannitol or more, 12%/brix mannitol or more, 13%/brix mannitol or more, 14%/brix mannitol or more, 15%/brix mannitol or more, 17%/brix mannitol or more, 20%/brix mannitol or more, 22%/brix mannitol or more, 24%/brix mannitol or more, 26%/brix mannitol or more, 27%/brix mannitol or more, 28%/brix mannitol or more, 29%/brix mannitol or more, 30%/brix mannitol or more, 33%/brix mannitol or more, 35%/brix mannitol or more, or 40%/brix mannitol or more, or 1%/brix mannitol or less, 2%/brix mannitol or less, 3%/brix mannitol or less, 4%/brix mannitol or less, 5%/brix mannitol or less, 6%/brix mannitol or less, 7%/brix mannitol or less, or 8%/brix mannitol or less.

For example, to achieve about 0.5% w/w of mannitol the MIMO preparations can be blended to achieve the desired composition. The blend stocks may include fermentation broths, semi-purified MIMOs, or purified MIMOs in various states (e.g., time-wise), nanofilter retentate in various cycles (e.g., depending how long they have been recycling), or a combination thereof. In some cases, purified mannitol, fructose, or other ingredients can be added as desired.

MIMOs

The maltosyl-isomaltooligosaccharides in the compositions described herein include glucose residues linked mostly by α-(1,6) linkages, and at least one maltose unit (e.g., at the reducing end) so that the final linkage is by an α-(1,4) bond. The maltosyl-isomaltooligosaccharides therefore terminate in a maltose unit. The majority of the linkages between the glucose units in the maltosyl-isomaltooligosaccharides in the compositions are α-(1,6) linkages, although some α-(1,2), α-(1,3), and α-(1,4) linkages can be present. Use of different types of fermentation organisms or different types of enzymes can produce MIMOs with different percentages of α-(1,2), α-(1,3), and α-(1,4) linkages. For example, dextransucrase from *L. mesenteroides* B-1299, can produce α-1,2 linked oligosaccharides with 30% or more. A product with a mixture of α-1,2 and α-1,6 linkages therefore can have branched maltosyl-isomaltooligosaccharides.

In some cases, the maltosyl-isomaltooligosaccharides can be linear oligosaccharides, with few branch points. However, the final MIMO product can include α-(1,2), α-(1,3), and α-(1,4) linkages as indicated above.

The mass average molecular weight distribution (MWD) of the MIMOs in the compositions described herein can vary depending upon the degree of polymerization (DP). For example, the maltosyl-isomaltooligosaccharides compositions can contain a mass average molecular weight distribution of about 504 to 1700 daltons, or of about 640 to 1700 daltons. In some cases, the maltosyl-isomaltooligosaccharides compositions contain a mass average molecular weight distribution of about 730 to 1400 daltons.

An example of an MIMO with a single maltosyl linkage [—O-α-(1,4)-] at the reducing end, and a DP of 5, can have the following chemical structure:

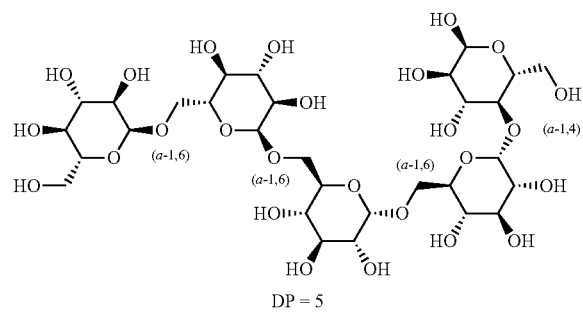 [SMILES: OC[C@H]1O[C@H](OC[C@H]2O[C@H](OC[C@H]3O[C@H](OC[C@H]4O[C@H](O[C@H]5[C@H](O)[C@@H](O)[C@@H](O)O[C@@H]5CO)[C@H](O)[C@@H](O)[C@@H]4O)[C@H](O)[C@@H](O)[C@@H]3O)[C@H](O)[C@@H](O)[C@@H]2O)[C@H](O)[C@@H](O)[C@@H]1O]

DP = 5

The MIMOs in the compositions described herein can have a number of glucose units. For example, the MIMOs in the compositions described herein can have from about 2 to about 18 glucose units, or about 2 to about 17 glucose units, or about 3 to about 16 glucose units, or about 3 to about 15 glucose units, or about 3 to about 14 glucose units, or about 3 to about 13 glucose units, or about 3 to about 12 glucose units. In general, the maltose-containing oligosaccharides have no more than about 17 glucose units, or no more than about 16 glucose units, or no more than about 15 glucose units, or no more than about 14 glucose units, or no more than about 13 glucose units, or no more than about 12 glucose units, or no more than about 11 glucose units, or no more than about 10 glucose units, for example, as detected by HPAEC-PAD or HPLC-RID or NMR.

As indicated, the MIMOs in the compositions described herein can have small numbers of α-(1,2), α-(1,3), and α-(1,4) glucosyl linkages. Hence, the MIMOs in the compositions described herein can have small numbers of branch points. For example, the MIMOs in the compositions described herein can have 0-4 branch points, or 0-3 branch points, or 0-2 branch points, or 0-1 branch points.

The compositions described herein can have a pH that is sufficiently low (1.5 to 2.8 pH, 1.5 to 4.2 pH, or 2.0 to 4.2 pH) to prevent microbiological spoilage and or pathogens while improving the organoleptic character of the composition. For example, the product pH can in some cases be pH 1-7, or pH 1-6, or pH 1-4, or pH 1-3, or pH 1.5-3.0, where a pH less than 3.3 (e.g., pH 1.5-2.8) is preferred.

In addition, the composition can in some cases be concentrated to a sufficiently high water activity (aW) to protect the shelf life.

Hence, in some cases, the low amounts of water and the low pH can protect the composition from spoilage or microbial growth.

A product of fermentation that contains maltosyl-isomaltooligosaccharides, dextransucrase/alternansucrase-producing microorganisms, and culture media can include MIMOs as well as some sugars, organic acids, organic acids, protein, color, odor, or combinations thereof. Such fermentation products can be subjected to downstream processing as described above to remove sugars, organic acids, protein, color, odor, or combinations thereof.

However, in some cases the final product can include one or more of the components from the fermentation process, including one or more of the original starting materials, or side-products made by the fermentation organism, such as organic acids, salts, flavor, odor, fructose, mannitol, etc. Examples include organic acids, salts, flavoring, odors, fructose, mannitol, and combinations thereof. In some cases, such components can provide desirable taste, organoleptic properties, or therapeutic products.

The MIMO products can have a distribution of lengths (degrees of polymerization, DP) over a range of DP values between two and nine with a mass-average molecular weight distribution in the range of 730-900 Da:

| Component: | Minimum %/brix: | Maximum %/brix: |
|---|---|---|
| maltose | 0.93 | 6.83 |
| MIMO-DP3 | 4.17 | 14.89 |
| MIMO-DP4 | 10.80 | 31.62 |
| MIMO-DP5 | 13.04 | 29.89 |
| MIMO-DP6 | 8.03 | 21.03 |
| MIMO-DP7 | 2.90 | 13.79 |
| MIMO-DP8 | 1.24 | 8.25 |
| MIMO-DP9 | 0.00 | 3.69 |

For example, a MWD of 780 Da 1.65% is commercially prepared, and thus preferred:

| Component: | Minimum %/brix: | Maximum %/brix: |
|---|---|---|
| maltose | 4.29 | 4.39 |
| MIMO-DP3 | 11.89 | 14.89 |
| MIMO-DP4 | 22.19 | 28.06 |
| MIMO-DP5 | 23.66 | 28.67 |
| MIMO-DP6 | 15.23 | 16.77 |
| MIMO-DP7 | 5.75 | 6.58 |
| MIMO-DP8 | 2.48 | 2.80 |
| MIMO-DP9 | 0.58 | 0.73 |

The concentration of the components in the final MIMO compositions can vary somewhat. However, the methods described herein efficiently remove mannitol, organic acids, salts, and other small molecules.

Hence, the amount of mannitol in the compositions can be 1%/brix mannitol or more, 2%/brix mannitol or more, 3%/brix mannitol or more, 4%/brix mannitol or more, 5%/brix mannitol or more, 6%/brix mannitol or more, 7%/brix mannitol or more, 8%/brix mannitol or more, 9%/brix mannitol or more, 10%/brix mannitol or more, 11%/brix mannitol or more, 12%/brix mannitol or more, 13%/brix mannitol or more, 14%/brix mannitol or more, 15%/brix mannitol or more, 17%/brix mannitol or more, 200%/brix mannitol or more, 22%/brix mannitol or more, 24%/brix mannitol or more, 26%/brix mannitol or more, 27%/brix mannitol or more, 28%/brix mannitol or more, 29%/brix mannitol or more, 30%/brix mannitol or more, 33%/brix mannitol or more, 35%/brix mannitol or more, or 40%/brix mannitol or more, or 1%/brix mannitol or less, 2%/brix mannitol or less, 3%/brix mannitol or less, 4%/brix mannitol or less, 5%/brix mannitol or less, 6%/brix mannitol or less, 7%/brix mannitol or less, 8%/brix mannitol or less, 9%/brix mannitol or less, 10%/brix mannitol or less, 11%/brix mannitol or less, 12%/brix mannitol or less, 13%/brix mannitol or less, 14%/brix mannitol or less, or 15%/brix mannitol or less.

In some cases, the amount of mannitol in the compositions can contain no mannitol.

Also as described above, the final MIMO product can contain 0%/brix fructose or more, 1%/brix fructose or more, 2%/brix fructose or more, 3%/brix fructose or more, 4%/brix fructose or more, 5%/brix fructose or more, 6%/brix fructose or more, or 7%/brix fructose or more, 9%/brix fructose or more, 10%/brix fructose or more, 15%/brix fructose or more, 20%/brix fructose or more, 30%/brix fructose or more, or 40%/brix fructose or more, or 1%/brix fructose or less, 2%/brix fructose or less, 3%/brix fructose or less, 4%/brix fructose or less, 5%/brix fructose or less, 6%/brix fructose or less, 7%/brix fructose or less, or 8%/brix fructose or less.

Treatment

The compositions described can be administered in a regimen that fosters the growth and/or activity of probiotic microorganisms that can be present in the digestive or gastrointestinal system of an animal. For example, the compositions described herein can be administered to animals, including humans, domesticated animals, zoo animals, and wild animals. The compositions can be used routinely or intermittently to foster the growth and/or activity of probiotic microorganisms that can be present in the digestive or gastrointestinal system of an animal.

The compositions contain an amount of MIMOs that can be effective for fostering the growth and/or activity of probiotic microorganisms. An effective amount can, for example, be an amount sufficient to foster probiotic microorganism growth by at least about 5%, 10%, 20%, 25%, 30%, 40%, 50%, 60%, 70%, 75%, 80%, 85%, 90%, 93%, 94%, 95%, 96%, 97%, 98%, 99%, 99.5%, or 99.9%. In some cases, the population of probiotic microorganisms can be increased in a gastrointestinal system of an animal who has received the compositions described herein. For example, the population of probiotic microorganisms can increase by about two-fold, or about three-fold, or about four-fold, or about five-fold, or about six-fold, or about seven-fold, or about ten-fold.

The compositions can be administered or ingested once a day, or twice a day, or three times a day. In some cases, the compositions can be administered or ingested every day for one week, or for one month, or for two months, or for three months, or for six months, or for one year, or for two years, or for three years. In many cases the compositions can be administered or ingested every day indefinitely. The compositions may be administered in single or divided dosages.

The compositions described herein can include a mixture of MIMOs as described herein. Inactive ingredients can be present in the compositions such a mannitol and some of the other components described herein. For example, the MIMOs can be present as about 50%, or about 60%, or about 65%, or about 70%, or about 75%, or about 80%, or about 85%, or about 90% or about 95%, or about 96%, or about 97%, or about 98%, or about 99% of the composition.

The compositions can be administered or ingested in amounts of at least about 0.01 mg/kg to about 100 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. For example, the compositions can be administered or ingested in amounts of at least about 0.1 g, or at least about 0.25 g, or at least about 0.5 g, or at least about 0.7 g, or at least about 0.8 g, or at least about 0.9 g, or at least about 1.0 g, or at least about 1.1 g, or at least about 1.2 g. The unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

The amount administered will vary depending on various factors including, but not limited to, what types of compound(s), and/or other therapeutic agents are administered, the route of administration, the progression or lack of progression of the disease, the weight, the physical condition, the health, the age of the patient, whether prevention or treatment is to be achieved, and if the antigen or ligand is chemically modified. Such factors can be readily determined by the clinician employing animal models or other test systems that are available in the art.

Compositions may be administered in a single dose, in multiple doses, in a continuous or intermittent manner, depending, for example, upon the recipient's physiological condition, whether the purpose of the administration is therapeutic or prophylactic, and other factors known to skilled practitioners. The administration of the compositions may be essentially continuous over a pre-selected period of time or may be in a series of spaced doses. Both local and systemic administration is contemplated.

In some cases, the compositions are formulated as liquid formulations. Alternatively, the MIMOs and other ingredients may be in powder form, obtained by aseptic isolation of sterile solid or by lyophilization from solution. Such powder forms can be re-constituted as liquids with a suitable vehicle, e.g., sterile, pyrogen-free water, before use.

When the MIMOs are prepared for oral administration, they can be combined with a carrier. Such a carrier can be a pharmaceutically acceptable carrier, diluent or excipient. The compositions can be provided in the form of a unit dosage form. For oral administration, the MIMOs may be present as a powder, a granular formulation, a solution, a suspension, an emulsion or in a natural or synthetic polymer or resin for ingestion of the active ingredients from a chewing gum. The therapeutic agents may also be presented as a bolus, electuary or paste.

In some case, the compositions can be prepared for, and administered as, oral compositions. For example, tablets or caplets containing the compounds, and optionally a carrier can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, maltodextrin, sodium lauryl sulfate, starch, talc, and titanium dioxide, and the like, as well as liquid vehicles such as polyethylene glycols (PEGs) and vegetable oil. Moreover, enteric-coated caplets or tablets containing one or more of the compounds of the invention are designed to resist disintegration in the stomach and dissolve in the more neutral to alkaline environment of the duodenum or all the way to the colon.

The compositions can also include antioxidants, surfactants, preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

The subjects to whom the compositions can be subjects that may have one or more diseases or conditions. Examples of diseases or conditions can include cancer, pre-cancerous condition(s) or cancerous propensities, diabetes (e.g., type 2 diabetes, or type 1 diabetes), autoimmune disease(s), acid reflux/GERD, vitamin deficiencies, mood disorder(s), degraded mucosal lining(s), ulcerative colitis, digestive irregularities (e.g., Irritable Bowel Syndrome, acid reflux/GERD, constipation, diarrhea, alternating constipation and diarrhea, or any combination thereof), inflammatory bowel disease, ulcerative colitis, Crohn's disease, gastroesophageal reflux disease (GERD), infectious enteritis, antibiotic-associated diarrhea, diarrhea, colitis, colon polyps, familial polyposis syndrome, Gardner's Syndrome, *Helicobacter pylori* infection, irritable bowel syndrome, and intestinal cancers. The compositions can foster the growth and activity of certain types of bacteria (e.g., *L. lactis* strains) leads to the production of various types of bacteriocins (e.g., nisins) that can act as anti-cancer agents and/or as anti-microbial agents. For example, early studies indicate that the compositions described herein can reduce or eliminate symptoms in 81% of users who self-identified as having acid reflux symptoms once a week or more.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present application, the preferred methods and materials are now described.

As utilized in accordance with the present disclosure, the following terms, unless otherwise indicated, shall be understood to have the following meanings:

"Brix", also known as degrees Brix (symbol ° Bx), refers to the sugar content of an aqueous solution. One degree Brix is 1 gram of sucrose in 100 grams of solution and represents the strength of the solution as percentage by weight (% w/w). Brix also accounts for dissolved salts, organic acids, and other solutes that increase the refractive index of the solution. As such, it is less useful as a quantitative measure of saccharide content in complex broth (fermentation mixtures) but is quite accurate with respect to the refined product. Thus, 1 degree brix=1 g refractive dry solids per 100 g of material. If the solution contains dissolved solids other than pure sucrose, then the ° Bx only approximates the dissolved solid content. However, when the constituent components of the compositions to be compared are similar and/or within similar ranges, Brix values are reproducible and provide an approximation which, in this case, is an accurate (relative to true dry solids via evaporation) measurement of relative dry solids per each composition.

"Optical density" or "OD" refers to an estimation of cellular density in a fermentation. Typically used to determine the progress of a fermentation, it is determined via absorbance of light at 600 nm and may be referenced to dry cell mass.

"HPAEC-PAD" refers to a hyphenated instrumental analytical technique known as High Pressure Anion Exchange (HPAEC) liquid chromatography (ThermoDionex ICS-5000+) with a Pulsed Amperometric Detector (PAD). Under the scope of this work, this instrument is used solely for the high-resolution separation (ThermoDionex Carbopac PA-100, pH >12.5, acetate gradient elution) of sugar alcohols, mono and disaccharides, and oligosaccharides. Quantification is done via internal standard using L-arabinose and response factors relative to either the pure compound or to a purified maltodextrin of equivalent molecular weight.

"HPLC-RID" refers to a hyphenated instrumental analytical technique known as High Pressure Liquid Chromatography (HPLC, Agilent 1100) with a Refractive Index Detector (RID). Under the scope of this work, this instrument is used to separate (BioRad Aminex HPX-87H, 0.008N $H_2SO_4$ isocratic) and quantify organic (carboxylic) acids that result from bacterial fermentation. This instrument is also used to confirm DP 3, maltose, and mannitol. Quantification is done via external standard method vs. a mixed standard made from target compounds of known purity.

"SIP" refers to sterilized in place.

"SBF" refers to sterilization by filtration through a 0.2 μm membrane.

"CIP" refers to cleaned in place.

"DSP" refers to downstream processing.

"PRMXE" refers to filter cartridge series PRMXE or "Pur-Maxx E" dual-layer pleated polyethersulfone membrane sterilizing grade (SG) cartridges; 0.20 μm.

"Degree of polymerization", or "DP", refers to the number of monosaccharide sugar units in a given oligosaccharide.

"Oligosaccharides" refers to glycans of all kinds with DP>=3 and <=10.

"Molecular weight distribution," or "MWD" refers to the mass-average molecular weight of a distribution of oligosaccharides.

"Oligosaccharides" refers to glycans of all kinds, generally with a degree of polymerization (DP) greater than or equal to 3 and less than or equal to 18.

"SAC" means a Strong Acid Cation exchange resin, typically one with sulfonic acid groups, i.e., a sulfuric acid equivalent. In some instances, SAC is referring to Purolite C-150S, which has a $H^+$ capacity of 1.8 mol/L.

"WBA" means a Weak Base Anion exchange resin, typically one with tertiary amine groups, which are not stronger than the corresponding free base (pKa ~9.8). In this case, WBA is referring to Purolite A-133 which has a free-base capacity of 1.8 mol/L.

The Examples illustrate some of the experimental work performed in the development of the invention.

Example 1: MIMO Products Used in Clinical Trials

Two variations of product were used in clinical trials. They varied only in molecular weight distribution, and this was controlled by varying the sucrose to maltose ratio (S/M). "A2"-type products have a molecular weight of about 750 Da and "Classic" or "NC"-type products have a molecular weight of about 800 Da. Each of the two types were a composite of six 16 kg fermentations each of A2 and NC types (12 total fermentations). The clinical trials were both double-blind placebo-controlled studies, and the parameters for each are given here.

First Clinical Trial Protocol

Purpose: To compare the effects of daily intake of two different formulations of the ISOThrive supplement vs. a placebo on the primary outcome measure of body weight and secondary outcome measures (inflammatory and satiety serum markers, hunger/satiety, health-related measures and self-reported quality of life) in a group of overweight but otherwise healthy adults.

Study design: A randomized, placebo controlled, double-blind parallel design control trial to compare the effects of daily intake for a 3-month period of the ISOThrive supplement vs. a placebo.

The study design included 3 treatment arms:
(1) ISOThrive supplement (Type 1, "A2")
(2) ISOThrive supplement (Type 2, "NC")
(3) Placebo supplement (high-maltose syrup at 64 brix)

The two ISOThrive supplements (Type I and 2) have essentially the same active ingredients, and similar dosages of 1000 mg of MIMO. The two types of the supplement differ in terms of purity (MIMO/total) and the mass-average molecular weight distribution of the MIMO, which is the principal ingredient.

Study participants included 105 overweight men and women in the age range of 18 to 75 years, who are nonsmokers with a body mass index (BMI) > or =25 and a maximum body weight of 350 pounds.

Second Clinical Trial Protocol

Purpose: First, to evaluate, via 16S rRNA sequencing of fecal swabs, the effect of a nutritional supplement (specific soluble fiber known as isomalto-oligosaccharides) on the abundance, diversity, and predicted microbiome gene function, of gut bacteria. Second, to evaluate the overall subject condition in terms of body weight, and self-reported gut health data. The test groups were compared across-supplement and with the placebo group.

Study Design: a randomized, placebo-controlled trial, with a dose escalation at the mid-point of the intervention period.

Subjects were between the ages of 18 and 45 years, with a maximum weight of 350 lbs., and a body mass index 25 kg/m² or higher and had general self-reported good health.

Sixty subjects were randomized to three arms (20 each: Supplement type-1, Supplement formula type-2, or placebo) took a daily dose of either Supplement A, Supplement B, or placebo for 8 weeks.

Doses included 500 mg of MIMO during the first 4 weeks and then included 1000 mg of MIMO for a second 4 weeks.

Composition for Clinical Trials: "A2" and "Classic" Type Products

Six fermentations were carried out to generate each type of product using a 20 L fermenter (New Brunswick BioFlo 410). The two types of fermentations were initiated by charging the following media into different vessels as described in Table 2.

TABLE 2

A2 and Classic Media

"A2" Type

| N = 6 | Kg: | Stdev: | RSD, %: |
|---|---|---|---|
| Water | 12.594 | 0.0144 | 0.114 |
| Sucrose | 1.800 | 0.0000 | 0.000 |
| Maltose-H$_2$O | 0.998 | 0.0000 | 0.000 |
| MnSO$_4$—H$_2$O | 0.0002 | 0.0000 | 1.000 |
| MgSO$_4$ | 0.0015 | 0.0000 | 0.209 |
| FeSO$_4$—7H$_2$O | 0.0002 | 0.0000 | 1.454 |
| KH$_2$PO$_4$ | 0.0400 | 0.0000 | 0.014 |
| NaCl | 0.0002 | 0.0000 | 0.824 |
| CaCl$_2$—2H$_2$O | 0.0008 | 0.0000 | 0.390 |
| Yeast Extract | 0.075 | 0.0004 | 0.543 |
| NaOH, 50% | 0.016 | 0.0003 | 2.056 |
| Total: | 15.53 | 0.040 | 0.25 |
| TS, %: | 17.38 | 0.042 | 0.24 |
| Brix, %: | 18.19 | 0.031 | 0.17 |
| S/M: | 2.00 | 0.000 | 0.00 |

TABLE 2-continued

A2 and Classic Media

"Classic" Type

| N = 6 | Kg: | Stdev: | RSD, %: |
|---|---|---|---|
| Water | 12.600 | 0.0004 | 0.003 |
| Sucrose | 1.910 | 0.0004 | 0.021 |
| Maltose-H$_2$O | 0.864 | 0.0000 | 0.000 |
| MnSO$_4$—H$_2$O | 0.0002 | 0.0000 | 1.610 |
| MgSO$_4$ | 0.0015 | 0.0000 | 0.281 |
| FeSO$_4$—7H$_2$O | 0.0002 | 0.0000 | 0.801 |
| KH$_2$PO$_4$ | 0.0400 | 0.0000 | 0.076 |
| NaCl | 0.0002 | 0.0000 | 1.058 |
| CaCl$_2$—2H$_2$O | 0.001 | 0.0000 | 1.479 |
| Yeast Extract | 0.076 | 0.0008 | 1.108 |
| NaOH, 50% | 0.016 | 0.0007 | 4.379 |
| Total: | 15.51 | 0.0232 | 0.15 |
| TS, %: | 17.33 | 0.0259 | 0.15 |
| Brix, %: | 18.15 | 0.0313 | 0.17 |
| S/M: | 2.45 | 0.0005 | 0.02 |

The pH of the media was adjusted to 7.00 with NaOH (50%).

200 mL of each type of medium was transferred to an Erlenmeyer flask, sealed and autoclaved at 121° C. for 15 minutes, cooled, and inoculated with 1 mL vial stock (0.5 mL late-log culture in 20% glycerol, stored at −75° C.). The seed was incubated with swirling at 27° C. and allowed to grow for about 16 hr. The balance of each type of medium was transferred to a fermenter via sanitary pump. The fermenters were sealed and sterilized in place (SIP) to 116° C., then rapidly cooled to 30° C. (see temperature curve in FIG. 8). The curve was modeled, and the model was used to determine the time spent in each microbiologically relevant regime. The results are shown in Table 3.

TABLE 3

Thermal Time Course

| T ° C.: | Hr: |
|---|---|
| >70 | 2.43 |
| >80 | 2.22 |
| >90 | 1.86 |
| >100 | 1.16 |
| >110 | 0.46 |

These results are relevant because when the full media is mixed and adjusted to pH 7.00 (to avoid inversion of sucrose) significant amounts of maltose (a reducing sugar) are lost via the Maillard reaction. In addition to generating a great deal of colored material (>10,000 IU), this increases the S/M of the medium (as detected by HPLC-RID) and has the effect of increasing the ultimate molecular weight distribution of the product.

The fermenter was inoculated with 150 mL of the flask seed culture containing *Leuconostoc citreum* ATCC 13146 (NRRL B-742) and the pH of the medium was corrected to 6.50 using a solution of 37% HCl. The fermentation was allowed to proceed for 55 Hr with pH adjustment using a solution of 40% NaOH to maintain the pH at 5.50.

Typically, there is a 4-6 hour induction period, or lag-phase, preceding log-growth. The log-growth phase is about 10 hours (where most growth occurs) but it typically takes about 18 hours to reach stationary growth. A pH of 5.5 is typically achieved within about 2 hours of log-phase growth, and this pH is maintained thereafter. This pH was chosen per the experimentally determined pH optimum for the dextran-sucrase enzyme.

The fermentations consumed 450±29.3 and 468±22.3 g 40% NaOH for the A2 and NC type batches, respectively.

Figure 9:
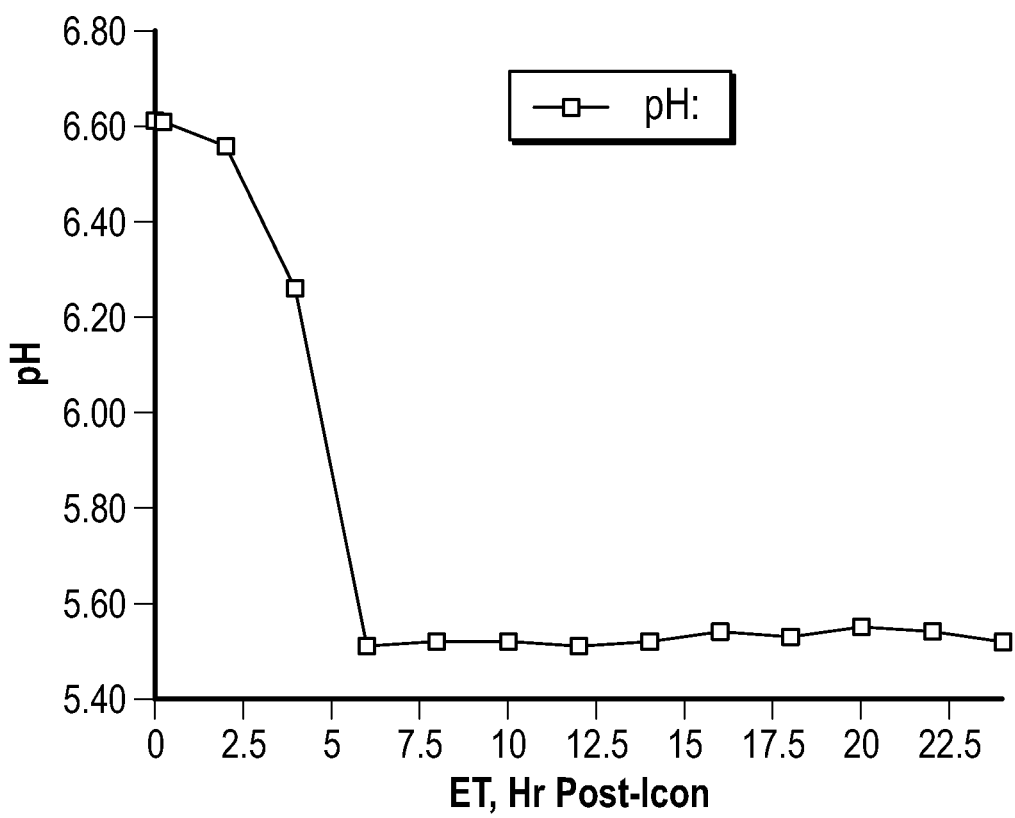
FIG. 9 shows the behavior of fermentation pH during the course of a 14 L fermentation with *Leuconostoc citreum* ATCC 13146 with the designation NRRL B-742. Note onset of pH control with NaOH (40% w/w) to maintain a pH of 5.50 at approximately 6 hours into log-growth phase.

FIG. 9 graphically illustrates the typical behavior of the pH during fermentation after inoculation.

Figure 10:
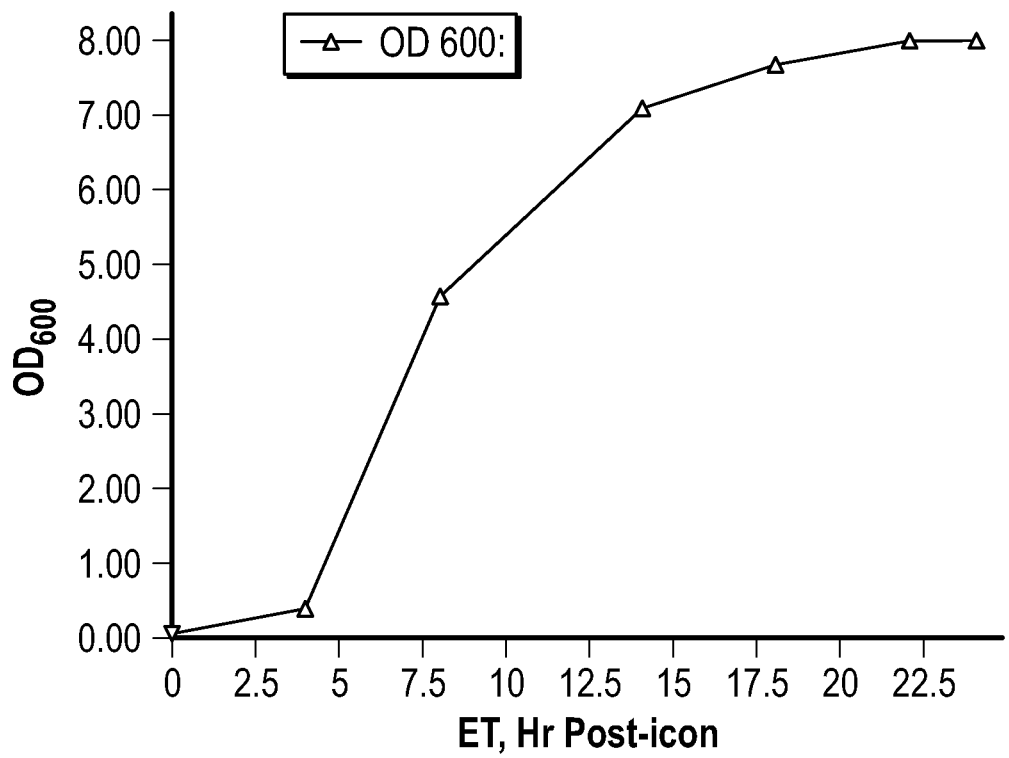
FIG. 10 shows the progress of fermentation via optical density (OD) through log-phase growth of a 14 L fermentation with *L. citreum* NRRL B-742.

The growth curve (onset and log-phase) was determined by optical density at 600 nm ($OD_{600}$) and is shown in FIG. 10.

The completion of fermentation was indicated by consumption of fructose, which was converted to mannitol, and by cessation of the take up of alkali. Upon completion, the fermentation was harvested, and the cells removed via centrifugation (Sorvall RC-5B Plus, G3 rotor, 13,689 g for 20 min at 5-10° C.). The broth was concentrated by evaporation (Buchi R-20 rotavap, 70° C. bath, 54° C. vapor at 26" Hg) to 40 brix and decolorized by treatment with 250 g of Carbochem CA-50S powdered activated carbon (PAC) while still hot (50-65° C.). The slurry was stirred for 20 minutes and vacuum-filtered (using a 2×240 mm Buchner funnel, 2 L side-arm flask, Whatman #3 filter papers and a 100 g Celite 545 pre-coat). The powdered activated carbon cakes were washed with 3×250 mL water each, and the whole wash was collected.

The minerals/salts (primarily sodium) and organic acid metabolites (primarily lactic and acetic acids) were removed in a sequential two-stage ion exchange process. First, the decolorized concentrate, typically 6-7 kg at 32-36° Bx, is passed through 6.8 L strong acid cation exchange resin (Purolite C-150S) to remove the minerals/salts. Then, the de-ashed broth is passed through 14.7 L weak base anion exchange resin (Purolite A-133) to remove the organic acids. The de-ashed liquor is then concentrated by evaporation to 56.78 brix.

The liquor (about 56 brix) is transferred hot into a 2.5 gal crystallization vessel and allowed to slowly cool to room temperature (19-22° C.) and crystallize overnight.

The resulting mixture is homogenized to yield a pourable crystal slurry. The mannitol crystals can be separated out via basket centrifuge (Robitel RA 20 VX with a 10 μm polypropylene filter bag).

A small portion of the crystal cake (0.320 kg at 95% solids, cake #1) can be washed with 500 mL ice-cold deionized water, and a 0.697 kg cake wash (wash #1) at 20.5 brix can be retained for recycle while a 2.626 kg liquor (liquor #1) at 51.70 brix can be refrigerated to 3° C. to crystallize overnight.

Another portion of the crystals (cake #2, 0.109 kg at 95% solids) can be removed, and washed as before. The cake wash #2 can be combined with wash #1 for recycle. The product liquor #2 at 49.0 brix can be analyzed (HPAEC-PAD, HPLC-RID, brix, pH and conductivity) and refrigerated pending compositing with like (either A2 or Classic) batches. Once combined the whole composite can be evaporated to 65-67 brix prior to analytics for the final certificate of analysis and pack out into trial dosage forms. The packaging is performed in a sterilized laminar flow-hood where 32 g amounts (for example) can be packed by volume (24.16 mL), as confirmed by lot mass, in autoclaved CRGXTA-loz amber glass ovals (Berry Plastics Corporation) with autoclaved 20 mm SealSafe Penetrex adapter-plug seals for dose metering via luer-tip plastic syringe (Andwin Scientific, #760020G).

Analytical Results and Reproducibility

The following tables illustrate the composition and reproducibility of batches manufactured using the A2 and New Classic media.

TABLE 4A

A2 Type Product

| | Batch | | | | | | A2 |
| --- | --- | --- | --- | --- | --- | --- | --- |
| | 021815 | 022315 | 022615 | 030215 | 033015 | 040915 | Comp. |
| S/M: | 2.00 | 2.00 | 2.00 | 2.00 | 2.00 | 2.00 | 2.00 |
| DP 1, %/bx: | 2.60 | 1.26 | 1.67 | 1.36 | 0.59 | 1.80 | 1.51 |
| DP 2, %/bx: | 6.48 | 2.92 | 2.71 | 9.46 | 5.35 | 8.17 | 6.54 |
| MIMO, %/bx: | 74.89 | 77.57 | 76.02 | 80.00 | 73.94 | 71.94 | 76.53 |
| Mannitol, %/bx: | 11.17 | 10.59 | 10.87 | 10.03 | 11.08 | 12.11 | 10.42 |
| Lactate, %/bx: | 0.00 | 0.00 | 0.12 | 0.00 | 0.26 | 0.00 | 0.00 |
| Formate, %/bx: | 0.00 | 0.00 | 0.00 | 0.00 | 0.00 | 0.00 | 0.00 |
| Acetate, %/bx | 0.00 | 0.00 | 0.06 | 0.00 | 0.10 | 0.00 | 0.00 |
| Glycerol, %/bx: | 1.48 | 1.44 | 1.60 | 1.55 | 1.39 | 1.45 | 1.47 |
| TOTAL, %/bx: | 96.62 | 93.78 | 93.05 | 102.41 | 92.71 | 95.48 | 96.48 |
| PURITY: | 77.51 | 82.71 | 81.70 | 78.12 | 79.75 | 75.35 | 79.33 |
| MWD, Da: | 746.89 | 758.02 | 777.60 | 748.74 | 762.34 | 746.75 | 760.37 |
| Brix, %: | 50.51 | 49.00 | 53.76 | 54.93 | 51.32 | 47.39 | 67.27 |
| μS/cm: | 10.53 | 12.8 | 15.65 | 15.19 | 2260 | 364 | 260 |
| pH: | 4.9 | 4.59 | 3.45 | 5.28 | 5.82 | 6.91 | 4.47 |

TABLE 4B

"New Classic" or "NC"-type product

| | Batch | | | | | | NC |
| --- | --- | --- | --- | --- | --- | --- | --- |
| | 012015 | 031015 | 032015 | 032315 | 032515 | 040215 | Comp |
| S/M: | 2.33 | 2.33 | 2.33 | 2.33 | 2.33 | 2.33 | 2.33 |
| DP 1, %/bx: | 2.73 | 2.08 | 1.10 | 1.14 | 1.87 | 1.38 | 1.95 |
| DP 2, %/bx: | 5.54 | 6.96 | 5.93 | 1.96 | 5.47 | 5.06 | 1.73 |

TABLE 4B-continued

"New Classic" or "NC"-type product

| | Batch | | | | | | NC Comp |
|---|---|---|---|---|---|---|---|
| | 012015 | 031015 | 032015 | 032315 | 032515 | 040215 | |
| MIMO, %/bx: | 71.88 | 71.22 | 73.63 | 74.59 | 69.79 | 76.19 | 72.61 |
| Mannitol, %/bx: | 13.25 | 10.94 | 10.83 | 12.36 | 12.27 | 10.63 | 11.97 |
| Lactate, %/bx: | 0.000 | 0.000 | 0.000 | 0.000 | 0.969 | 0.20 | 0.30 |
| Formate, %/bx: | 0.000 | 0.000 | 0.000 | 0.000 | 0.405 | 0.00 | 0.27 |
| Acetate, %/bx: | 0.033 | 0.000 | 0.000 | 0.000 | 0.364 | 0.05 | 0.12 |
| Glycerol, %/bx: | 1.558 | 2.269 | 1.562 | 1.562 | 1.990 | 1.58 | 1.76 |
| TOTAL, %/bx: | 94.99 | 93.47 | 93.04 | 91.61 | 93.13 | 95.10 | 90.72 |
| PURITY: | 75.68 | 76.20 | 79.13 | 81.42 | 74.94 | 80.12 | 80.05 |
| MWD, Da: | 817.69 | 808.88 | 804.03 | 820.12 | 811.74 | 806.52 | 834.69 |
| Brix, %: | 49.06 | 52.16 | 46.44 | 50.08 | 51.23 | 50.54 | 65.07 |
| µS/cm: | 239 | 279 | 43.2 | 350 | 2070 | 1415 | 410 |
| pH: | 6.82 | 6.43 | 6.69 | 7.13 | 6.83 | 6.94 | 5.12 |

Note that the products produced using A2 and New Classic (NC) media have substantial amounts of mannitol, as well as some glycerol and organic acids. Note also that the DP 1 = glucose + fructose and DP 2 = sucrose + maltose, where the amounts of these sugars in the A2 and NC products were as follows.

TABLE 5

Sugar Content of A2 and New Classic Batches

| A2, %/brix | 021815DA | 022315DA | 022615DA | 030215DA | 033015DA | 040915DA | A2 Comp. |
|---|---|---|---|---|---|---|---|
| Glucose | 2.27 | 1.11 | 1.46 | 1.26 | 0.56 | 1.69 | 1.41 |
| Fructose | 0.32 | 0.15 | 0.21 | 0.10 | 0.03 | 0.12 | 0.10 |
| Sucrose | 0.71 | 0.69 | 0.90 | 3.81 | 0.68 | 1.34 | 0.87 |
| Maltose | 5.77 | 2.23 | 1.82 | 5.65 | 4.67 | 6.83 | 5.68 |

| NC, %/brix | 012015DA | 031015DA | 032015DA | 032315DA | 032515DA | 040215DA | NC Comp |
|---|---|---|---|---|---|---|---|
| Glucose | 2.42 | 1.94 | 1.05 | 0.99 | 1.79 | 1.36 | 1.67 |
| Fructose | 0.30 | 0.14 | 0.04 | 0.15 | 0.09 | 0.02 | 0.27 |
| Sucrose | 0.75 | 1.52 | 1.25 | 0.27 | 1.09 | 0.70 | 0.36 |
| Maltose | 4.79 | 5.44 | 4.68 | 1.69 | 4.38 | 4.36 | 1.37 |

The MIMO products generated by the foregoing methods had a reproducible distribution of DPs from 3-9 that varied according to S/M present at the start of fermentation. Mean amounts of the MIMOs are shown in Table 6.

TABLE 6

Degree of Polymerization for Products of A2 and New Classic Media

| N = 6 each | A2, mean: | STDEV: | RSD, %: | NC, mean: | STDEV: | RSD, %: |
|---|---|---|---|---|---|---|
| MIMO-DP3 | 12.522 | 1.003 | 8.007 | 8.88 | 0.50 | 5.61 |
| MIMO-DP4 | 23.510 | 1.173 | 4.991 | 17.46 | 1.00 | 5.75 |
| MIMO-DP5 | 23.357 | 0.685 | 2.931 | 22.59 | 1.38 | 6.12 |
| MIMO-DP6 | 10.888 | 0.423 | 3.883 | 13.73 | 0.28 | 2.06 |
| MIMO-DP7 | 3.280 | 0.181 | 5.515 | 5.09 | 0.38 | 7.52 |
| MIMO-DP8 | 2.251 | 0.229 | 10.167 | 3.96 | 0.41 | 10.35 |
| MIMO-DP9 | 0.683 | 0.047 | 6.933 | 1.14 | 0.17 | 14.53 |

Example 2

After performing the processes described in Example 1, it was observed that mannitol would crystallize from the final products upon refrigeration or long-term storage at cooler room temperature. This example illustrates the variability in product composition relative to the crystallization process employed. Additionally, the batch generated as described in this Example was used to test the effect of sterilization (or steam) in place on sucrose:maltose ratio.

Improved Composition via Manipulation of Crystallization Parameters

To a 20 L fermenter (New Brunswick BioFlo 410) was added media with the following composition.

TABLE 7

Medium Employed

| Batch: 051315 | kg: | g: |
|---|---|---|
| Water | 12.600 | |
| Sucrose | 1.800 | |
| Maltose-$H_2O$ | 0.998 | |
| $MnSO_4$—$H_2O$ | 0.00015 | 0.15083 |
| $MgSO_4$ | 0.00146 | 1.46045 |
| $FeSO_4$—$7H_2O$ | 0.00015 | 0.14997 |
| $KH_2PO_4$ | 0.04000 | 40.00375 |
| NaCl | 0.00015 | 0.14985 |
| $CaCl_2$—$2H_2O$ | 0.00080 | 0.80170 |
| Yeast Extract | 0.077 | |
| NaOH, 50% | 0.017 | 16.68234 |
| Total: | 15.534 | |
| TS, %: | 17.374 | |
| Brix, %: | 18.198 | |
| S/M: | 2.00 | |

The pH of the medium was adjusted to 7.00 with NaOH (50%) and the sterilized medium (pre-inoculation) was sampled for analysis of S/M via HPLC-RID. 200 mL of the medium was transferred to an Erlenmeyer flask, the flask was then sealed and autoclaved at 121° C. for 15 minutes. The medium was cooled and inoculated with 1 mL vial stock (0.5 mL late-log culture Leuconostoc citreum ATCC 13146, NRRL B-742, in 20% glycerol, stored at −75° C.). The seed was incubated with swirling at 27° C. and allowed to grow for 16 Hr.

The balance of the medium was transferred to the fermenter via sanitary pump. The fermenter was sealed and sterilized in place (SIP) to 116° C., as previously described in Example 1. The fermenter was inoculated with 150 mL of the flask seed culture and the pH of the medium was corrected to 6.50 using 37% HCl. Fermentation was allowed to proceed for 55 Hr with pH adjustment with 40% NaOH (40%) to maintain 5.50.

Typically, there is a 6-hour induction period preceding log-growth. Log-growth typically proceeded for approximately 10 hours. A pH 5.5 was typically achieved within about 2 hours of log-phase growth, and this pH is maintained thereafter.

The fermentation consumed 464 g of 40% NaOH.

The completion of fermentation was indicated by consumption of fructose, which was converted to mannitol, and by cessation of the take up of alkali. The fermentation was harvested, and the cells removed via centrifugation (Sorvall RC-5B Plus, G3 rotor, 13,689 g for 20 min at 5-10° C.). The broth was concentrated by evaporation (Buchi R-20 rotavap, 70° C. bath, 54° C. vapor @ 26" Hg) to 40 brix and decolorized by treatment with 266 g of powdered activated carbon (PAC Carbochem CA-50S) while still hot (50-65° C.). The slurry was stirred for 20 minutes and vacuum-filtered (2×240 mm Buchner funnel, 2 L side-arm flask, Whatman #3 filter papers and a 100 g Celite 545 pre-coat). The PAC cakes were washed with 3×250 mL water each, and the whole collected.

The minerals/salts (primarily sodium) and organic acid metabolites (primarily lactic and acetic acids) were removed in a sequential two-stage ion exchange process. First 6.236 kg of broth at 35.5 brix was passed through 6.8 L strong acid cation exchange resin (Purolite C-150S) to remove the minerals/salts. Then, the de-ashed broth is passed through 14.7 L weak base anion (Purolite A-133) to remove the organic acids. The pH of the de-ashed liquor was adjusted to 6.16 (from 10.80) with HCl (37%) and concentrated by evaporation to 57.01 brix. The de-ashed concentrate was transferred hot into a 2.5 gal crystallization vessel and allowed to slowly cool to room temperature (19-22° C.) and crystallize overnight.

The resulting mixture was homogenized to yield a pourable crystal slurry. The mannitol crystals were separated via basket centrifuge (Robitel RA 20 VX with a 10 μm polypropylene filter bag).

A small portion of the crystal cake (0.279 kg at 95% solids, cake #1) was washed with 500 mL ice-cold deionized water, and a 0.672 kg cake wash (wash #1) at 18.7 brix was retained for recycle while 2.403 kg of liquor (liquor #1) at 52.56 brix was collected.

Liquor #1 was concentrated by evaporation to 65.68 brix. The resulting concentrate was split into two portions. The first portion (0.921 kg) was crystallized again at room temperature (19-22° C.). The second portion was crystallized to a temperature of approximately 2° C. Both crystallizations were allowed to proceed overnight.

The room temperature crystals (cake #2RT, 0.039 kg at 95% solids) were removed, as described above. The cake wash #2RT (0.552 kg) was combined with wash #1 for recycle.

The refrigerated crystals (cake #2RC, 0.094 kg at 95% solids) were removed, as before. The cake wash #2RC (0.626 kg) was combined with wash #1 for recycle.

The product liquors #2RT at 64.08 brix and #2RC at 63.82 brix were analyzed via (HPAEC-PAD, HPLC-RID, brix, pH and conductivity).

Results

HPLC-RID determined that the pre-inoculated sucrose/maltose ratio had increased from 2.00 to 2.73 after sterilization as illustrated in Table 8.

TABLE 8

Effect on Sugar Content of Sterilization

| Compound: | %/brix Pre SIP | %/brix Post SIP |
|---|---|---|
| Sucrose | 62.26 | 61.14 |
| Maltose | 31.31 | 22.38 |
| Glucose | 0.27 | 4.61 |
| fructose | 0.00 | 0.15 |
| Total: | 93.84 | 88.28 |
| S/M: | 1.99 | 2.73 |

The composition of the products produced as described in this Example after cold temperature and room temperature second crystallization are shown in Table 9.

TABLE 9

Product Composition after Crystallization at Two Temperatures

| Cold 2nd Xl, T ° C.: | 2 | | Room Temp 2nd Xl, T ° C.: | 20 | |
|---|---|---|---|---|---|
| Component | %/brix: | % w/w: | Component | %/brix: | % w/w: |
| Glucose | 0.79 | 0.50 | Glucose | 0.76 | 0.49 |
| Fructose | 0.03 | 0.02 | Fructose | 0.02 | 0.02 |
| Sucrose | 1.76 | 1.12 | Sucrose | 1.62 | 1.04 |
| Maltose | 4.93 | 3.15 | Maltose | 4.84 | 3.10 |
| MIMO | 89.08 | 56.85 | MIMO | 87.75 | 56.23 |
| Mannitol | 8.82 | 5.63 | Mannitol | 11.20 | 7.18 |
| Lactate | 0.33 | 0.21 | Lactate | 0.32 | 0.20 |
| Glycerol | 0.38 | 0.24 | Glycerol | 0.37 | 0.24 |
| Formate | 0.00 | 0.00 | Formate | 0.00 | 0.00 |
| Acetate | 0.13 | 0.09 | Acetate | 0.11 | 0.07 |
| TOTAL: | 106.25 | 67.81 | TOTAL: | 106.99 | 68.56 |
| Brix, %: | 63.82 | | Brix, %: | 64.08 | |
| Purity, %: | 83.84 | | Purity, %: | 82.02 | |
| Mw, Da: | 737 | | Mw, Da: | 739 | |
| MIMO DP | %/brix: | | MIMO DP | %/brix: | |
| MIMO-DP3 | 13.84 | | MIMO-DP3 | 13.71 | |
| MIMO-DP4 | 31.62 | | MIMO-DP4 | 30.82 | |
| MIMO-DP5 | 27.75 | | MIMO-DP5 | 27.30 | |
| MIMO-DP6 | 11.50 | | MIMO-DP6 | 11.48 | |
| MIMO-DP7 | 3.11 | | MIMO-DP7 | 3.19 | |
| MIMO-DP8 | 1.26 | | MIMO-DP8 | 1.25 | |
| MIMO-DP9 | 0.00 | | MIMO-DP9 | 0.00 | |

Thus, for batches made via cold filter sterilization of the sugars, a sucrose/maltose ratio of 2.73 provides a MWD, for example, of about 740 to 790 Da.

Increasing the brix of liquor #1 to greater than 65 and cooling the second crystallization to 2-5° C. improved the purity of the product (relative to room temperature crystallization of either 52 or 65.78 brix) by approximately 26% (−3.15%/brix). The final product so obtained demonstrated improved shelf stability and did not crystallize further once stored at either 5 or 20° C.

This process-iteration (concentration of liquor #1 and sequential crystallization, first to room temperature and then to 2-5° C.) therefore removes some of the mannitol but such crystallization procedures are not readily automated and do not remove small molecules very efficiently.

Example 3

This Example demonstrates the fermentation at 10 L scale, using a sucrose:maltose ratio of 2.00 at time of inoculation, and with introduction of sugars via filtration through a 0.2 mm filter (sterilized by filtration, SBF).

10 L Trial Fermentation at S/M=2.0 with SBF of Sugars

A sugar and salt stock solution was prepared with the composition shown in Table 10.

TABLE 10

Sugar and Salt Stock Solution

| 10 L #1 | kg: |
|---|---|
| Water | 4.471 |
| Sucrose | 1.430 |
| Maltose-H$_2$O | 0.795 |
| NaCl | 0.00012 |
| CaCl$_2$—2H$_2$O | 0.00064 |
| Total: | 6.698 |

TABLE 10-continued

Sugar and Salt Stock Solution

| 10 L #1 | kg: |
|---|---|
| TS, %: | 32.05 |
| Brix, %: | 32.06 |
| S/M: | 1.990 |

The components shown in Table 11 were added to a 10 L fermenter (BioFlo 410 or equivalent).

TABLE 11

Initial Components Added to Fermenter (10 liter)

| 10 L #1 | SIP kg: |
|---|---|
| Water | 4.500 |
| MnSO$_4$—H$_2$O | 0.000098 |
| MgSO$_4$ | 0.000951 |
| FeSO$_4$—7H$_2$O | 0.000098 |
| KH$_2$PO$_4$ | 0.02606 |
| Yeast Extract | 0.04887 |
| Total: | 4.576 |
| TS, %: | 0.00 |
| Brix, %: | 1.66 |
| S/M: | n/a |

This mixture was sterilized in place (within the fermenter) at 121° C. for 30 minutes then cooled to room temperature, and 5.4697 kg of the sugar and salt stock solution was transferred (SBF) into the fermenter via 0.2 μm filter to give a pre-inoculation (sampled for analysis) medium with the composition shown in Table 12.

TABLE 12

Pre-Inoculation Medium

| 10 L #1 | Total kg: |
|---|---|
| Water | 8.402 |
| Sucrose | 1.168 |
| Maltose-H$_2$O | 0.650 |
| MnSO$_4$—H$_2$O | 0.000 |
| MgSO$_4$ | 0.001 |
| FeSO$_4$—7H$_2$O | 0.000 |
| KH$_2$PO$_4$ | 0.026 |
| NaCl | 0.000 |
| CaCl$_2$—2H$_2$O | 0.001 |
| Yeast Extract | 0.049 |
| NaOH, 50% | 0.000 |
| Total: | 10.296 |
| TS, %: | 17.03 |
| Brix, %: | 17.77 |
| S/M: | 1.990 |

The medium was adjusted to pH 6.50 with 50% NaOH and inoculated with 100 g of late-log *L. citreum* NRRL B-742 grown in medium of the same composition. The fermentation was allowed to proceed for 55 hours with pH control to maintain the pH at 5.5 once that pH was achieved via bacterial acidogenesis. The fermenter was sampled at regular intervals for analysis via HPAEC-PAD and HPLC-RID.

Results:

The sucrose:maltose (S/M) ratio of the pre-inoculation medium was confirmed by HPLC-RID (BioRad Aminex, HPX-87P, 80° C., water at 0.6 mL/min) (Table 13).

TABLE 13

Pre-Inoculation Medium Sugar Content and Sucrose:Maltose Ratio

| Compound: | %/brix Pre-inoculum: |
|---|---|
| Sucrose | 61.88 |
| Maltose | 32.00 |
| Glucose | 0.25 |
| fructose | 0.00 |
| Total: | 94.14 |
| S/M: | 1.93 |

Figure 11:
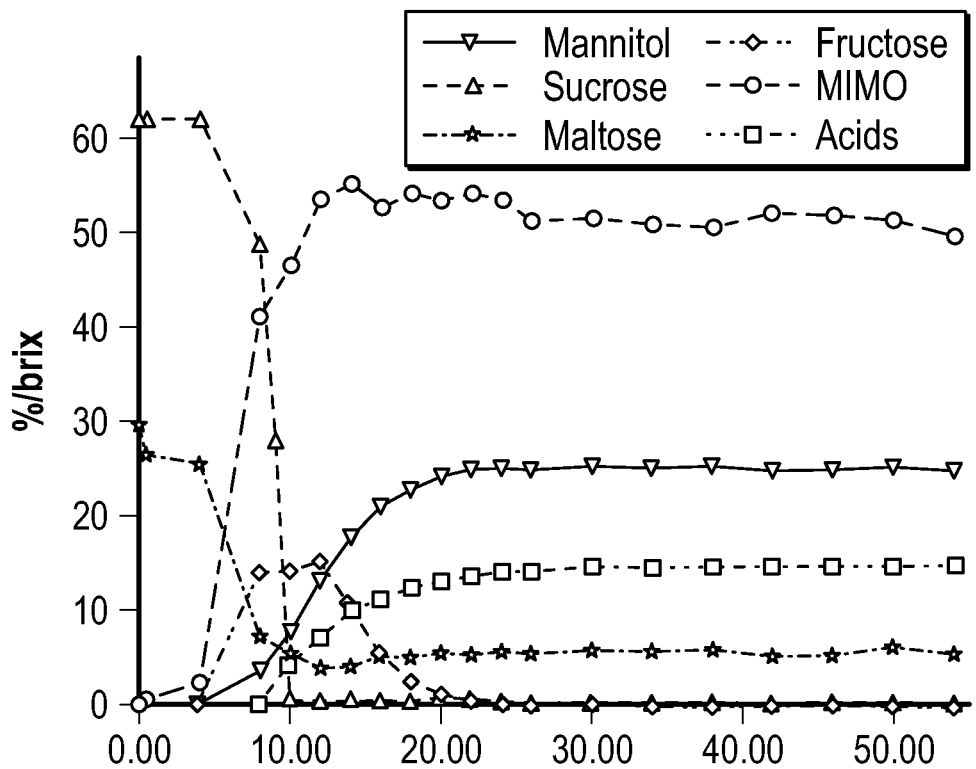
FIG. 11 graphically illustrates the generation of chemical species (as detected by HPAEC-PAD and HPLC-RID) throughout the course of a 10 L fermentation (sucrose: maltose (S/M, w/w) ratio=2.00) with *L. citreum* NRRL B-742.
Figure 12:
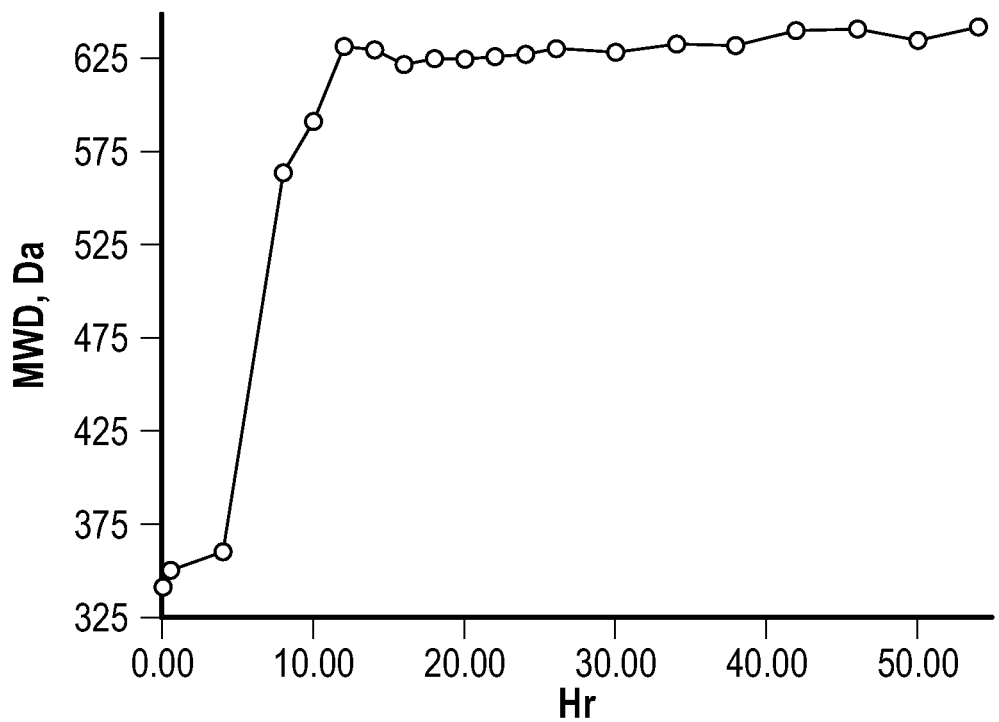
FIG. 12 graphically illustrates evolution of the mass average molecular weight distribution (MWD) of MIMOs throughout the course of a 10 L fermentation (sucrose: maltose (S/M, w/w) ratio=2.00) with *L. citreum* NRRL B-742. Note that the MWD continues to increase (until about 15 hours) after the sucrose is exhausted (at about 10 hours). The rate of chain growth then takes place at a lower, but constant rate until the end of fermentation (55 hours) when a MWD of 642.5 Da was achieved.

The amount of feedstock (sucrose and maltose), product (MIMO), intermediate (fructose), and byproducts (total organic acids and mannitol) over time as detected via HPLC-RID and HPAEC-PAD, are given in FIG. 11. The evolution of the mass-average molecular weight of the MIMO is shown in FIG. 12.

Ultimately, the starting sucrose:maltose ratio of about 2.00 (1.93 at the time of inoculation) yielded 51.17%/brix MIMO (60.11%/total sugars) that had a mass-average MWD of 642.46. See chart Table 14 below.

TABLE 14

Product Composition after Fermentation using a 2.00 Ratio of Sucrose:Maltose

| Component | %/brix: | | %/brix |
|---|---|---|---|
| Glucose | 0.35 | | |
| Fructose | 0.01 | MIMO-DP3 | 14.69 |
| Sucrose | 0.34 | MIMO-DP4 | 20.17 |
| Maltose | 6.56 | MIMO-DP5 | 11.92 |
| MIMO | 50.29 | MIMO-DP6 | 2.88 |
| Mannitol | 25.02 | MIMO-DP7 | 0.62 |
| Lactate | 10.210 | MIMO-DP8 | 0.00 |
| Glycerol | 0.828 | MIMO-DP9 | 0.00 |
| Formate | 0.120 | | |
| Acetate | 4.547 | | |
| TOTAL: | 98.28 | | |
| MIMO: | 50.29 | | |
| Purity, %: | 51.17 | | |
| Mw, Da: | 642.46 | | |

As illustrated the product of such fermentation methods have significant amounts of small molecules such as mannitol, lactate, and organic acids (e.g., acetate, formate).

Example 4

Figure 8:
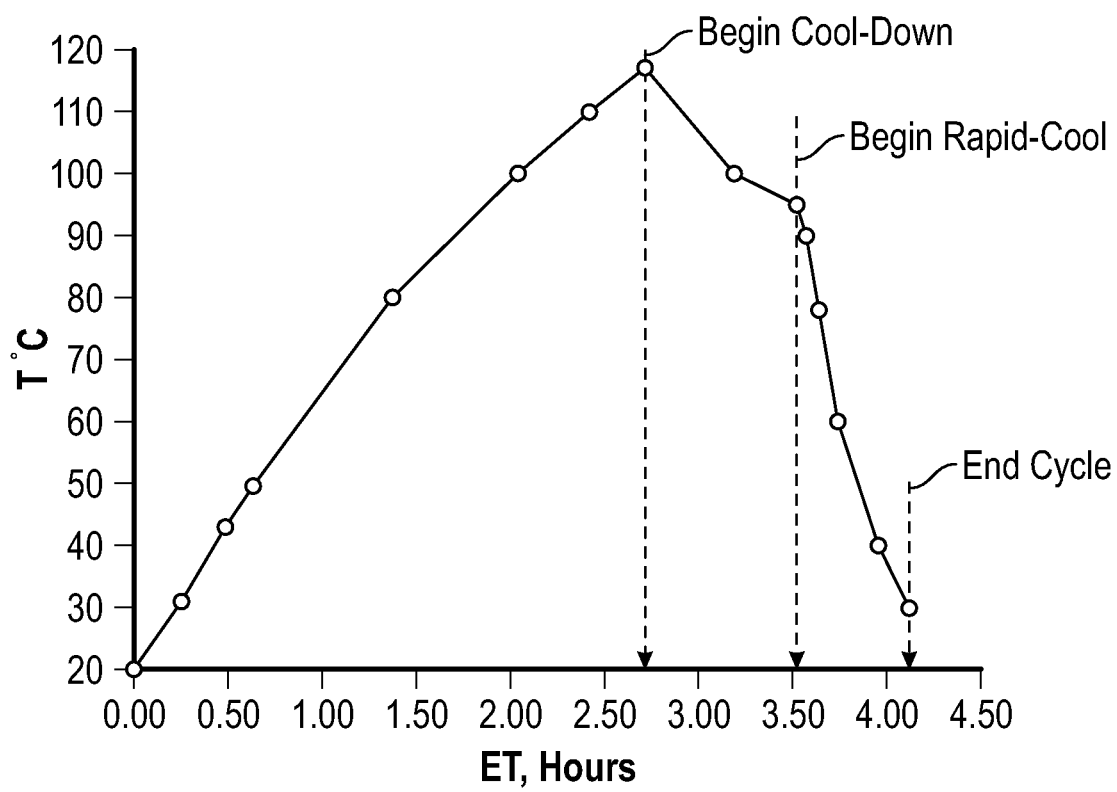
FIG. 8 shows the heating/cooling curve employed during a typical sterilization in place (SIP) cycle run on a New Brunswick BioFlo 410 fermenter.

This Example illustrates that fermentation at the 10 L scale, using a sucrose:maltose ratio of 2.75 at time of inoculation, with introduction of sugars via filtration through a 0.2 μm filter (sterilized by filtration, SBF), will give a MWD similar to that which arises from a fermentation batch with a starting sucrose:maltose ratio of 2.00 prior to SIP (i.e. approx. 2.73 at time of inoculation, see FIG. 8).

10 L Trial Fermentation at S/M=2.75 at the Time of Inoculation with SBF of Sugars Experimentally, this fermentation is identical to that demonstrated in Example #3 with the exception that the amount of both sucrose and maltose have been altered in order to achieve an S/M of 2.75 at the time of inoculation whilst maintaining a total sugar of approximately 17-18% w/w.

The final sterile medium contained the components listed in Table 15.

TABLE 15

Medium with 2.75 Sucrose:Maltose Ratio

| 10 L #2 | Total kg: |
|---|---|
| Water | 8.740 |
| Sucrose | 1.333 |
| Maltose-$H_2O$ | 0.536 |
| $MnSO_4$—$H_2O$ | 0.000 |
| $MgSO_4$ | 0.001 |
| $FeSO_4$—$7H_2O$ | 0.000 |
| $KH_2PO_4$ | 0.026 |
| NaCl | 0.000 |
| $CaCl_2$—$2H_2O$ | 0.001 |
| Yeast Extract | 0.049 |
| NaOH, 50% | 0.000 |
| Total: | 10.685 |
| TS, %: | 16.99 |
| Brix, %: | 17.70 |
| S/M: | 2.751 |

Figure 13:
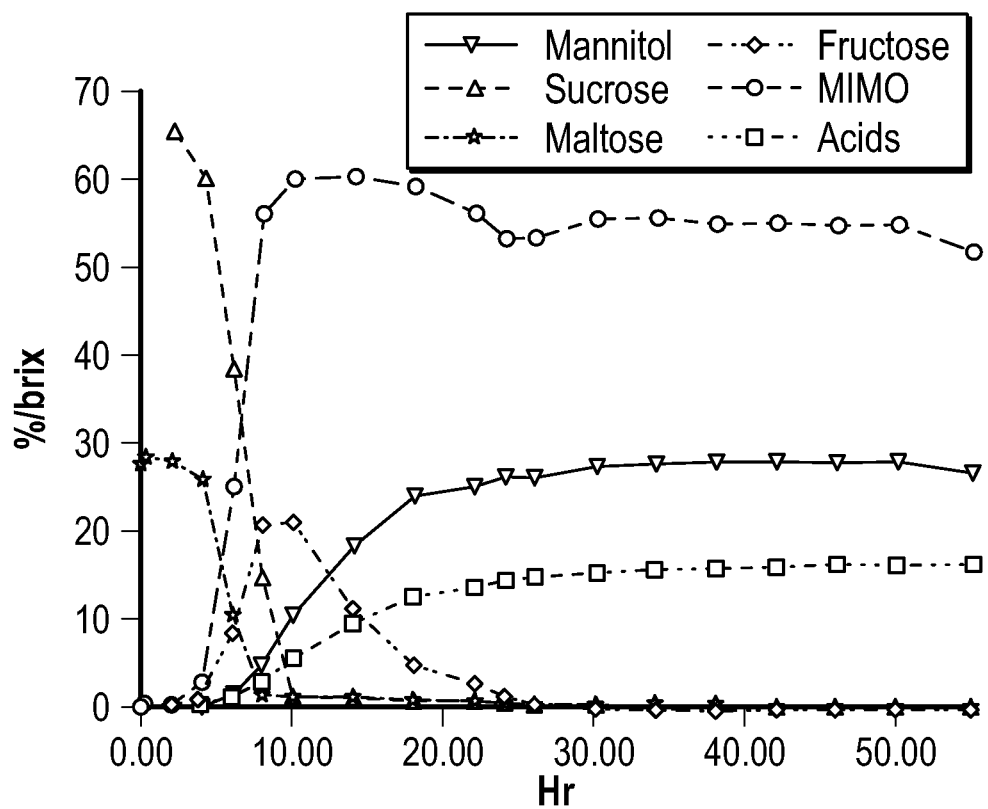
FIG. 13 graphically illustrates the generation of chemical species (as detected by HPAEC-PAD and HPLC-RID) throughout the course of a 10 L fermentation (sucrose/maltose=2.75) with *L. citreum* NRRL B-742.
Figure 14:
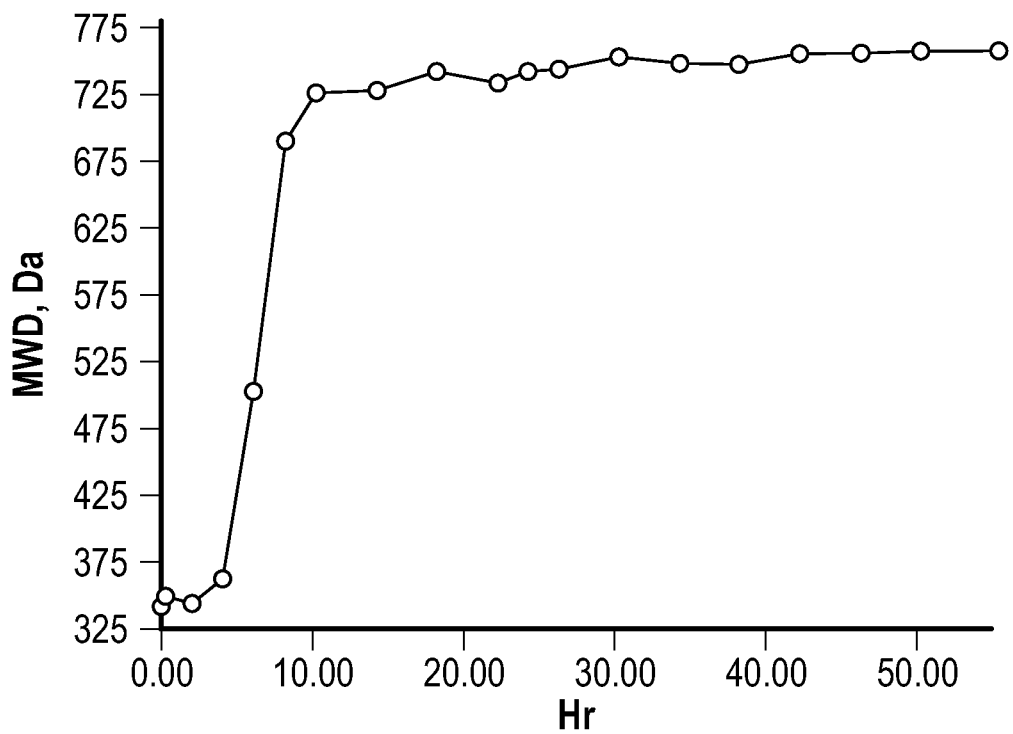
FIG. 14 graphically illustrates the evolution of the mass average molecular weight distribution (MWD) of MIMOs throughout the course of a 10 L fermentation (S/M=2.75) with *L. citreum* NRRL B-742. Note that the MWD continues to increase (until ~15 hours) after the sucrose is exhausted (~10 hours). The rate of chain growth then takes place at a lower, but constant rate until the end (55 hours) where a MWD of 760.7 Da was achieved.

The fermentation behaved normally for *L. citreum* NRRL B-742 grown on this medium and with pH controlled at 5.5 using 50% NaOH. The amounts of feedstock (sucrose and maltose), product (MIMO), intermediate (fructose), and byproducts (total organic acids and mannitol) over time as detected by HPLC-RID and HPAEC-PAD, are given in FIG. 13. Note that the metabolic activities and MIMO yield are essentially the same as those shown in Example #3 (compare FIG. 13 to FIG. 12), but the evolution of the mass-average molecular weight of the MIMO, shown in FIG. 14, is quite different and reflects the increased sucrose:maltose ratio.

Ultimately, fermentation at a sucrose:maltose ratio of about 2.75 (2.72-2.75) at the time of inoculation yielded 53.32%/brix MIMO (57.44%/total sugars) with a mass-average MWD of 760.73 Da. This is consistent with results shown in Example #2 where the pre-inoculated sucrose/maltose ratio had increased from 2.00 to 2.73 during sterilization in place (SIP).

The following chart shows the composition of the fermentation broth so obtained at the left, with the distribution of MIMO at the right.

TABLE 16

Fermentation Broth using Medium with 2.75 Sucrose:Maltose Ratio

| Component | %/brix: | | %/brix |
|---|---|---|---|
| Glucose | 0.11 | | |
| Fructose | 0.08 | MIMO-DP3 | 7.66 |
| Sucrose | 0.73 | MIMO-DP4 | 17.24 |
| Maltose | 0.67 | MIMO-DP5 | 17.17 |
| MIMO | 52.19 | MIMO-DP6 | 7.20 |
| Mannitol | 27.11 | MIMO-DP7 | 2.02 |
| Lactate | 11.66 | MIMO-DP8 | 0.89 |
| Glycerol | 0.20 | MIMO-DP9 | 0.00 |
| Formate | 0.03 | | |
| Acetate | 5.10 | | |
| TOTAL: | 97.89 | | |
| Purity, %: | 53.32 | | |
| Mw, Da: | 760.73 | | |

As illustrated the product of such fermentation methods have significant amounts of small molecules such as mannitol, lactate, and organic acids (e.g., acetate, formate).

Example 5

Colored by-products remained in the final product (imparting a brown color and caramel-like flavor) when using the processes described above in Examples 1, 2, and 3. While not undesirable (organoleptically), it is a difficult parameter to control, and it was preferable to avoid destroying maltose from a cost perspective (it is expensive). With these considerations in mind scale-up experiments were designed to test SIP of bulk water and minerals, and filter sterilization of the carbohydrate components. As illustrated in this Example, such a process avoided color formation and facilitated more precise control over the S/M (fixed at 2.75).

Improved Composition for Scale-Up

To a 2 L fermenter (New Brunswick Celligen 512) was added the components listed in Table 17.

TABLE 17

Medium for Batch 51815

| Batch: 51815 | kg: | g: |
|---|---|---|
| Water | 1.752 | |
| $MnSO_4$—$H_2O$ | 0.00002 | 0.02093 |
| $MgSO_4$ | 0.00020 | 0.20312 |
| $FeSO_4$—$7H_2O$ | 0.00002 | 0.02160 |
| $KH_2PO_4$ | 0.00557 | 5.56501 |
| NaCl | 0.00002 | 0.02068 |
| $CaCl_2$—$2H_2O$ | 0.00011 | 0.11113 |
| Yeast Extract | 0.01043 | 10.42705 |
| NaOH, 50% | 0.00096 | 0.95946 |
| Total: | 1.769 | |

This mixture was sealed in the fermenter and autoclaved at 121° C. for 15 minutes. While the contents of the fermenter were still hot (80-90° C.), 0.270 kg of sucrose and 0.108 kg of maltose monohydrate were transferred into the fermenter and dissolved via strong agitation at 400 RPM. Once cooled to 27° C., the whole mixture was sampled for analysis via HPLC-RID, confirming that the sucrose:maltose ratio was 2.72.

The fermenter was inoculated with 20 mL late-log *L. citreum* NRRL B-742, made as previously described, and the pH was controlled as previously mentioned. Fermentation was allowed to proceed for 62 Hr with daily sampling. During this time, the fermentation consumed approximately 43 g of 40% NaOH.

At 62 Hr, the whole batch was harvested, and the cells removed as previously described, to give 17.8 brix broth with a conductivity of 19.1 mS/cm. The broth was of much lower color, e.g. 1039.5 IU relative to 11,799 IU for the same (complete) media run through and SIP cycle. Due to the reduced color, the requirement for powdered activated carbon was reduced by a factor of four, and still have headroom within a factor of two.

The broth was concentrated to 45.0 brix by evaporation and decolorized with 0.1333% (over starting mass of medium) CA-50S PAC (29.2 g), as previously described.

The minerals/salts and organic acids were removed from 1.075 kg of decolorized liquor at 39 brix as previously described. The combined de-ashed liquor was adjusted to pH 6.16 (from pH 10.80) with 37% HCl (8.73809 g) and the whole de-ashed liquor concentrated by evaporation to 57.04 brix.

The de-ashed concentrate was transferred hot into a one liter crystallization vessel and allowed to slowly cool to room temperature (19-22° C.) and crystallize overnight.

The resulting mixture was homogenized to yield a pourable crystal slurry. The mannitol crystals were separated via basket centrifuge (Robitel RA 20 VX with a 10 µm polypropylene filter bag). The crystal cake (0.320 kg at 95% solids, cake #1) was washed, in small portions, with 500 mL ice-cold deionized water. 0.697 kg cake washings (wash #1) at 20.5 brix were retained for recycle. 2.626 kg liquor (liquor #1) at 51.70 brix was refrigerated to 3° C. and allowed to crystallize overnight.

The crystals (cake #2, 0.109 kg at 95% solids) were removed, as before. The cake wash #2 was combined with wash #1 for recycle. The product liquor #2 at 49.0 brix was analyzed (HPAEC-PAD, HPLC-RID, brix, pH and conductivity).

Results

The composite results of the product composition as detected via HPAEC-PAD and HPLC-RID are given below.

TABLE 18

Batch 51815 Product Composition

| Hr: | 15 | 39 | 63 |
|---|---|---|---|
| brix: | 18.2 | 17.8 | 17.8 |
| mannitol | 25.88 | 26.50 | 26.49 |
| glucose | 0.02 | 0.13 | 0.67 |
| fructose | 1.73 | 0.06 | 0.01 |
| sucrose | 0.22 | 0.13 | 0.23 |
| maltose | 2.35 | 2.49 | 3.01 |
| DP 3 | 10.71 | 7.41 | 7.39 |
| DP 4 | 20.26 | 16.83 | 13.98 |
| DP 5 | 17.49 | 16.90 | 15.68 |
| DP 6 | 6.29 | 7.56 | 7.87 |
| DP 7 | 1.58 | 2.16 | 2.49 |
| DP 8 | 0.79 | 0.91 | 1.21 |
| DP 9 | 0.00 | 0.00 | 0.00 |
| lactate | 9.55 | 13.01 | 13.17 |
| glycerol | 0.00 | 0.00 | 0.00 |
| formate | 0.00 | 0.00 | 0.00 |
| acetate | 4.52 | 4.77 | 4.85 |
| TOTAL: | 102.02 | 100.51 | 98.77 |
| MIMO, %: | 57.13 | 51.76 | 48.62 |
| Purity, %: | 56.00 | 51.50 | 49.22 |
| MWD: | 727.43 | 754.80 | 761.03 |
| Yield %: | 57.78 | 51.97 | 49.68 |

As illustrated the product of such methods may remove some contaminants, but the product still has significant amounts of small molecules such as mannitol, lactate, and organic acids (e.g., acetate).

Example 6

The process incarnations described in the previous examples (1-5) were integrated and scaled up to 3000 L with a theoretical overall process yield of 240 kg MIMO (DS)/total sugars fed. These examples detail the scaled process, and the composition obtained thereby.

Commercial-Scale Production of MIMO

Fermentation/MIMO Biosynthesis

To 3.7 kg RO (reverse osmosis) water was added sucrose (refined white, from cane), 0.5302 kg; maltose monohydrate (Sunmalt-S[N]), 0.2935 kg; yeast extract (Marcor bacteriological grade), 0.0221 kg; potassium phosphate monobasic, 0.0118 kg; magnesium sulfate (anhydrous), 0.00043 kg; ferrous sulfate heptahydrate, 0.000045 kg; manganese sulfate monohydrate, 0.000045 kg, sodium chloride, 0.000045 kg, and calcium chloride dihydrate (USP), 0.00024 kg.

The pH of the medium was adjusted to 7.0 with 50% NaOH (FCC), 0.0057 kg.

700 mL of medium was dispensed into each of six unbaffled Fernbach flasks. The flasks were sealed using foam plugs and autoclaved at 121° C. for 15 minutes.

Five of the six flasks were inoculated with 1 mL each of vial stock (*Leuconostoc citreum* NRRL B-742; 0.5 mL late-log culture+0.5 mL glycerol, 40%, certified Kosher-Pareve). The sixth flask was an uninoculated control.

The flasks were incubated at 27° C. for 16 Hr ($OD_{600}$=1.476±0.03) with agitation at 150 RPM. The inoculum was inspected via microscopy to determine the culture was clean prior to use.

The following was added to a batch tank: water purified by reverse osmosis (RO water) 1440 kg; sucrose, 498.96 kg; maltose monohydrate, 200 kg; sodium chloride, 0.037 kg; and calcium chloride dihydrate, 0.204 kg.

In the meantime, a 1200-gallon seed fermenter was cleaned in place. To the seed fermenter was added RO water, 238 kg; yeast extract, 2.76 kg; potassium phosphate monobasic, 1.48 kg; magnesium sulfate (anhydrous); 0.054 kg, ferrous sulfate heptahydrate, 0.0057 kg; and manganese sulfate monohydrate, 0.0057 kg.

The contents of the fermenter were thoroughly mixed, allowed to rest at 37° C. for two hours, and then sterilized in place at 121° C. for 60 minutes.

Once cooled, 309.2 kg of the sugar and salt solution was transferred from the charge tank to the seed fermenter through a sterilizing 0.2 μm filter capsule with a 1.0 μm pre-filter (20' Cuno cartridge filter). The filter and lines were washed through with 10 kg of RO water. The mixed medium had a pH of 5.47.

The seed fermenter was inoculated with 3.8 kg late-log flask culture. The fermentation was allowed to proceed under 1-3 psig air (in headspace to maintain positive pressure), at 27° C., with agitation at 42 RPM for 16 hours ($OD_{600}$=2.74).

In the meantime, into a cleaned in place production fermenter was added RO water, 1332 kg, yeast extract, 15.01 kg; potassium phosphate monobasic, 8.01 kg; magnesium sulfate (anhydrous), 0.2922 kg; ferrous sulfate heptahydrate, 0.030 kg, and manganese sulfate monohydrate, 0.030 kg. This mixture was sterilized in place at 121° C. for 60 mins. Into this mixture was pumped 1141 kg of the sugar and salt solution (from the charge tank) through a sterilizing 0.2 μm filter capsule with a 1.0 μm pre-filter (20' Cuno cartridge filter).

Thirty-one kg of late-log seed culture (*L. citreum* NRRL B-742.) was used to inoculate the production fermenter. The pH was adjusted to 6.52 with 50% NaOH, and the fermentation was allowed to proceed for 55 hours at 27° C., 1-3 psig air, and with agitation at 31 RPM. The pH was maintained at 5.5 with 50% NaOH (appx 120 kg).

Figure 15:
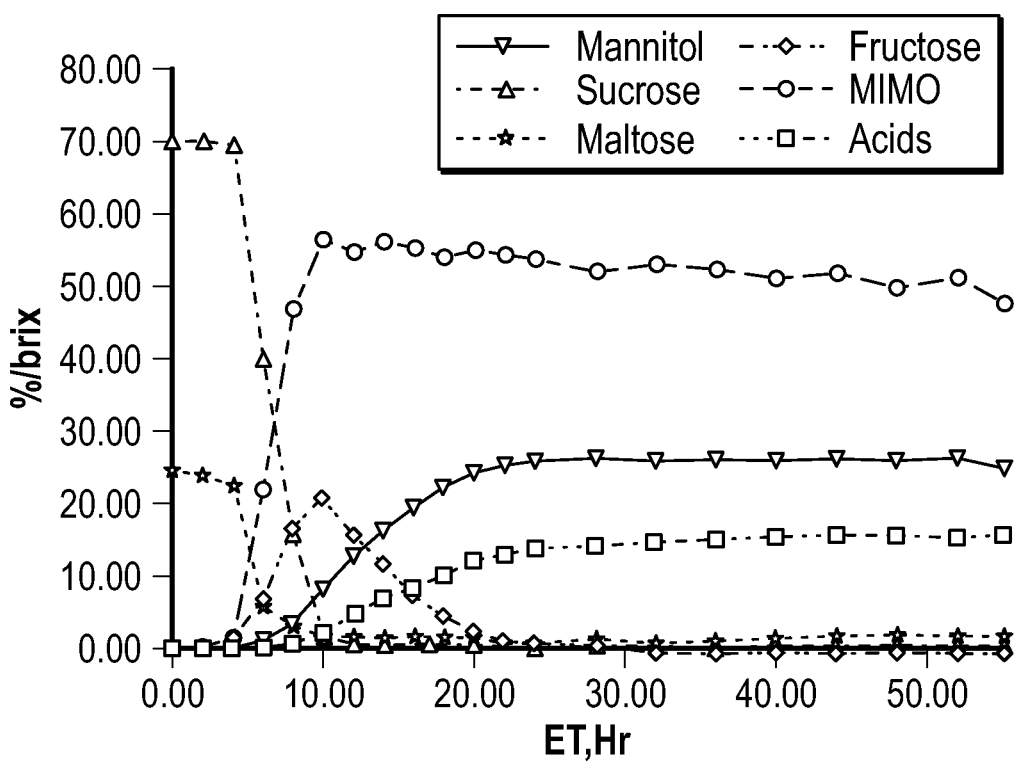
FIG. 15 graphically illustrates the generation of chemical species (as detected by HPAEC-PAD and HPLC-RID) throughout the course of a 3000 L fermentation (sucrose/maltose=2.75, lot #150622) with *L. citreum* NRRL B-742.
Figure 16:
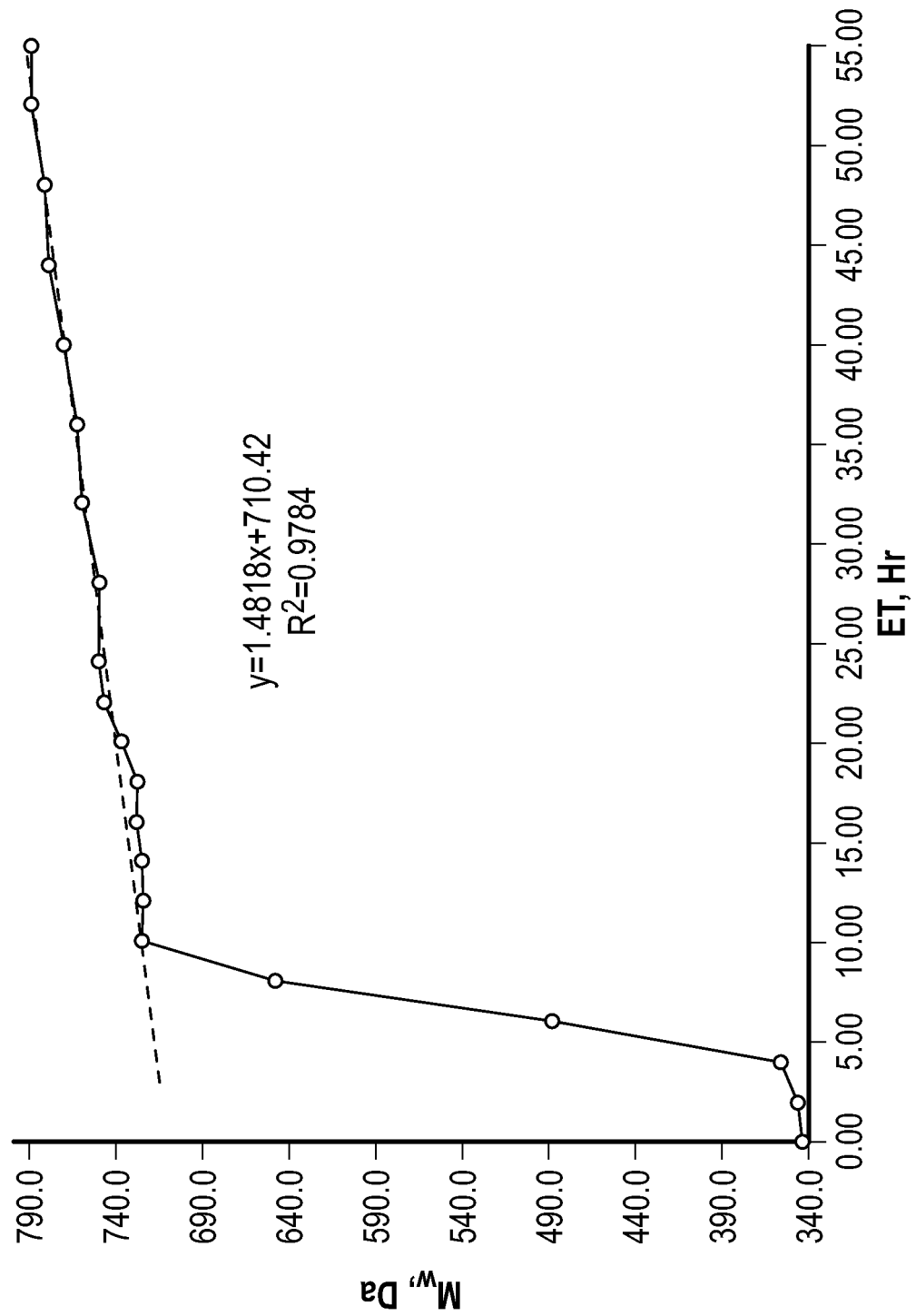
FIG. 16 graphically illustrates the evolution of the mass average molecular weight distribution (MWD) of MIMOs throughout the course of a 3000 L fermentation (sucrose/maltose=2.75, lot #150622) with *L. citreum* NRRL B-742. Note that the mass average molecular weight distribution continues to increase (until about 15 hours) after the sucrose is exhausted (at about 10 hours). The rate of chain growth then takes place at a lower, but constant rate until the end (55 hours) where a mass average molecular weight distribution of 789.5 Da was achieved.

FIG. 15 graphically illustrates composition of the broth therein made, and FIG. 16 illustrates the MIMO molecular weight over time during the fermentation.

Downstream Processing/Work Up

The biomass (cells, etc.) was removed from the fermentation broth via passage through a 0.2 μm microfilter (skid). Any remaining MIMO held up in the retentate was recovered via six stages of diafiltration. The permeate and diafiltrate were combined and evaporated to approximately 40 brix via wiped film evaporator (WFE). The resulting concentrate was discharged hot and treated with 12.5 kg of powdered activated carbon (PAC, Carbochem CA-50S) and 21 kg Celite 545 diatomite filter aid. The whole mixture was stirred for 20 minutes before filtration through a filter press with a 20 kg Celite 545 pre-coat. A 1 μm cartridge filter was used to polish fines from the filtrate. RO water, 700 kg was used to wash the PAC cake.

The filtrate and PAC wash were combined to give 1277 kg of decolorized concentrate at 29.3 brix.

The decolorized concentrate was de-ashed via passage (5×300 kg slugs) through strong acid cation (SAC, Purolite C-150S, $H^+$ form, 14.0 cubic feet) and a weak base anion (WBA, Purolite A-133, free-base form, 13.5 cubic feet) ion exchange resins.

The combined ion exchange (IEX) product (5.6 brix) was filtered through a 0.2 mm capsule filter into a cleaned in place holding tank where it was adjusted to pH <4.2 (2.8, actual) with 31% hydrochloric acid.

The acidified IEX product was concentrated to 54.21 brix via evaporation (WFE), discharged hot into 2×1 $m^3$ stainless steel totes. These were allowed to slowly cool, with slow agitation (pneumatic mixer) to room temperature (25° C.).

The crystals were removed from the mother liquor via passage through a Hastalloy nutsch filter (10 mm filter disk and Celite 545 pre-coat) to yield 273 kg of liquor #1.

The crystal cake (153 kg) was washed with cold RO water, 285 kg to yield 342 kg cake wash #1 and 60 kg cake #1.

Cake wash #1 was frozen for recycle into a future batch and Liquor #1 was evaporated to 65.60 brix by evaporation (pot still). The resulting liquor was discharged hot into a 1 $m^3$ stainless steel tote and allowed to slowly cool, with slow agitation (pneumatic mixer) to room temperature (25-30° C.). Then, the tote was moved into a freezer where the crystallization was continued with slow cooling to 5° C.

The crystals were removed from the mother liquor via passage through a Hastalloy nutsch filter (10 mm filter disk and Celite 545 pre-coat) to yield 127.1 kg of liquor #2 at 64.04° brix. The crystal cake was washed with cold RO water to yield 184 kg cake wash #2 and 39.4 kg cake #2.

Cake wash #2 was frozen for storage and recycle into the next batch.

Liquor #2 was pasteurized at 70° C. for 30 minutes in the pot still, cooled and packaged into 55-gallon sanitized poly drums.

Samples were submitted for microbiological testing and to analytics for issuance of batch COA.

The composition thereby made was as shown in Table 19 (as detected by HPAEC-PAD).

TABLE 19

| Product Lot 150622 Composition | | | |
|---|---|---|---|
| Component | %/brix: | | %/brix |
| Glucose | 0.46 | | |
| Fructose | 0.05 | MIMO-DP3 | 11.89 |
| Sucrose | 1.75 | MIMO-DP4 | 28.06 |
| Maltose | 4.39 | MIMO-DP5 | 28.67 |
| MIMO | 95.51 | MIMO-DP6 | 16.77 |
| Mannitol | 8.35 | MIMO-DP7 | 6.58 |
| Lactate | 0.00 | MIMO-DP8 | 2.80 |
| Glycerol | 0.51 | MIMO-DP9 | 0.73 |
| Formate | 0.00 | | |
| Acetate | 0.00 | | |
| TOTAL: | 111.03 | | |
| Purity, %: | 86.02 | | |
| Mw, Da: | 789.46 | | |

Figure 17:
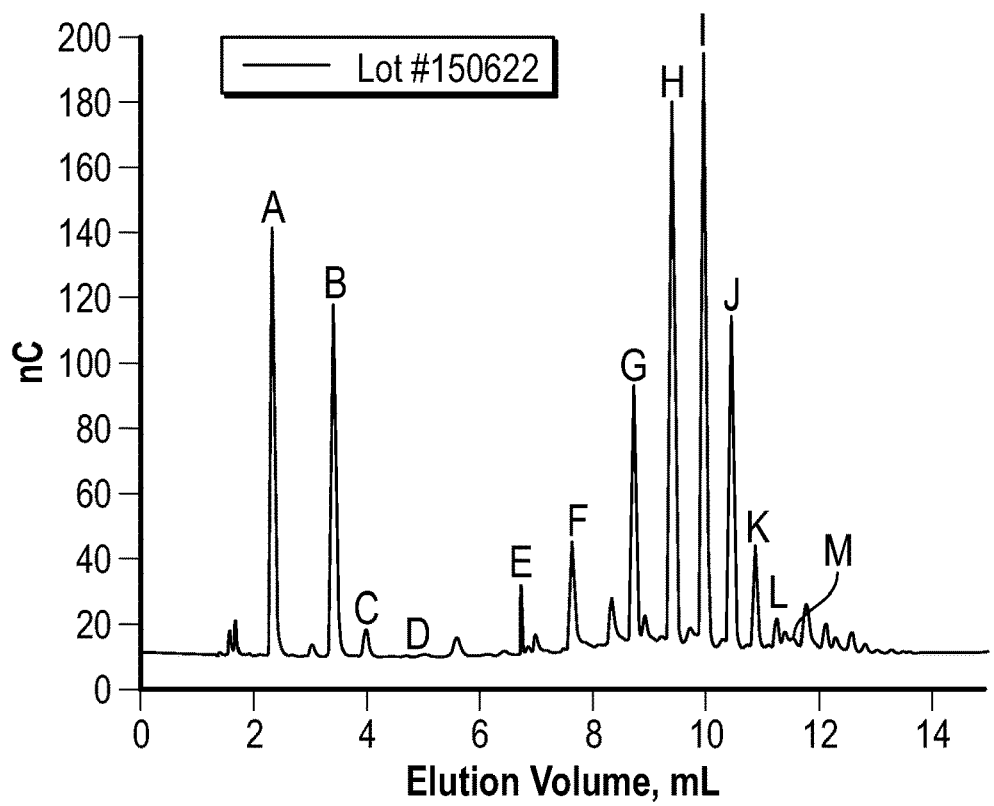
FIG. 17 shows a HPAEC-PAD chromatogram of product lot #150622 wherein the components are identified as A: D-mannitol; B: L-arabinose (internal standard); C: D-glucose; D: D-fructose; E: sucrose; F: maltose; and where G-M correspond to MIMO DP 3-9.

FIG. 17 shows a HPAEC-PAD chromatogram of product lot #150622 wherein the components are identified as A: D-mannitol; B: L-arabinose (internal standard); C: D-glucose; D: D-fructose; E: sucrose; F: maltose; and where G-M correspond to MIMO DP 3-9. As illustrated, the fermentation process generates a MIMO product without significant organic acids, but the crystallization and freezing steps were not easily automated.

Example 7: Nanofiltration Cleanup of Cell-Free Fermentation Broth

This Example describes partial cleanup of fermentation broth after cell removal.

Methods

Fermentation was performed as described in the foregoing examples. The biomass (cells, etc.) was removed from the fermentation broth via passage through a 0.2 μm microfilter (skid) where the MIMOs were collected in the permeate. The MIMO held up in the retentate was recovered via six stages of diafiltration. The permeate and diafiltrate were combined to provide a cell-free fermentation broth.

Different nanofiltration processes were tested to determine which process was better. Two nanofiltration pore sizes were evaluated. Two nanofiltration units were prepared that included tubular crossflow membrane skid with eight elements, one with a 500 Da (actually about 450 Da) molecular weight cut-off, and a second with a 200 Da molecular weight cut-off. The pore size determines what component of the liquid will pass through as the permeate. The goal was to remove salts, organic acids and sugars such as mannitol, fructose, glucose, and sucrose, which flow through while MIMOs with DP3 (504 daltons) and larger are retained.

A temperature-controlled vessel was used to hold the cell-free fermentation broth as it was pumped under high pressure through the 500 Da or 200 Da nanofiltration units. In this case, we tested two membrane pore sizes and determined one to be superior and extremely effective. The tested pore sizes were reported to have molecular weight cut-offs of less than or equal to 200 Da and less than or equal to 500 Da. In practice these seem to be actually smaller than the reported sizes and the less than or equal to 500 appeared to behave as though it had a 450 Da cutoff.

Figure 1C:
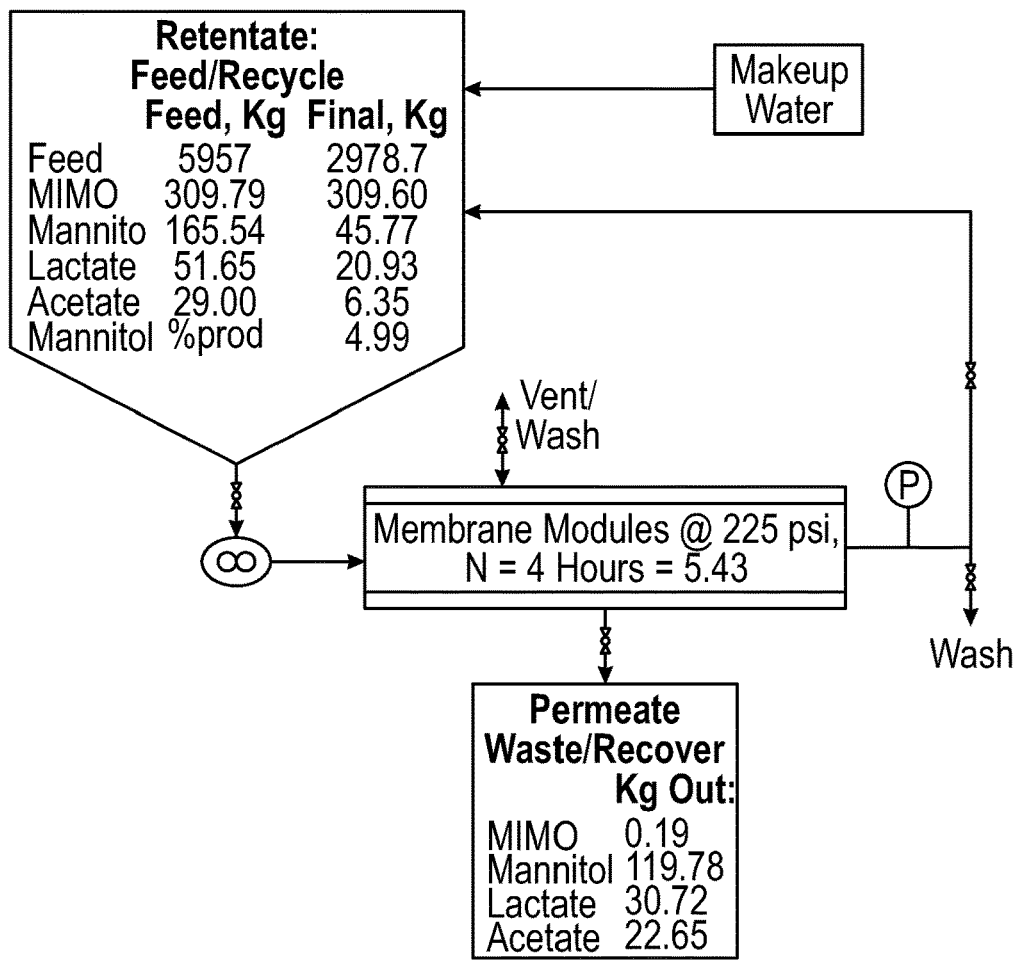
Figure 2:
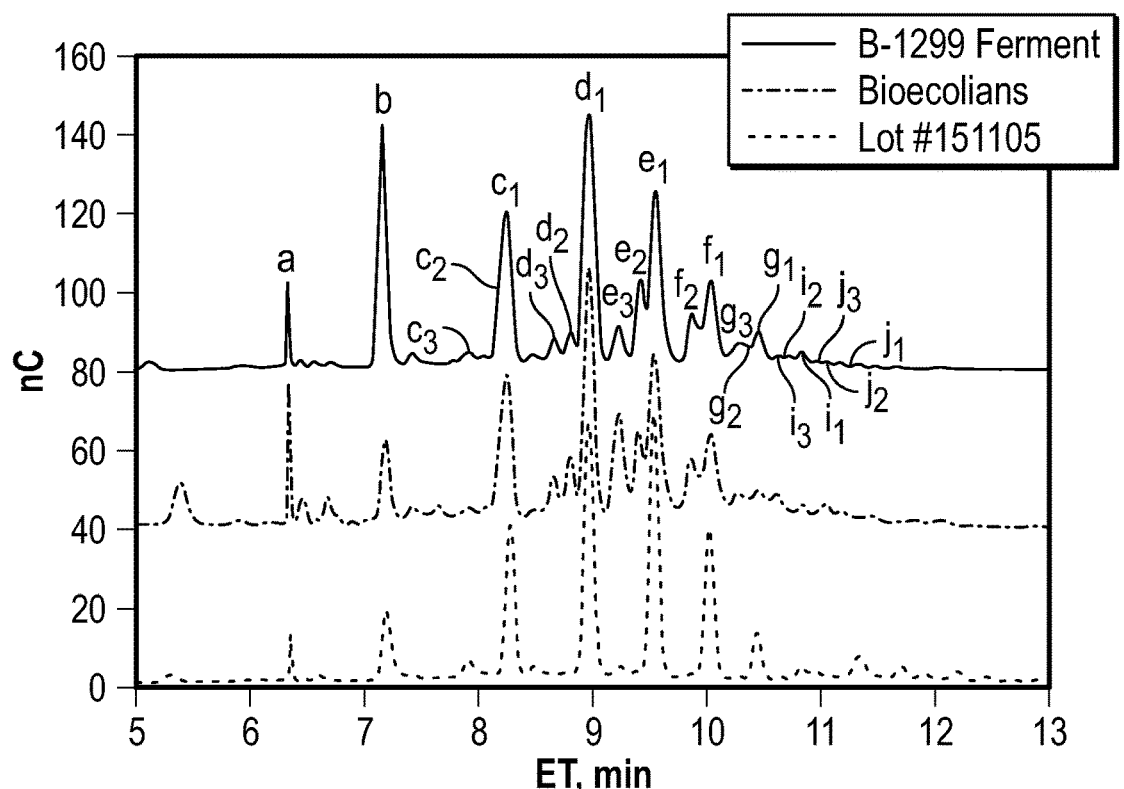
FIG. 2 illustrates various MIMO products where the components were separated by High-Performance Anion-Exchange Chromatography with Pulsed Amperometric Detection (HPAEC-PAD): (1) a final fermentation broth generated using an ISOThrive fermentation process with NRRL B-1299; (2) a commercial MIMO formulation made using an immobilized dextransucrase enzyme from NRRL B-1299; and (3) a typical product made using a process described in U.S. patent application Ser. No. 14/833,094, filed Aug. 22, 2015 (incorporated herein by reference in its entirety) using NRRL B-742. Note that equivalent components a-j are observed, which correspond to a. sucrose, b. maltose, and c-j corresponding to MIMO with (degree of polymerization (DP) 3-9, respectively. Subscript C1 denotes MIMO with (1) α-(1,6) linear chains; (2) α-(1,2) branched chains; and, (3) α-(1,3) branched chains. The left-most peak is mannitol.

The fermentation broth was applied to the nanofiltration units at various Brix levels and measurements of the overall flux rate and the dry solids flux rate were obtained. FIG. 1C illustrates one example of a nanofiltration unit.

The purity of MIMOs of the feed recycled through the nanofiltration units was analyzed via an Agilent 1100 HPLC-RID BioRad HPX-87H (300 mm) column at 65° C., with elution via 0.008N sulfuric acid isocratic at 0.6 mL/min using a differential refractive index detector at 45° C.

Results

No DP3 was detected in the permeate of the 500 Da nanofiltration unit. Hence, the 450-500 Da molecular weight cut-off was selected for use in the cleanup of the MMOs in the fermentation broth. These results also indicate that the 500 Da membrane pore size behaves as if it had a cutoff that was smaller than 500 Da (e.g., 450 Da cutoff).

Various Brix levels were evaluated to determine optimal flux rate and the dry solids flux rate. A highly dilute liquid, running the system initially to simultaneously remove the dry solids and water and to concentrate the MIMOs was better. FIG. 1C provides an example of a nanofiltration unit and an example of one cleanup process.

In one experiment, the flux of the fermentation broth through a nanofiltration pilot unit was as shown in the following Table 20.

TABLE 20

Nanofiltration Fluid Analysis

| Retentate Brix | permeate kg/hr | flux kg/m2/hr | Permeate Brix | Permeate DS, kg/hr: |
|---|---|---|---|---|
| 10.0 | 4.438 | 92.1 | 2.5 | 0.111 |
| 16.1 | 2.404 | 49.9 | 5.1 | 0.123 |
| 19.6 | 1.506 | 31.2 | 7.8 | 0.117 |
| 24.2 | 1.102 | 22.8 | 11.6 | 0.128 |

In a further experiment, the 500 Da molecular weight cut-off unit [AFC3, "500 Da" MWCO tubular membrane, 122 cm (L)×1.3 cm (ID)] was operated efficiently at pressure 25 psi retentate-side (65° C.) with 12.271 kg feed at 8.7 brix or when operating at 10.4 brix (retentate maintained with water) with 2.44 kg/hr permeate (waste) feed at 2.63 brix. The result was 642 g DS/hr/membrane.

Table 21 illustrates parameters relating to flux through the nanofiltration unit.

TABLE 21

Flux Parameters of Nanofiltration Unit

| | | | | | |
|---|---|---|---|---|---|
| Pilot tube (L), cm: | 121.91 | Perm brix: | 4.7 | Fermentation, L: | 3000 |
| Pilot tube (D), cm: | 1.257 | DS/hr: | 0.1684 | Fermentation brix: | 18.5 |
| Pilot tube (SA), m² : | 0.0481 | Mod. kg/hr: | 193.55 | Fermentation, kg: | 3220 |
| Pilot kg/hr: | 3.584 | Mod. DS/hr: | 9.097 | Feed brix: | 10 |
| Flux, kg/m2h-1: | 74.446 | Modules: | 4 | Feed, kg: | 5957.5 |
| Scale tube, (L), cm: | 365.76 | SA, m2: | 10.40 | DS, kg; | 595.75 |
| Scale tube (SA), m²: | 0.144 | Hours: | 5.43 | Mannitol, % Bx: | 27.79 |
| Module (SA), m²: | 2.600 | Kg flow, tot: | 4203.9 | Lactate, %/bx: | 8.67 |
| Scale factor: | 54.064 | DS, kg tot: | 197.6 | Acetate, %/bx: | 4.87 |
| | | | | Mannitol, kg: | 165.543 |
| | | | | Lactate, kg: | 51.645 |
| | | | | Acetate, kg: | 28.996 |
| | | | | Mann -kg/hr: | −22.06 |
| | | | | Lactate -kg/hr: | −5.66 |
| | | | | Acetate -kg/hr: | −4.17 |
| | | | | Mann. Final, % bx: | 7.68 |
| | | | | Mann % prod. w/w: | 4.99 |
| | | | | MIMO -kg/hr: | −0.04 |
| | | | | Mannitol, kg: | 165.543 |
| | | | | Lactate, kg: | 51.645 |

Figure 18:
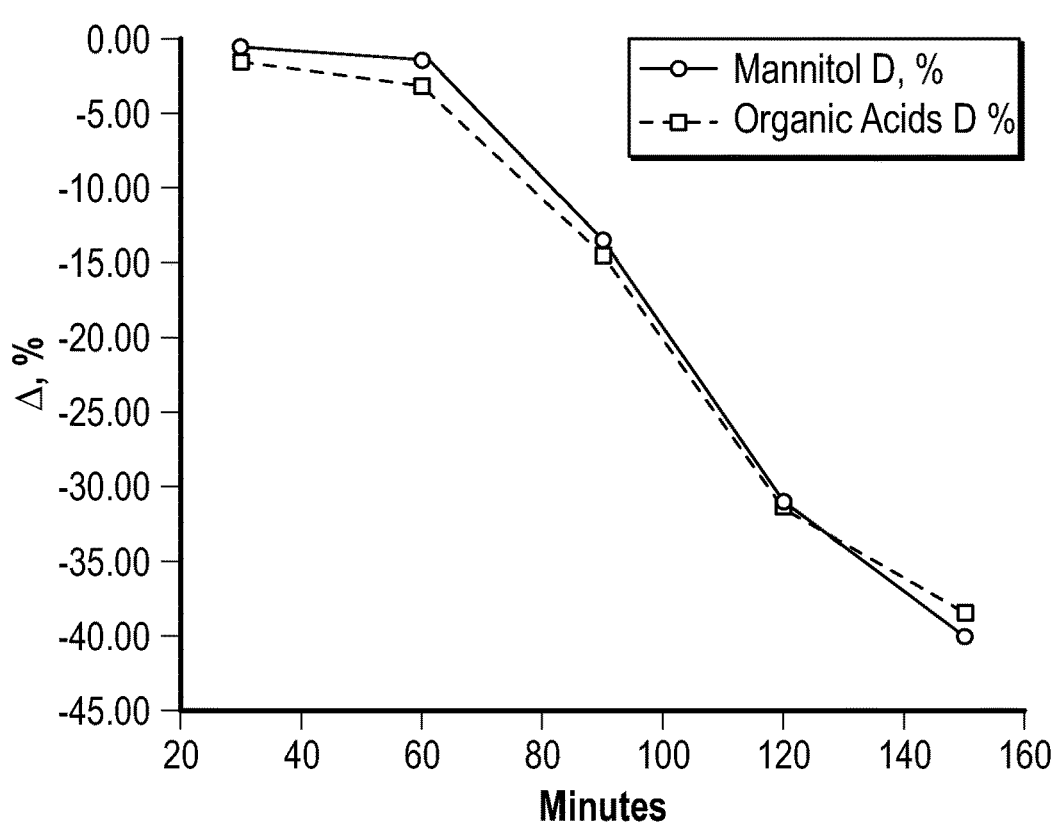
FIG. 18 graphically illustrates removal of contaminants from feed recycled through a nanofiltration unit similar to the unit schematically illustrated in FIG. 1C (with 500 Da membrane using 225 psi where the feed was maintained at 10.4 brix).

FIG. 18 graphically illustrates removal of mannitol and organic acid contaminants from recycled feed (retentate) maintained at 10.4 brix using the AFC30 (500 Da MWCO) nanofiltration unit operated at 225 psi.

Figure 19:
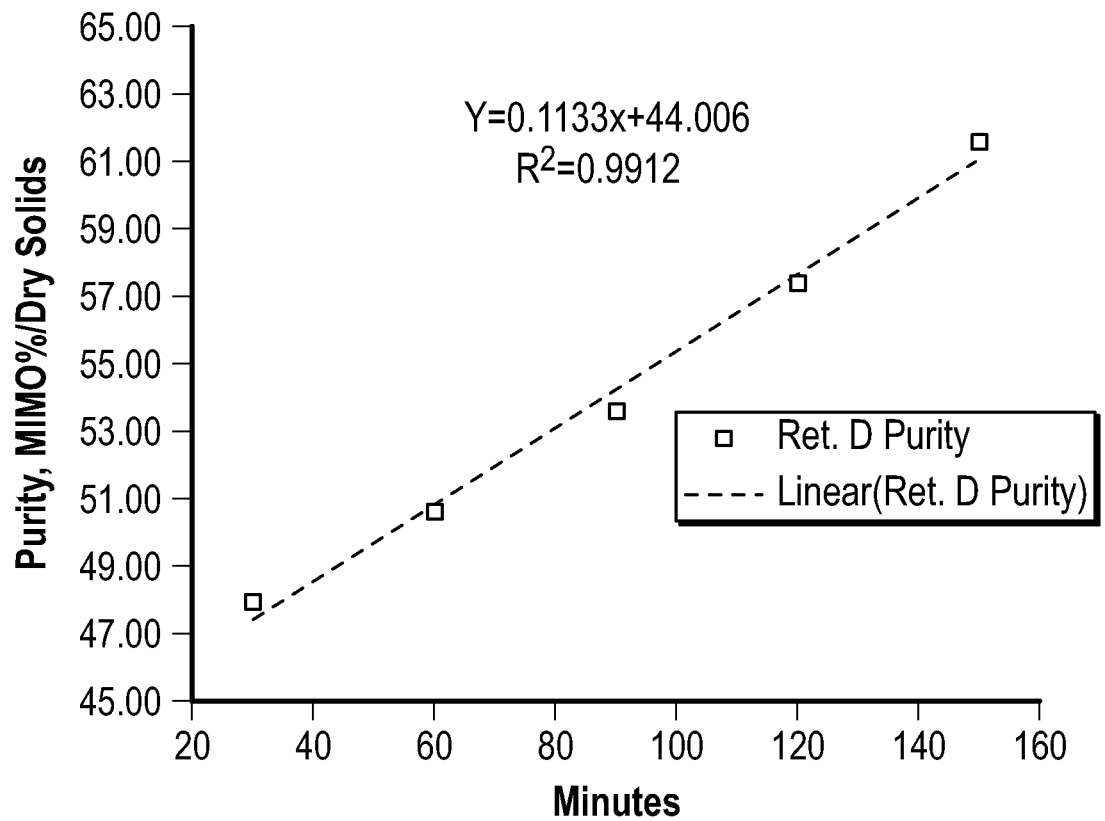
FIG. 19 graphically illustrates MIMO purity of feed recycled through a nanofiltration unit similar to the unit schematically illustrated in FIG. 1C (with 500 Da membrane using 225 psi where the feed was maintained at 10.4 brix).

The purity of MIMOs of the feed recycled (retentate) through the AFC30 (500 Da) membrane at 225 psi is illustrated in FIG. 19 where the feed was maintained at 10.4 brix. The purity as illustrated in FIG. 19 was analyzed via an Agilent 1100 HPLC-RID BioRad HPX-87H (300 mm) column at 65° C., with 0.008N sulfuric acid isocratic at 0.6 mL/min using a differential refractive index detector at 45° C.

Example 8: Example of a Nanofiltration Unit

This Example describes an exemplary nanofiltration unit.

A nanofiltration unit can be approximately 6 feet×4 feet×6 feet (height) not including the membranes. The nanofiltration unit can have membranes with a molecular weight cut-off of less than 182 to 1000, or with a molecular weight cut-off of 450-500. In some cases, about 1-6 membranes can be used, each with surface areas of about 20 square meters. When the membranes are added to the skid the length can become about 13 ft. Other dimensions are also possible.

The nanofiltration unit can be operated at a pressure of 200 psi or more, temperature (55-65° C.), and flux of solids (as related to brix of feed).

The unit may run on 480V, with three phase 60 Hz power. The main draw for power on the unit would be the recirculation pump which could be driven by a 7.5 Horsepower motor. The remaining equipment and sensors may run off a 120V power supply inside a panel. The valves could be electric or pneumatic depending on whether automation is desired. Such a pump motor would have an approximate daily usage of power for an 8-hour day of about 25 kWh.

Other utilities could include warm water for flushing and cleaning. The volume of water employed will vary depending on number of cleans and flushes done. A minimum amount of water would be about 50 gallons.

If going with pneumatic automated valves plant air would be required as well usually at 90 psi.

Example 9: Process for Purifying MIMOs from Fermentation Mixtures

This Example illustrates methods and apparatus for purifying MIMOs after fermentation.

Methods

Methods similar to those described in the foregoing Examples were employed to prepare MIMOs via fermentation. Table 22A and Table 22B summarize processes used for making MIMOs via fermentation.

TABLE 22A

Summary of Fermentation Process

|  | Flask Inoculum | Seed Tank Inoculum | Fermentation |
| --- | --- | --- | --- |
| Volume | 1% v/v of Seed Tank | 1% of Fermenter | per 3,000 Kg working volume; 1 L = slightly more than 1 Kg |
| Process | Flask media (6 L + 1 L sentinel) inoculated with 1% inoculum from vial. | Sugar and salts were pre-mixed and pumped through inline 1.0 μm then 0.2 μm filters. | Sugar and salts were pre-mixed and pumped through inline 1.0 μm then 0.2 μm filters. |
| Process | Transferred to seed fermenter at 16 Hr (no pH control). | Yeast and other ingredients were mixed in the fermenter and sterilized in place (37° C. for 2 hours followed by 121° C. for 60 minutes). | Yeast and other ingredients were mixed in the fermenter and sterilized in place (37° C. for 2 hours followed by 121° C. for 60 minutes). |
| OD | >2.6 | >2.6 | About 13 |
| pH | No pH control | No pH control | pH controlled at 5.5 pH |
| Temp | 27° C. | 27° C. | 27° C. |
| % Sugars; Brix |  | 26% sugars; about 28 brix | 26% sugars; about 28 brix |
| Agitation | Shake flask | Agitated | Agitated |
| Aeration |  | No aeration (not aerobic) | No aeration (not aerobic) |

TABLE 22B

Summary of Fermentation Process II

|  | Flask Inoculum | Seed Tank Inoculum | Fermentation |
| --- | --- | --- | --- |
| Volume | 1% v/v of Seed Tank, all used to inoculate seed fermenter (3 L) | 10% w/w of Fermenter, all used to seed production fermenter (300 L). | per 3,000 L (3,390 kg) working volume |
| Process | Flask media (3 L+ 1 L sentinel) inoculated with 1% inoculum | Sugar and salts were pre-mixed and pumped through inline 1.0 μm then 0.2 μm filters. Yeast and other ingredients were mixed in the fermenter | Sugar and salts were pre-mixed and pumped through inline 1.0 μm then 0.2 μm filters. Yeast and other ingredients were mixed in the fermenter and |

TABLE 22B-continued

Summary of Fermentation Process II

|  | Flask Inoculum | Seed Tank Inoculum | Fermentation |
|---|---|---|---|
|  | from vial. Transferred to seed fermenter at 16 Hr. | and sterilized in place (37° C. for 2 hours followed by 121° C. for 60 minutes). | sterilized in place (37° C. for 2 hours followed by 121° C. for 60 minutes). |
| OD | >2.6 | >10 | >10 |
| pH | No pH control | pH controlled at 5.5 pH | pH controlled at 5.5 pH |
| Temp | 27° C. | 27° C. | 27° C. |
| % Sugars; Brix | 27-29% sugars; about 30 brix | 27-29% sugars; about 30 brix | 27-29% sugars; about 30 brix |
| Agitation | Shake flask | Agitated | Agitated |
| Aeration | Autogenous blanket of CO2 under a sterile plug. | No aeration (not aerobic), up to 5 psig air headspace to maintain positive pressure | No aeration (not aerobic), up to 5 psig air headspace to maintain positive pressure |

Briefly, inoculum flasks were inoculated with 1 mL each of fermentation stock (*Leuconostoc citreum* NRRL B-742; 0.5 mL late-log culture+0.5 mL glycerol, 40%, certified Kosher-Pareve). One flask was anon-inoculated control. The inoculum volume was 1% of the seed tank volume.

The flasks were incubated at 27° C. for 16 Hr ($OD_{600}$ was greater than 2.6) with agitation at 150 RPM. The inoculum was inspected via microscopy to determine the culture was clean prior to use. A sample was taken and frozen at −75° C. in 2% w/w glycerol for later analysis via 16S rRNA sequencing to determine and verify culture purity.

In the meantime, a 1200 gallon seed inoculum tank was cleaned in place. To the seed tank was added reverse osmosis (RO) water, 238 kg; yeast extract, 2.80 kg; potassium phosphate monobasic, 1.50 kg; magnesium sulfate (anhydrous) 0.055 kg; ferrous sulfate heptahydrate, 0.0057 kg; and manganese sulfate monohydrate, 0.0059 kg. The volume of the seed tank was 1% of the volume of the fermentation mixture.

The seed inoculum tank was loaded with RO water, 1510 kg; sucrose, 522.04 kg; maltose monohydrate, 210 kg; sodium chloride, 0.039 kg; and calcium chloride dihydrate, 0.214 kg. The contents of the fermenter were thoroughly mixed, allowed to rest at 37° C. for two hours, and then sterilized in place at 121° C. for 60 minutes.

Once cooled, 310 kg of the sugar and salt solution was transferred from the charge tank to the seed tank through a sterilizing 0.2 μm filter capsule with a 1.0 μm pre-filter (20' Cuno cartridge filter). The filter and lines were washed through with 10 kg of RO water. The mixed medium had a pH of 5.54.

The seed fermenter was inoculated with 3.8 kg late-log flask culture. The fermentation was allowed to proceed under 1-3 psig air (in headspace to maintain positive pressure) at 27° C., with agitation at 42 RPM for 16 hours ($OD_{600}$=2.805, pH 3.45).

In the meantime, the following were added to a cleaned in place production fermenter: RO water, 1332 kg; yeast extract; 5.6 kg; potassium phosphate monobasic, 8.05 kg; magnesium sulfate (anhydrous), 0.2922 kg; ferrous sulfate heptahydrate, 0.030 kg; and manganese sulfate monohydrate, 0.030 kg. The fermentation contents were sterilized in place at 121° C. for 60 mins. The following was pumped into the production fermenter: 1680 kg of the sugar and salt solution (from the charge tank) through a sterilizing 0.2 μm filter capsule with a 1.0 μm pre-filter (20' Cuno cartridge filter). The filter and lines were washed through with 10 kg of RO water.

Thirty-one kg of late-log seed culture was used to inoculate the production fermenter. The pH was adjusted to 6.5 with 50% NaOH, and the fermentation was allowed to proceed for 55 hours at 27° C., with agitation at 31 RPM. The pH was maintained at 5.5 with 50% NaOH (about 120 kg). A sample was taken and frozen at −75° C. in 20% w/w glycerol for later analysis via 16S rRNA sequencing to determine and verify culture purity.

Figure 20:
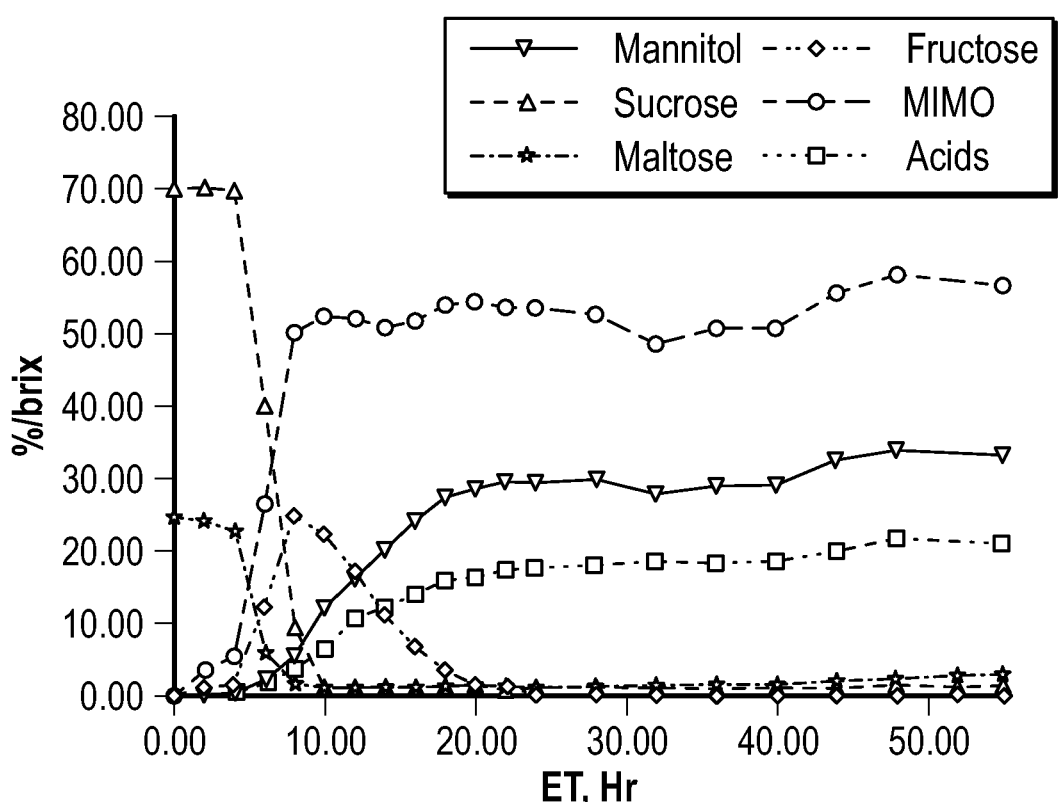
FIG. 20 shows the amounts of chemical species as detected by HPAEC-PAD and HPLC-RID throughout the time course of a 3000 L fermentation (S/M=2.75, lot #151105) using *L. citreum* NRRL B-742.

FIG. 20 shows the amounts of chemical species as detected by HPAEC-PAD and HPLC-RID throughout the course of a 3000 L fermentation (S/M=2.75, lot #151105) using *L. citreum* NRRL B-742.

Figure 21:
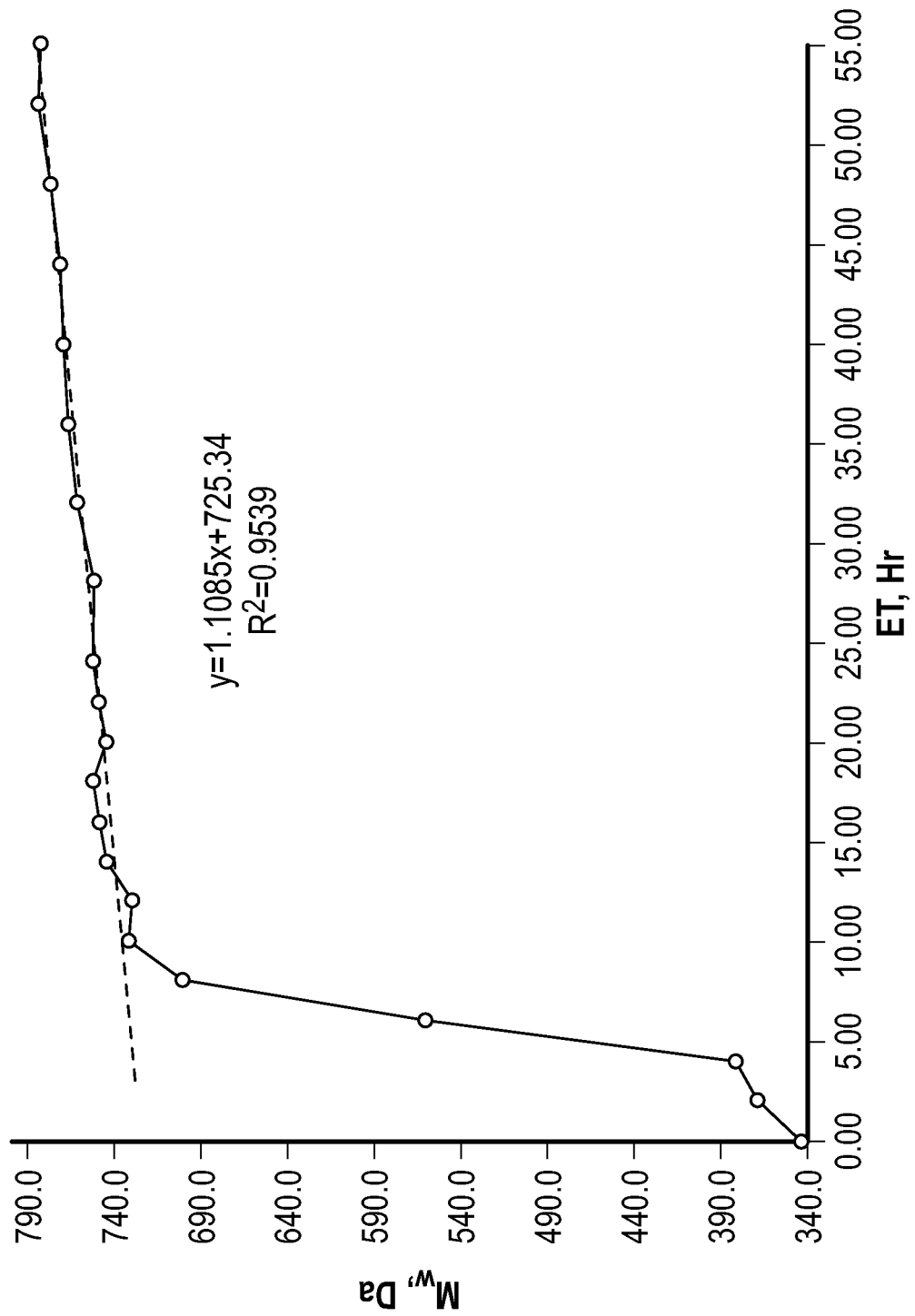
FIG. 21 illustrates the evolution of the mass average molecular weight distribution of MIMOs throughout the course of a 3000 L fermentation (S/M=2.75, lot #151105) with *L. citreum* NRRL B-742. Note that the MWD continues to increase (until about 15 hours) after the sucrose is exhausted (at about 10 hours). The rate of chain growth then takes place at a lower, but constant rate until the end of fermentation (55 hours) when the molecular weight of about 776.5 Da was achieved.

FIG. 21 illustrates the evolution of the molecular weight distribution of MIMOs throughout the course of a 3000 L fermentation (Sucrose:maltose=2.75, lot #151105) with *L. citreum* NRRL B-742. Note the MWD continues to increase (until about 15 hours) after the sucrose is exhausted (at about 10 hours). The rate of chain growth then takes place at a lower, but constant rate until the end of fermentation (55 hours) when the molecular weight of about 776.5 Da was achieved.

Table 23 summarizes cell removal and some of the purification steps that were used to obtain MIMOs from the fermentation broth.

TABLE 23

Initial Product Purification

|  | Cell Removal | Cleanup Step 1 | Cleanup Step 2 |
|---|---|---|---|
| Process | Pre-filtration with 0.2 to 5 micron filter to remove cells. 6-element microfiltration skid 0.2 μm | Nanofiltration tubular crossflow membrane skid 8 elements, 450 to 500 Da pore size (e.g., 450 Da molecular weight cut-off in some cases); | Ion Exchange (IEX) 2-column skid; Single pass followed by water chase |

TABLE 23-continued

Initial Product Purification

| | Cell Removal | Cleanup Step 1 | Cleanup Step 2 |
|---|---|---|---|
| | microfiltration; Filtration plus 6 diafiltrations; Each diafiltration requires 750 Kg $H_2O$. Alternative 1: Cell removal via centrifugation and additional sludge re-watering followed by additional centrifugations depending on desired oligosaccharide yield. All of these are followed by a 1.0 micron then 0.2 micron polishing filter. | filtration plus 1-3 diafiltrations where the volume is equal to the initial feed charge; | |
| Result | | Removes 95% or more of the mannitol, much of ash, organic acids, color, and water. | Removes balance of ash, organic acids, protein, color and odor. |
| Brix | 8 | 30 | 16 |

Note that Cleanup Steps 1 and 2 can be reversed. In other words, nanofiltration can be performed after ion exchange cleanup, before ion exchange cleanup, or both before and after ion exchange cleanup. If an odor and/or color removal step is desired, an activated carbon flow-through filter may be used at any step after cell removal prior to final evaporation and concentration.

The biomass (cells, etc.) was removed from the fermentation broth and the broth was passed through a 0.2 μm microfilter (skid) where the MIMOs were collected in the permeate to produce a cell-free broth.

The cell free broth was subjected to nanofiltration via tubular crossflow membrane skid with eight elements, 500 Da molecular weight cut-off (as described in the foregoing Example; see also FIG. 1C). The MIMOs were retained by the 500 Da molecular weight cut-off filtration unit. The permeate from the nanofiltration unit contained mineral salts, organic acid salts, and mannitol. Very little, if any MIMO passes the 500 Da membrane—thus negating the need for any diafiltration.

The resulting product was passed through strong acid cation (SAC, Purolite C-150S, $H^+$ form, 14 cubic feet) ion exchange resin followed by passage through a weak base anion (WBA, Purolite A-133, free-base form, 13.5 cubic feet) ion exchange resin. The MIMOs were collected in a cleaned in place holding tank and adjusted to pH less than 4.6 with phosphoric acid. For example, the pH can be less than 3.0, or less than 2.8, or less than 2.7, or less than 2.5, or less than 2.4, or less than 2.3, or less than 2.28. In some cases, the pH can be about 2.2 to about 2.4, or about pH 2.28.

The MIMOs were filtered inline through a 0.3 μm filter followed by passage through a 0.2 μm capsule filter (30" PRMXE) and then concentrated via evaporation using a wiped film evaporator, and then discharged hot into 2×1 $m^3$ stainless steel totes. The concentrated MIMO solution was allowed to slowly cool, with slow agitation (pneumatic mixer) to room temperature (25° C.). The MIMO product was pasteurized at 70° C. for 30 minutes in a pot still, cooled and packaged into 55-gallon Scholle bags (Bag in box) with sanitary fittings. The pH of the MIMO product was less than 2.3 (e.g., about pH 2.28) and the brix for the MIMO composition was 65.

Example 10: Optimization of Fermentation Protocol

This Example describes optimization of methods for manufacture of the ISOThrive® product, including:
1. Testing the robustness of fermentations using the maximum amount of process feed sugar.
2. Replacing compound-crystallization and much of the prior ion exchange process with nanofiltration (NF).
3. Increasing inoculum/seed ratio and introducing pH control to the seed fermentation to reduce the time (and increase robustness of the inoculation) required to reach a fructose/mannitol ratio compatible with NF.
4. Increase the sucrose/maltose ratio of the feed to yield the desired MWD in the shortened time.

Note that $M_w$ is used to mean the mass-average molecular weight, which is the statistical average of a distribution of oligomers. The distribution is based on the mass of each oligomer binned by molecular weight—not the number of molecules of each oligomer, which would yield the number-average molecular weight, $M_N$.

1. Increasing the Amount of Process Feed Sugar to a Safe Maximum

Previous work demonstrated that when the total sugars in the medium before inoculation exceeded 29%, the growth rate of the NRRL B-742 (*Leuconostoc citreum*, ATCC 13146) became inversely proportional to increasing concentration of total sugars (when greater than 28%). Therefore 28-29% total sugars (TS) in feed represents the greatest practical increase in yield (from 18.5% TS, a 36% projected increase in product/batch) that is industrially feasible with the B-742 organism. Here, all replicates were conducted near the 29% maximum at 28.85±1.34% total sugars.

2. Materials and Methods:

Five tests were conducted, and four were used to review the effect of inoculation % on induction and growth of molecular weight. Further consideration was given to the fructose/mannitol ratio such that nanofiltration (NF) could reach the concentrations outlined in the product specifications. The effect of inoculation % and seed sucrose:maltose ratio (S/M) on the final $M_W$ was also evaluated.

Apparatus:

Because raising the amount of seed to 10% of the final volume greatly increases the needed amount [e.g. 300 L seed/3000 L (total volume) production], and the test fermentations were carried out at 2 L scale (Eppendorf Celligen-115), a special seed fermenter was constructed using autoclavable 150 mL narrow mouth (12 mm) polypropylene bottles (VWR PN 96400-13; SKU 32829-024), 20 mm butyl rubber septa (MedLab Supply), and RTV silicone (GE Clear, GE500-T 118594). Temperature control was maintained using a 250 mL jacketed beaker (Ace Glass, Inc.; water added to couple the jacket walls to the vessel), water bath (27° C.; Neslab RTE-111), and the thermocouple (TC) connected to the Celligen-115. Stirring was facilitated using a magnetic stir bar autoclaved with the media and coupled with the base included with the Celligen-115. The completed vessels allowed for pH/temperature monitoring, pH control, and stirring, and were operated at a volume of 150 mL. pH and pump output were logged every 30 s and output as comma separated values (csv). Pump output, normally set to 100% with the 2 L vessel using L/S 13 tubing (Masterflex, peroxide cured silicone #96400-13) would overshoot with the 150 mL seed volume. Reducing the pump output to 50% of maximum solved this problem. The amount of seed added to the 2 L fermenter was recorded by mass.

Figure 22:
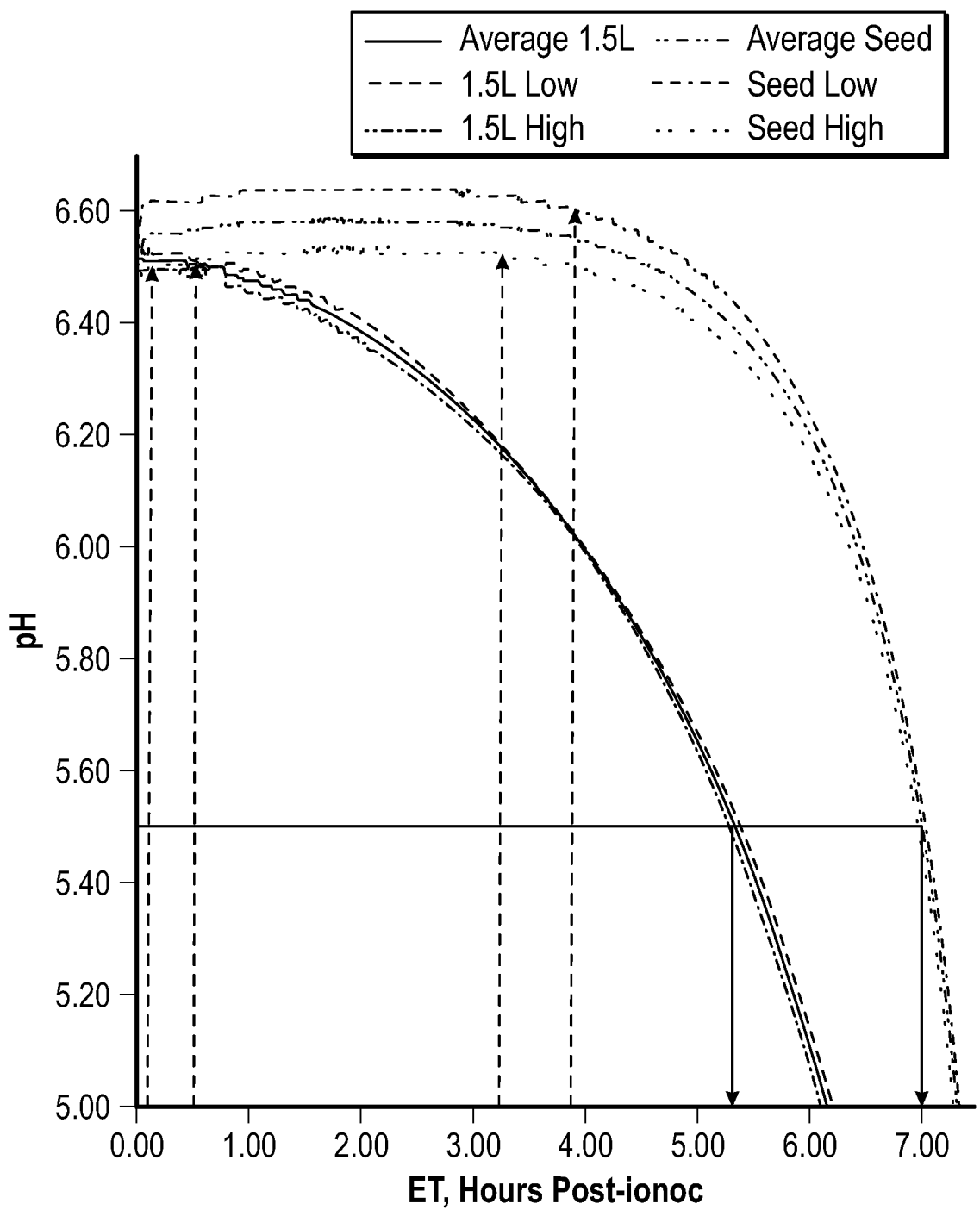
FIG. 22 graphically illustrates log-growth of NRRL B-742 (*Leucontostoc citreum*, ATCC 13146) as a function of pH(t) of seed (150 g) and production (1500 g) fermentations inoculated at 0.642±0.030 and 9.884±0.710%, respectively; N=3.

With the exception of a longer needle to add alkali at the surface of the media (or just below), the final apparatus used for the tests is shown in FIG. 22.

Fermentation:

Several steps were performed before initiation of bulk production fermentation. First, 150 mL of seed started with 1 mL of vial stock was developed (inoculum). The seed was grown for 16 hours, sampled, and then used to inoculate 1,600 mL (total) of media that had also been pre-sampled to check the media composition.

The "production" fermenter was maintained at 27° C. and pH 5.5 for 16-17 hours, with periodic sampling (typically every 2 hr to 25 hrs total), then at 40 hours, and occasionally 60+ hours (for an estimation of "infinite" time). Media components for both seed and "production" fermentations are shown in Table 24. 10× minerals describes a ten-fold concentrate made to contain the same ingredients at the same ratios as those used in our typical media. The 10× mineral solution is used to make very small media batches (such as the 150 mL seed) where individual component quantities would be difficult to weigh.

Each sample was centrifuged (12 kRPM/10 min) to remove biomass, filter sterilized via 0.2 micron membrane (Corning, nylon, 25 mm), and serially diluted for analysis via HPAEC-PAD and HPLC-RID. The components were quantified relative to internal (HPAEC vs. L-arabinose) and external (HPLC) standards. Maltosyl-isomaltooligosaccharides (MIMO) were given as the sum of corresponding oligosaccharides (oligodextran and panose-type) with DP 3 or greater, and molecular weight was calculated statistically as the mass-average of the quantified components. Purity was defined as total MIMO as a percentage of the total mass of components quantified by both means (oligos, sugar alcohols, mono and di-saccharides via HPAEC; confirmation of mannitol and maltose, organic acids, and ethanol via HPLC). Results were expressed as % w/w of dry solids approximated as % w/w over brix. 26 mass-balances closed to 96.53±9.66% indicating that the method was good and was representative of the matrix composition. To improve the quality of comparison, all data sets were normalized to 100% brix.

TABLE 24

Media for Seed and Production Fermentations

| | #1 | #2 | #3 | #5 |
|---|---|---|---|---|
| SEED | | | | |
| Start Date: | Sep. 11, 2018 | Sep. 17, 2018 | Sep. 24, 2018 | Oct. 1, 2018 |
| Sucrose, g: | 0 | 18.31664 | 21.37194 | 31.34886 |
| Maltose-H$_2$O, g: | 0 | 9.89331 | 8.51459 | 11.93739 |
| 10× mineral, g: | 0 | 15.00692 | 15.02823 | 15.00870 |
| yeast ext, g: | 0 | 0.83963 | 0.88538 | 0.88231 |
| water, g: | 150.89000 | 108.14755 | 105.29848 | 105.50013 |
| MRS, g: | 7.11000 | 0 | 0 | 0 |
| inoculum, g: | 1.1 | 1.1 | 1.1 | 1.1 |
| TS, %: | 4.0 | 18.534 | 19.779 | 26.285 |
| Brix: | 4.5 | 21.400 | 21.800 | 21.800 |
| S/M: | n/a | 2.049 | 2.778 | 2.907 |
| PRODUCTION | | | | |
| water, kg: | 0.961 | 0.961 | 0.960 | 0.918 |
| sucrose, kg: | 0.284 | 0.284 | 0.284 | 0.313 |
| Maltose-H$_2$O, kg: | 0.113 | 0.113 | 0.113 | 0.119 |
| yeast ext, kg: | 0.00675 | 0.00677 | 0.00676 | 0.00678 |
| MnSO$_4$—2H$_2$O, kg: | 0.00002 | 0.00002 | 0.00002 | 0.00002 |
| MgSO$_4$, kg: | 0.00018 | 0.00017 | 0.00017 | 0.00017 |
| FeSO$_4$—7H$_2$O, kg: | 0.00002 | 0.00002 | 0.00002 | 0.00002 |
| KH$_2$PO$_4$, kg: | 0.00429 | 0.00424 | 0.00424 | 0.00429 |
| NaCl, kg: | 0.00002 | 0.00002 | 0.00002 | 0.00002 |
| CaCl$_2$—2H$_2$O, kg: | 0.00009 | 0.00010 | 0.00009 | 0.00009 |
| NaOH, 40%, kg: | 0.094 | 0.081 | 0.061 | 0.061 |
| Seed, kg: | 0.158 | 0.140 | 0.140 | 0.162 |
| TS, %: | 28.166 | 25.884 | 26.342 | 29.205 |
| Brix: | 30.700 | 29.100 | 29.100 | 32.100 |
| S/M: | 2.782 | 2.782 | 2.782 | 2.909 |

3. Results

Effect of Inoculation % on Induction Period:

The rate of growth correlates with the accumulation of metabolites. That is, as multiplication of the fermentation organism occurs the pH will drop as organic acids (primarily lactic and acetic) are made. Therefore, entry into log-phase growth is marked by inflection in the pH of the fermentation broth. Logged data from trials 2, 3, and 5 (N=3 each) are shown in FIG. 22, where the seed was inoculated at 0.642 t 0.030% w/w of vial stock and the 1.5 L "production" fermenter was inoculated with 9.884±0.710% w/w of the seed. The vertical arrows in FIG. 22 point to the earliest and latest times at which inflection of pH was noted to occur. A pH control was set to take over and maintain the pH at 5.5 (the optimum for dextransucrase), but there is hysteresis, so the pH can reach 5.0 before the alkali pumps turn on and catch up.

From FIG. 22 it can be observed that the behavior of the pH relative to time is consistent regardless of sucrose: maltose ratio (S/M) or total sugar (TS) % so long as the latter is <30%/brix. Therefore, the rate-behavior of the seed and 1.5 L fermentations should be uniform and relative to the amount of added inoculum.

At 10% (9.9±0.7 w/w) inoculum, the pH inflection occurs between 0.00 and 0.50 hours (essentially immediate) relative to the 3-hour to 4-hour induction time observed when inoculated at 0.64±0.03% w/w. Therefore, a factor of 15.6-fold in inoculation percentage provides a 14-fold reduction in the induction period (about the same fold, or about a log relative to the increased weight of added cells).

Figure 23:
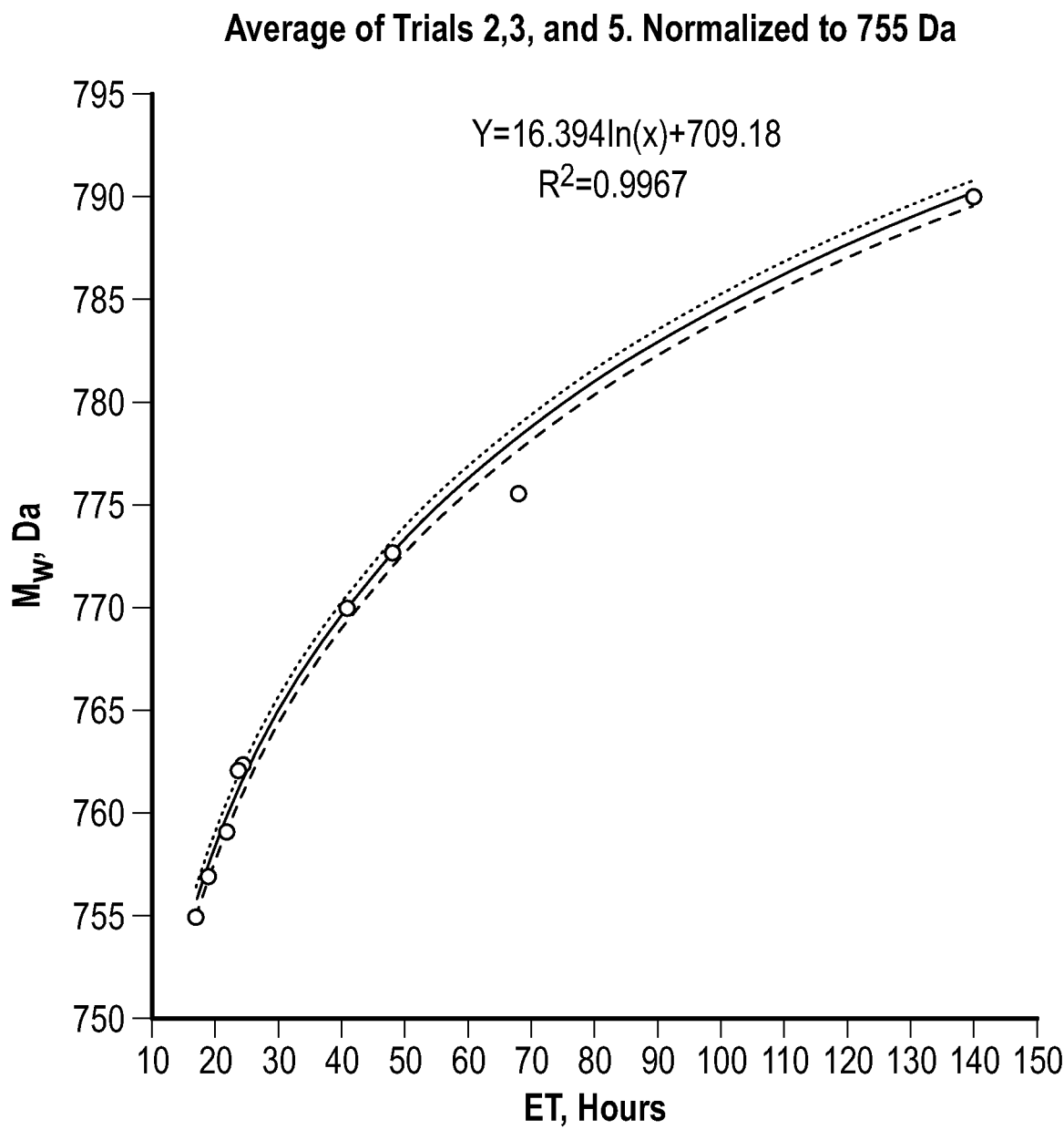
FIG. 23 graphically illustrates the molecular weight of MIMO oligosaccharides as a function of time ($M_w(t)$) relative to the percent of inoculum. Molecular weight developed over time was evaluated, where t=16-140 hours. The graph shows the average of trials 2, 3, and 5 normalized to 755 Da at 16 hours.
Figure 24:
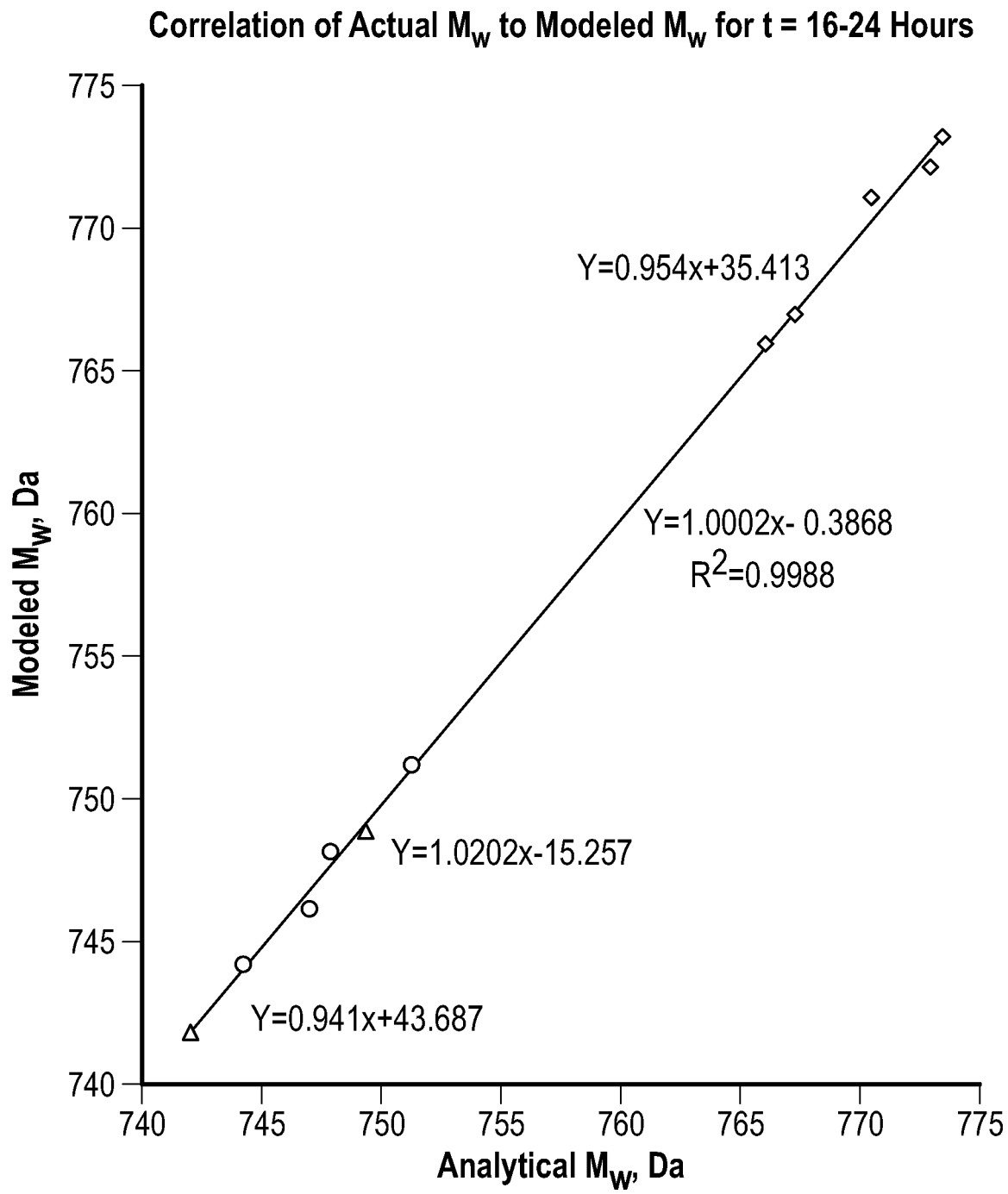
FIG. 24 graphically illustrates the predicted vs. actual molecular weight of MIMO as detected by HPAEC (over three trials).

FIG. 23 graphically illustrates the molecular weight of MIMO oligosaccharides as a function of time ($M_w(t)$) relative to the percent of inoculum. The linear portion of the curve from 16-24 hours was modeled and found to be dependent solely upon starting molecular weight (dependent on S/M and pH) and time. The molecular weight at 16 hours can be used to predict the molecular weight at any time within the fitted period (FIG. 23). The equation for this is given below, and a correlation plot of predicted values vs. actual values (HPAEC) are shown in FIG. 24.

$$M_w = \frac{(1.0182 * t_{hr} + 737.69) * M_{w16hr}}{755}$$

The correlation of predicted vs. actual Mw for all of the points was good ($R^2$=0.9988) and the bias was small (−0.3866) suggesting that the model is good for all of the data in the range of 16-24 hours.

These data indicate that the rate of molecular weight development can be offset by slow consumption of MIMO by what appears to be an extracellular hydrolytic enzyme. The rate of MIMO consumption is inversely proportional to oligomer molecular weight and the rate is the same regardless of the percent weight of inoculum so long as the fermentation has entered log growth. However, the induction period is dependent on the percent inoculum, even though the rate of molecular weight evolution is not. Hence yield can decrease as molecular weight increases.

Figure 25:
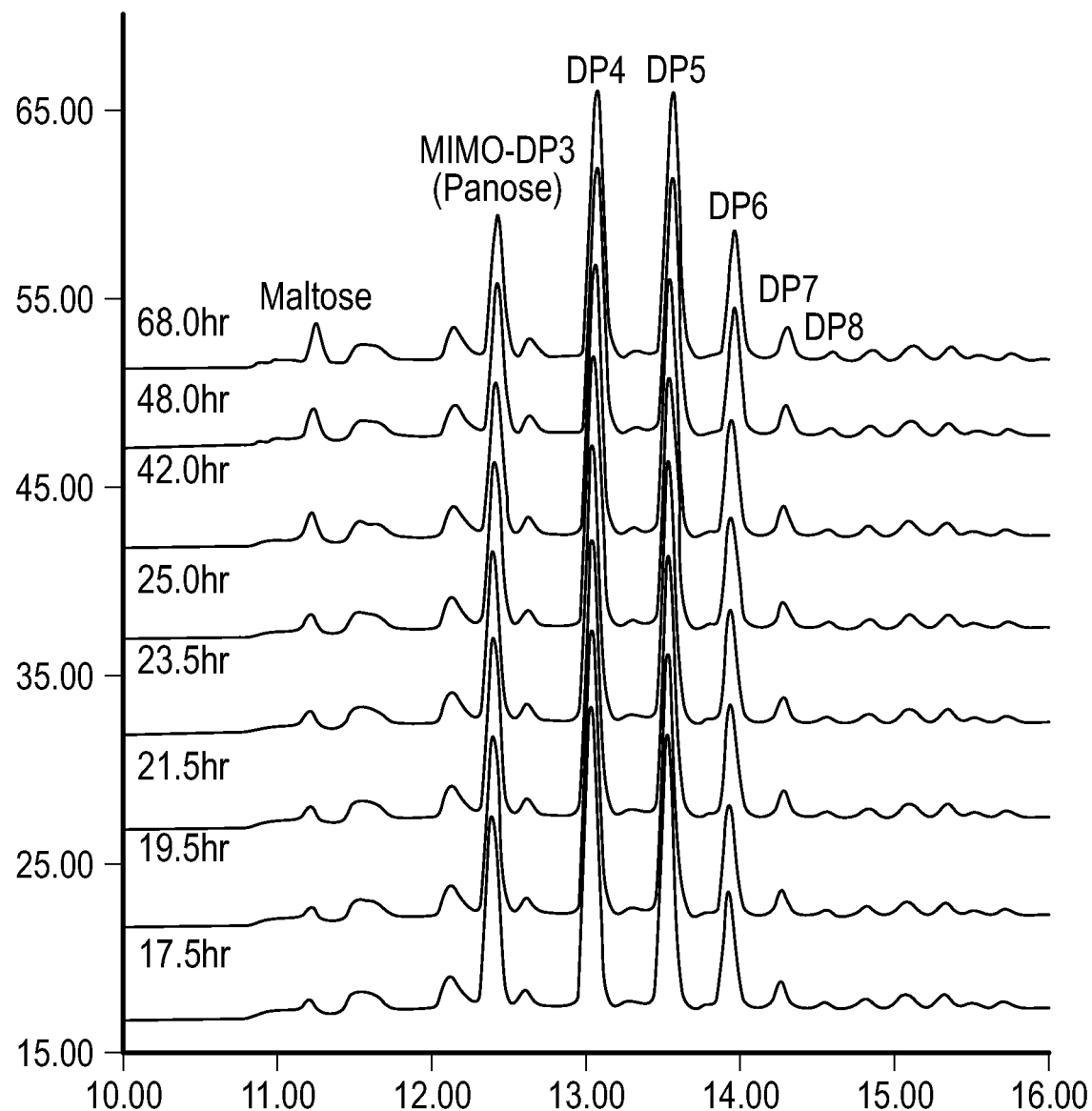
FIG. 25 shows HPAEC chromatograms from trial #5 illustrating the degree of polymerization (DP) of oligosaccharides at various time points during fermentation. Note that when the panose content decreases, the maltose content increases over time.

These data also shed light on the mechanism behind the observed increase in molecular weight over time. Take up of alkali is slow as time proceeds and the enzymatic activity drops off as a function of chain length (DP). As shown in FIG. 25, while the molecular weight increases, the purity of the MIMO decreases and the maltose content increases. Such observations indicate that some of the MIMO may be enzymatically degraded by hydrolytic extracellular enzyme. The glucose content does not increase, however. Instead, glucose does not begin to accumulate until around 65 hours (0.00-0.94% between 65-140 hr), so the culture was still metabolically active, albeit slowly, until that point. The culture is non-viable after about 65 hours. The lower glucose content during earlier times of fermentation may occur, for example, because some glucose may still be added to the oligosaccharide chains. As indicated in FIG. 25, the DP >6 oligosaccharides appear to be increasing over time. However, the panose is destroyed relatively quickly. Hence, even while the longer oligosaccharide chains appear to increase over time, the shorter oligosaccharide chains such as panose may be enzymatically hydrolyzed.

Figure 26:
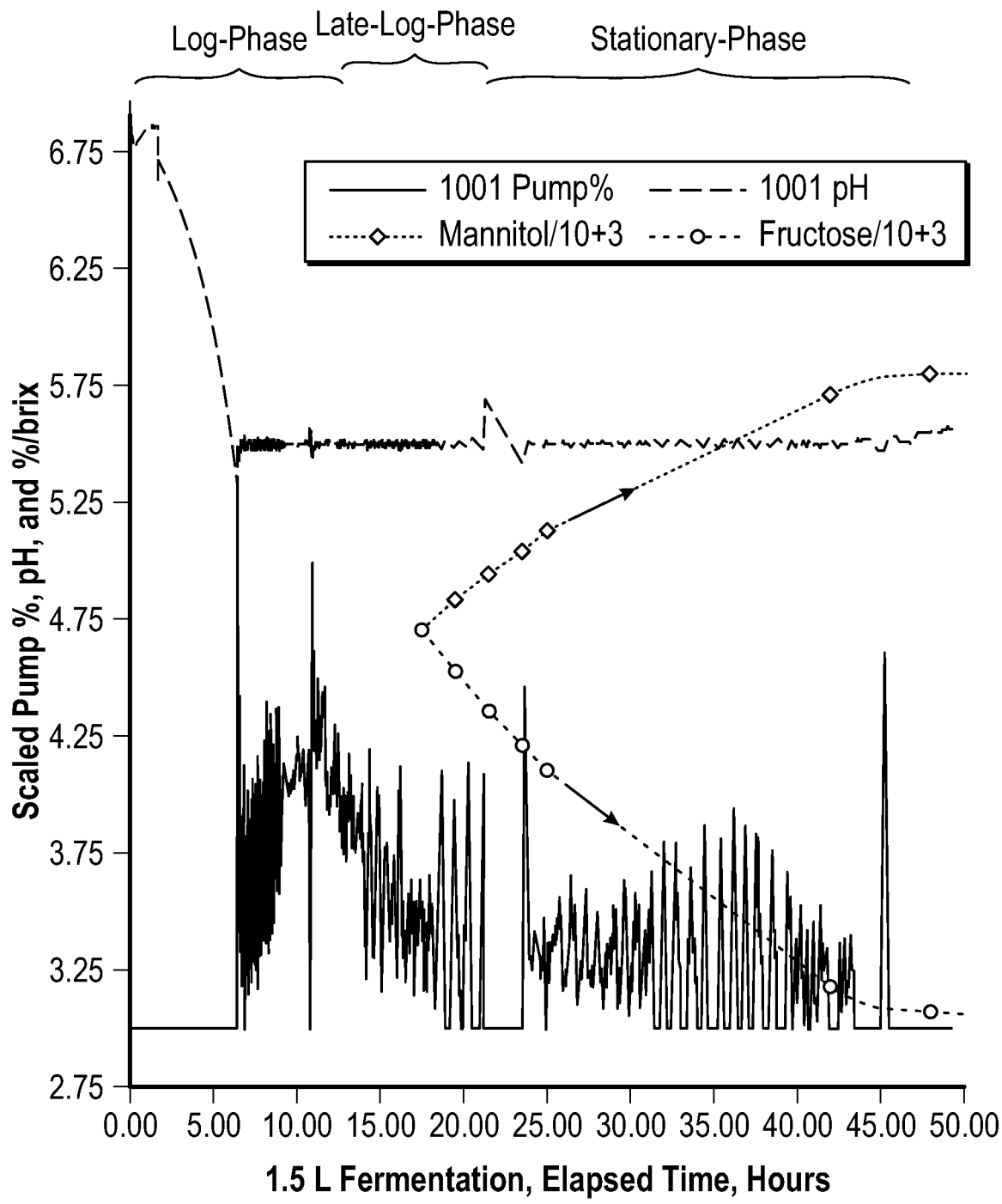
FIG. 26 graphically illustrates pH, pump output, mannitol, and fructose (the latter three scaled for appearance) for trial #5. The pump activity (bottom) and pH (top) illustrate the phase of growth and the stoichiometric metabolic activity. Conversion of fructose (down-arrow) relative to mannitol (up-arrow; remainder of bulk metabolism) is overlaid to show when the fermentation is essentially complete.

FIG. 26 shows plot of pH, pump output, mannitol, and fructose (the latter three scaled for appearance) for trial #5. The pump activity (bottom of FIG. 26) and the pH (top of FIG. 26) provide a measure of the phase of growth and stoichiometric metabolic activity of the culture. Conversion of fructose (down-arrow in FIG. 26) to mannitol (up-arrow in FIG. 26) provide a measure of the degree of conversion. The fructose and mannitol levels show when fermentation is essentially complete.

Figure 27:
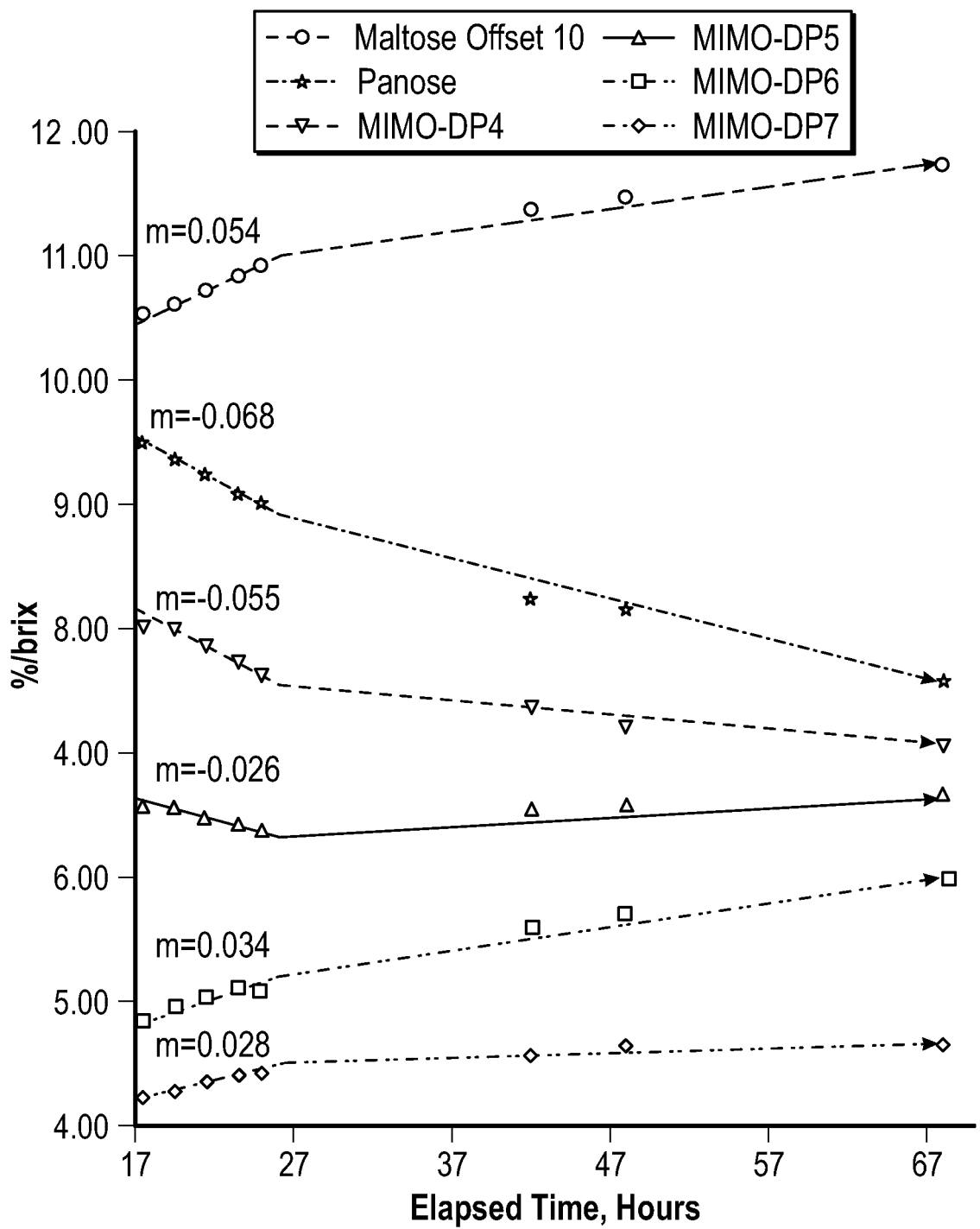
FIG. 27 graphically illustrates hydrolysis of MIMO to yield maltose and an inverse relationship between rate of hydrolysis and degree of polymerization, providing at least one reason why achieving an optimal MIMO mass average molecular weight distribution (MWD) in a shorter time is desirable.

FIG. 27 graphically illustrates the susceptibility to hydrolysis of MIMO as indicated by the degree of polymerization (DP), and the accumulation of maltose.

Figure 28:
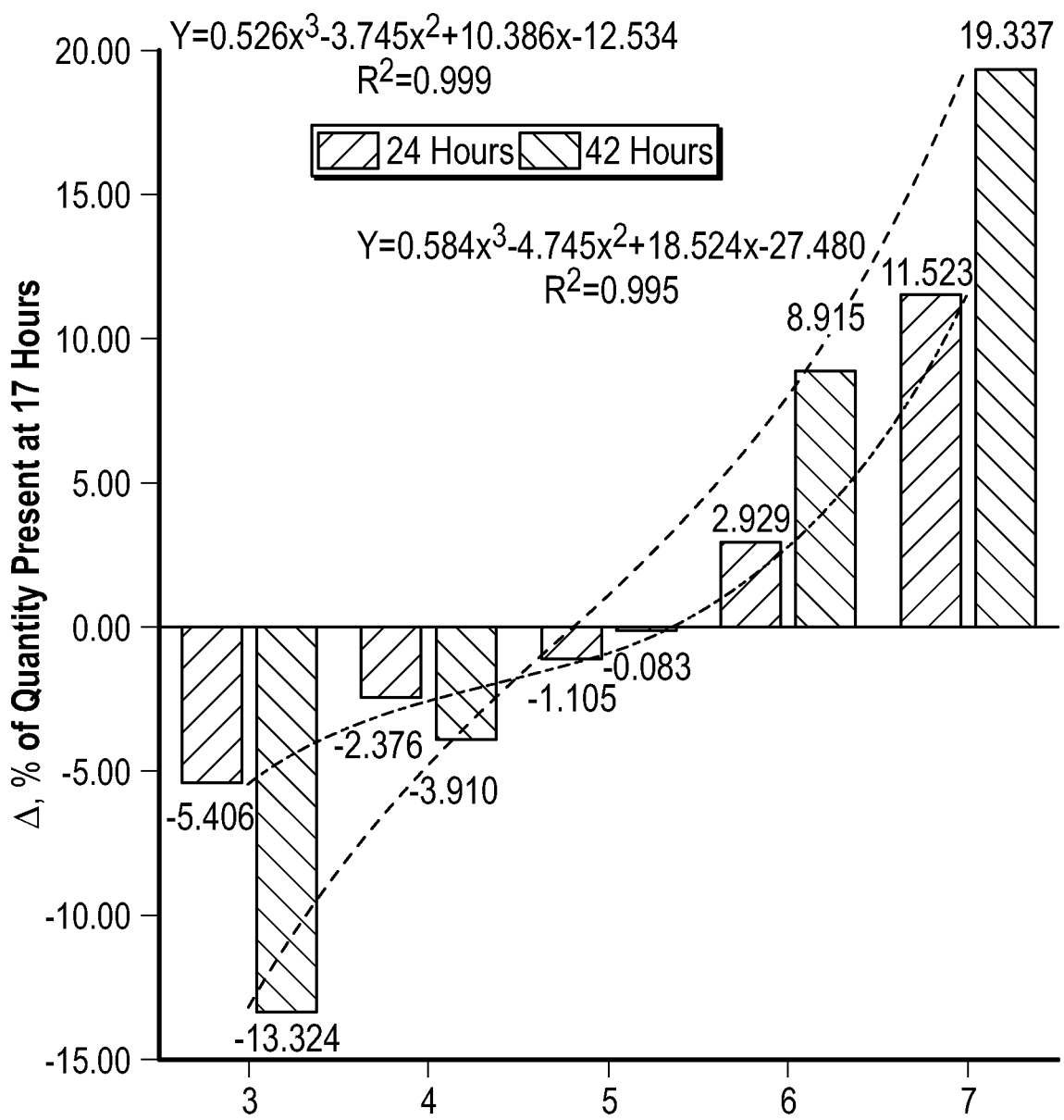
FIG. 28 graphically illustrates the changes in quantities of MIMOs with DP 3-7 at 25 hours (black) and 42 hours (gray) after initiating fermentation by addition of the inoculum relative to the initial quantity measured at 17 hours post-inoculation.

FIG. 28 shows a relationship between susceptibility to hydrolysis, described as the amount of DP3-DP7 (numbers along the x-axis) at 25 hours (black) and 42 hours (gray) after initiating fermentation by addition of the inoculum relative to the initial quantity measured at 17 hours post-inoculation time. It can be seen that DP 5 appears to be the break-even point at 43 hours where little or no change in DP5 levels occurs compared to low levels of hydrolysis evident at 24 hours. Relatively profound decreases in amounts of DP 3 and DP4 oligosaccharides, which occur at both 24 hours and 42 hours. The susceptibility of DP 3 and DP 4 at 24 and 42 hours, relative to DP 5, were observed to be 4.89/160.6 and 2.27/3.40, respectively.

In view of the nature of a dextransucrase producing organism, the hydrolytic enzyme may be a disaccharidase, for example a sucrase, that is sufficiently promiscuous to hydrolyze DP 3-DP 5 oligosaccharides, albeit at a slower rate than sucrose is hydrolyzed, which occurs quickly. The digestibility of various oligosaccharides by sucrase/isomatase in the small intestine may therefore be inversely proportional to DP.

Significance of Lower Yields as Relating to Greater $M_w$

Figure 29:
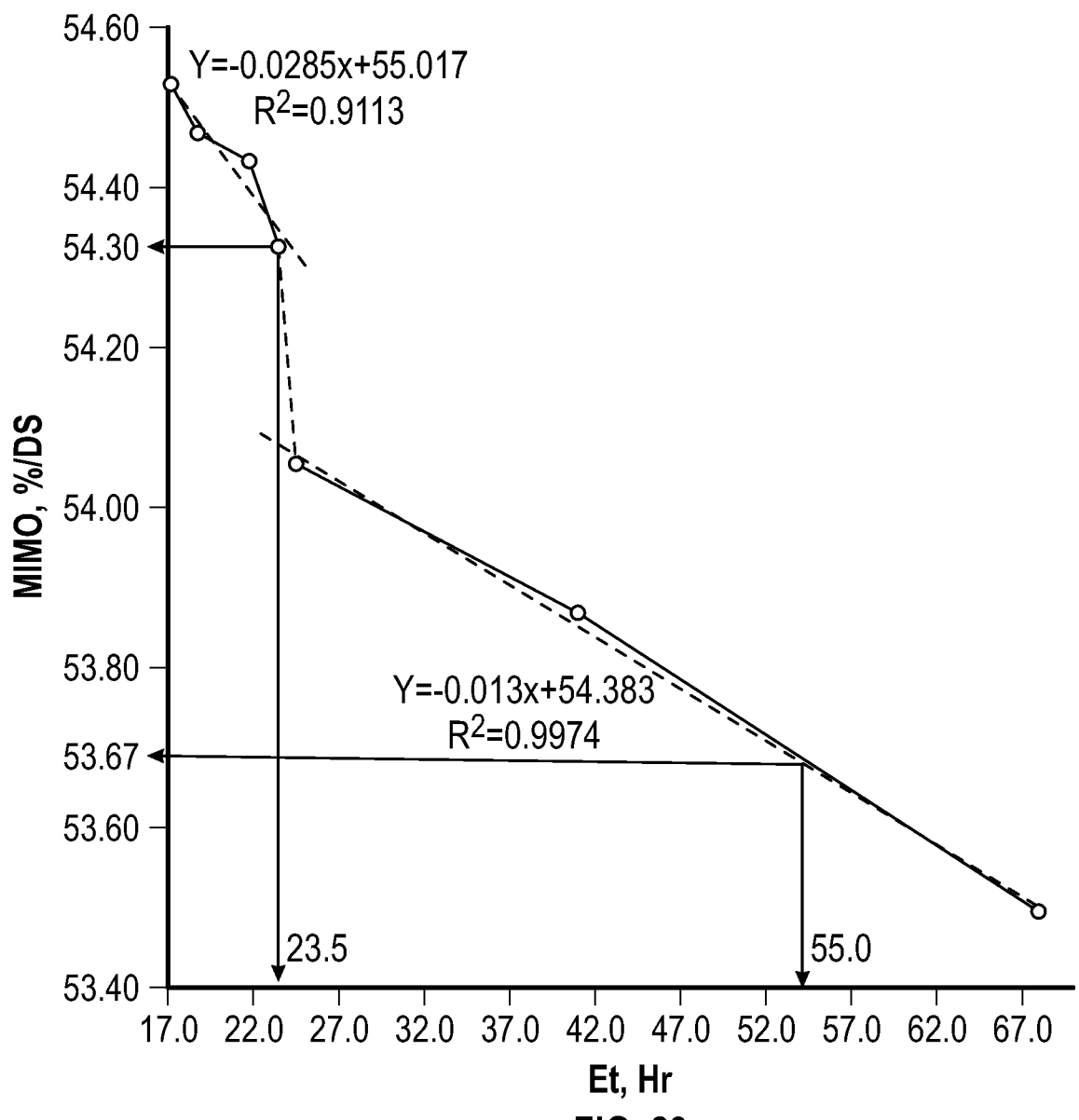
FIG. 29 graphically illustrates MIMO yield as a function of fermentation time. Note the improvement in yield when the fermentation is terminated at 23.5 hours relative to the usual protocol of waiting for molecular weight ($M_w$) maturation until 55 hours. Note also that the mechanisms and rates of change differ at the point of transition from late-log to stationary-phases of growth. Uptake of alkali is typically too slow to observe in the region of 25-67 hours.

Hydrolysis of DP 3-4 appears to be a significant mechanism behind $M_w$ maturation, and, as demonstrated above, also of the lower yields that can result. FIG. 29 shows typical yield of MIMO overtime (Trial #5) for bulk ISOThrive® fermentation using the newer process described in this Example. Note that MIMO yield decreases from about 54.5 to 54.3 (i.e., only −0.2) % yield when harvesting at 23.5 hours, compared to a reduction of about −0.8% that can occur if the fermentation continued to 55 hours. Such a difference amounts to a loss of perhaps $39,000 worth of product.

A summary of trial variables and results are shown in Table 25.

TABLE 25

Trial variables and relevant results.

|  |  | Trial | | | | | |
|---|---|---|---|---|---|---|---|
|  |  | #1 | #2 | #3 | #5 | | |
|  | Start Date: | Sep. 11, 2018 | Sep. 17, 2018 | Sep. 24, 2018 | Oct. 1, 2018 | Average: | Stdev: |
| SEED | TS, %: | 4.00 | 18.53 | 19.78 | 26.29 | 21.53 | 4.16 |
|  | Brix: | 4.50 | 21.40 | 21.80 | 21.80 | 21.67 | 0.23 |
|  | S/M: | n/a | 2.05 | 2.78 | 2.91 | var | var |
|  | Total, kg: | 0.159 | 0.153 | 0.152 | 0.166 | 0.158 | 0.006 |
| PRODUCTION | Inoculum, %: | 0.691 | 0.718 | 0.723 | 0.664 | 0.699 | 0.027 |
|  | MIMO, %: | 0.00* | 51.78 | 50.24 | 53.41 | 51.81 | 1.584 |
|  | $M_W$, Da: | 342.0 | 673.9 | 743.0 | 769.6 | var | var |
|  | Brix: | 30.70 | 29.10 | 29.10 | 32.10 | 30.25 | 1.446 |
|  | S/M: | 2.78 | 2.78 | 2.78 | 2.91 | var | var |
|  | Total, kg: | 1.621 | 1.590 | 1.569 | 1.584 | 1.591 | 0.022 |
|  | MIMO, %**: | 52.79 | 54.91 | 52.92 | 54.33 | 53.74 | 1.046 |
|  | $M_W$, Da: | 848.92 | 749.36 | 751.22 | 770.47 | var | var |

*MRS (De-Man, Rogosa and Sharpe) media contains neither sucrose nor maltose.
**Sum of all MIMO products with DP 3+. Final Mw of trial #1 was at 40 hours, calculated $M_w$ at 24 hours is 841.1 Da.

The data in Table 25 indicates that fermentation for 23-24 hours is optimal in terms of fructose content, and that a sucrose:maltose ratio of 2.9 is sufficient to reach the target $M_w$ range at that time or at a time that is somewhat shorter (the error of the analytics is about ±10 Da), where the average target $M_w$ range is about 770.

The yields in view of the seed inoculum are higher than usual, for example 51.81 relative to about 48% (as total % MIMO of the dry solids (DS)). This improvement carries into the bulk fermentation, which is likewise improved, to yield 54.10% MIMO, which represents an improvement of about +6%, overall. The four 1.5 L fermentations (excluding the seed in MRS media in trial #1) demonstrated adequate reliability for reproducible yields when conducted at approximately 30.3 brix (28-29% total sugar).

4. Feasibility:

|  | New: | New brix, old yield | Old: |
|---|---|---|---|
| Ferm, L total: | 15000 | 15000 | 15000 |
| Ferm, kg total: | 16920 | 16920 | 16920 |
| TS, %: | 29 | 29 | 18.5 |
| TS, kg: | 4906.8 | 4906.8 | 3130.2 |
| Yield, %: | 54.30 | 48.70 | 48.70 |
| product/ferm, kg: | 2664.2 | 2389.6 | 1524.4 |
| Recovery, %: | 52.3 | 44 | 44 |
| product/rec., kg: | 2566.3 | 2159.0 | 1377.3 |
| Syrup, kg: | 3830.2 | 3222.4 | 2055.7 |
| Syrup, 67°, L: | 2946.33 | 2478.75 | 1581.27 |
| Doses: | 2104524 | 1770537 | 1129481 |
| Boxes: | 70151 | 59018 | 37650 |
| $/batch: | 2805338.49 | 2360129.82 | 1505623.50 |
| Improvement, $: | 445208.67 | 854506.32 | 0.00 |
| Total improved, $: | 1299714.99 |  |  |

5. Observations:

Increasing the inoculation % decreases the fermentation induction period. At 10% w/w inoculum, entry to log-growth is essentially immediate, perhaps 15-30 minutes post inoculation. In general, the increase in rate follows the increase in %, where an increase in the % w/w inoculum leads to a decrease % induction per hour of approximately 1:1.

To obtain and control for a targeted MWD within a predictable timeframe, pH control of the seed inoculum is desirable, especially when the seed is added at 10% w/w of the fermentation fluid. Alternatively, if seed organisms are grown at pH <5.5, as would be the case in an uncontrolled fermentation, then the $M_w$ of the product within the seed fermentation broth will be very low and consist mostly of shorter oligosaccharide chains such as panose (DP 3) which would unduly skew the MWD to an undesirably lower value.

Controlling the pH at 5.5 throughout (i.e. within Seed and Production fermenters) therefore keeps the $M_w$ of the manufactured MIMO consistent and predictable, and increasing the S/M can give the desired $M_w$ in less time (where 19-24 hours appears to be optimal for the new process-flow using nanofiltration).

The rate of $M_w$ evolution is remarkably consistent, regardless of the initial sugar concentration or S/M. The $M_w$ at any time (up to 25 hr) can be predicted if the $M_w$ at 16-17 hr is known using the equation ($R^2$=0.9988):

$$M_w = \frac{(1.0182 * t_{hr} + 737.69) * M_{w16hr}}{755}$$

However, as the molecular weight of the MIMO increases during fermentation, the purity of the MIMO decreases. Such a decrease in purity is likely due to hydrolysis of MIMO to yield maltose, which accumulates along with glucose, where the glucose is consumed in production of more oligosaccharides. As lower DP are removed, the MWD shifts toward higher DP (albeit a lower total % mass of the total). After about 65 hours, evidence of metabolism ceases, and both glucose and maltose can be observed to increase as $M_w$ continues to rise.

The hydrolysis rate is inversely proportional to oligomer chain length and decreases as DP 5 becomes more prevalent. The DP 6+ oligosaccharides did not appear susceptible. Therefore, the $M_w$ development occurs at the expense of MIMO DP 3-5 hydrolysis.

Released glucose is consumed until the culture becomes non-viable around 65 hours. Conversion of MIMO, as evidenced by increases in $M_w$, was unabated, but some of the smaller MIMO molecules are slowly broken down. Therefore, it appears that a hydrolase enzyme (either weakly active or very low concentration, or both) remains active against is active against DP3-5 oligosaccharides after metabolism ceases.

An ideal molecular weight of 760-780 Da can be observed when fermenting with a 2.9:1 sucrose to maltose ratio and harvesting at 23-25 hours. An ideal ratio of fructose and mannitol (~1.69:1 or 20.4:12.1%/brix) can be observed at 23.5 hours and can be predicted using the following equation ($R^2$=0.9969): where mannitol/fructose=$0.0958e^{0.1249t,hr}$, $$\frac{Mann}{fru} = 0.0958e^{0.1249t,hr}$$

REFERENCES

1. Kuriki, T., Yanase, M., Takata, H., Takesada, Y., Imanaka, T. and Okada, S. (1993). A New Way of Producing Isomalto-Oligosaccharide Syrup by Using the Transglycosylation Reaction of Neopullalanase. Appl. Env. Microbiol. 59 (4), pp. 953-959.
2. Sakano, Y., Kogure, M., Kobayashi, T., Tamura, M. and Suekane, M. (1978). Carbohydrate Res. 61 (1), pp. 175-179.
3. Brooker, B. E. (1977). Ultrastructural Surface Changes Associated with Dextran Synthesis by Leuconostoc mesenteroides. J. Bacteriol. 131 (1), pp. 288-292.
4. Robyt, J. F., Yoon, S-H., and Mukerjea, R. (2008). Dextransucrase and the mechanism for dextran biosynthesis. Carbohydr. Res. 343 (18), pp. 3039-3048.
5. Kothari, D. and Goyal, A. (2015). Enzyme-resistant isomalto-oligosaccharides produced from Leuconostoc mesenteroides NRRL B-1426 dextran hydrolysis for functional food application. Biotechnol. Appl. Biochem. Published online 21 Sep. 2015. DOI: 10.1002/bab.1391.
6. Hu, Y., Ketabi, A., Buchko, A., and Ganzle, M. G. (2013). Metabolism of isomalto-oligosaccharides by Lactobacillus reuteri and bifidobacteria. Lett. Appl. Microbiol. 57, pp, 108-114.
7. Moller, M. S., Fredslund, F., Majumder, A., Nakai, H., Poulsen, J-C., N., Leggio, L. L., Svensson, B., and Hachem, M. A. (2012). Enzymology and Structure of the GH13_31 Glucan 1,6-a-Glucosidase That Confers Isomaltooligosaccharide Utilization in the Probiotic Lactobacillus acidophilus NCFM. J. Bacteriol. 194 (16), pp. 4249-4259.
8. Dols, M., Chraibi, W., Remaud-Simeon, M., Lindley, N. D., and Monsan, P. F. (1997). Growth and Energetics of Leuconostoc mesenteroides NRRL B-1299 during Metabolism of Various Sugars and Their Consequences for Dextransucrase Production. Appl. Env. Microbiol. 63 (6), pp. 2159-2165.
9. Dols, M., Remaud-Simeon, M., Willemot, R. M., Vignon, M. and Monsan, P. (1998). Appl. Env. Microbiol. 64 (4), pp. 1298-1302.
10. Cho, S. K., Eom, H. J., Moon, J. S., Lim, S. B., Kim, Y. K., Lee, K. W. and Han, N. S. (2014). An improved process of isomaltooligosaccharide production in kimchi involving the addition of a Leuconostoc starter and sugars. Int. J. Food Microbiol. 170, pp. 61-64.
11. Tieking, M., Korakli, M., Ehrmann, M. A., Ganzle, M. G., and Vogel, R. F. (2003). In situ Production of Exopolysaccharides during Sourdough Fermentation by Cereal and Intestinal Isolates of Lactic Acid Bacteria. Appl. Env. Microbiol. 69 (2), pp. 945-952.
12. Corsetti, A. and Settanni, L. (2007). Lactobacilli in sourdough fermentation. Food Res. Int. 40, pp. 539-558.
13. Lee, M-E., Jang, J-Y., Lee, J-H., Park, H-W., Choi, H-J. and Kim, T-W. (2015). Starter Cultures for Kimchi Fermentation. J. Microbiol. Biotechnol. 25 (5), pp. 559-568.
14. Mozzi, F., Vaningelgem, F., Hebert, E-M., Van der Meulen, R., Foulquie Moreno, M. R., Font de Valdez, G., and De Vuyst, L. (2006). Diversity of Heteropolysaccharide-Producing Lactic Acid Bacterium Strains and Their Biopolymers. Appl. Env. Microbiol. 72 (6), pp. 4431-4435.
15. Madsen II, L. R., Adams, K. L. and Gillevet, P. (2014). High-throughput PCR Sequencing of 16S rRNA in an Auto-inoculated, unfortified Sourdough starter From Red Wheat Flour. Unpublished in-house R&D work.
16. Madsen II, L. R. and Stanley, S. (2015). Fermentation using NRRL B-1299 to produce Maltosyl-isomaltooligosaccharides: analysis of 20 L fermentation broth via HPAEC-PAD. Unpublished in-house R&D work.
17. Patel, S., Kothari, D. and Goyal, A. (2011). Purification and Characterization of an Extracellular Dextransucrase from Pediococcus pentosaceus Isolated from Soil of North East India. Food. Technol. Biotechnol. 49 (3), pp. 297-303).
18. Dols-Lafargue, M., Willemot, R-M., Monsan, P. F. and Remaud-Simeon, M. (2001). Factors Affecting a-1,2 Glucooligosaccharide Synthesis by Leuconostoc mesenteroides NRRL B-1299 Dextransucrase. Biotechnol. Bioeng. 74 (6), pp. 498-504.
19. Chludzinski, A. M., Germaine, G. R. and Schachtele, C. F. (1974). Purification and Properties of Dextransucrase from Streptococcus mutans. J. Bacteriol. 118 (1), pp. 1-7.
20. Miller, A. W., Eklund, S. H. and Robyt, J. F. (1986). Milligram to gram scale purification and characterization of dextransucrase from Leuconostoc mesenteroides NRRL B-512F. Carbohydr. Res. 147 (1), pp. 119-133.
21. Goyal, A., Nigam, M., and Katiyar, S. S. (1995). Optimal conditions for production of dextransucrase from Lecuonostoc mesenteroides NRLL (NRRL) B-512F and its properties. J. Basic Microbiol. 35 (6), pp. 375-384.
22. Sarwat, F., Ul Qader, S-A., Aman, A. and Ahmed, N. (2008). Production & Characterization of a Unique Dextran from an Indigenous Leuconostoc mesenteroides CMG713. Int. J. Biol. Sci. 4 (6), pp. 379-386.
23. Monchois, V., Reverte, A., Remaud-Simeon, M., Monsan, P. and Willemot, R-M. (1998). Effect of Leuconostoc mesenteroides NRRL B-512F Dextransucrase Carboxy-Terminal Deletions on Dextran and Oligosaccharide Synthesis. Appl. Env. Microbiol. 64 (5), pp. 1644-1649.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements describe and summarize various embodiments of the invention according to the foregoing description in the specification.

Statements:
1) A method comprising:
   a. providing a fermentation broth comprising maltosyl-isomaltooligosaccharides, dextransucrase/alternansucrase-producing microorganisms, and culture media;
   b. removing the microorganisms from the fermentation broth to produce a cell-free fermentation broth;
   c. passing the cell-free fermentation broth through at least one 200 dalton to 700 dalton molecular weight cut-off nanofiltration unit to produce a first nanofiltered product.

2) The method of statement 1, further comprising passing the cell-free fermentation broth through a carbon filter to produce a carbon-filtered product that is passed through at least one 200 dalton to 700 dalton molecular weight cut-off nanofiltration unit to produce a nanofiltered and carbon filtered product.

3) The method of statement 1, further comprising passing the first nanofiltered product through a carbon filter to provide a nanofiltered and carbon filtered product.

4) The method of statement 1, 2 or 3, further comprising passing the cell-free fermentation broth, the carbon-filtered product, the first nanofiltered product, or the nanofiltered and carbon filtered product through a strong acid cation exchange resin to produce a first ion exchange treated product.

5) The method of statement 1-3, or 4, further comprising passing the cell-free fermentation broth, the carbon-filtered product, the first nanofiltered product, the nanofiltered and carbon filtered product, or the first ion exchange treated product through a weak base anion exchange resin to produce a second ion exchange treated product.

6) The method of statement 4 or 5, further comprising passing the first ion exchange treated product or the second ion exchange treated product through at least one 200 dalton to 700 dalton molecular weight cut-off nanofiltration unit to produce a second nanofiltered product.

7) The method of statement 1-5, or 6, further comprising adjusting pH of the first nanofiltered product, the second nanofiltered product, the nanofiltered and carbon filtered product, the first ion exchange treated product, or the second ion exchange treated product to a pH less than 5.5 to produce a pH adjusted product.

8) The method of statement 1-6, or 7, further comprising concentrating the nanofiltered product, nanofiltered and carbon filtered product, first ion exchange treated product, the second ion exchange treated product, or the pH adjusted product produce a concentrated MIMO product.

9) The method of statement 1-7, or 8, further comprising filtering the nanofiltered product, the nanofiltered and carbon filtered product, the first ion exchange treated product, the second ion exchange treated product, the pH adjusted product, or the concentrated MIMO product through a microfilter to produce a microfiltered product.

10) The method of statement 1-8, or 9, further comprising pasteurizing the nanofiltered product, the nanofiltered and carbon filtered product, the first ion exchange treated product, the second ion exchange treated product, the pH adjusted product, the concentrated MIMO product, or the microfiltered product to produce a pasteurized MIMO product.

11) The method of statement 1-9 or 10 comprising:
 a. providing a fermentation broth comprising maltosyl-isomaltooligosaccharides, dextransucrase/alternansucrase-producing microorganisms, and culture media;
 b. removing the microorganisms from the fermentation broth to produce a cell-free fermentation broth;
 c. optionally passing the cell-free fermentation broth through a carbon filter to produce a first carbon-filtered product;
 d. passing the cell-free fermentation broth or the first carbon-filtered product through at least 200 dalton to 700 dalton molecular weight cut-off nanofiltration unit to produce a first nanofiltered product;
 e. optionally passing the first carbon-filtered product or the first nanofiltered product through a carbon filter to produce a second carbon-filtered product;
 f. passing the first carbon-filtered product, the first nanofiltered product, the second carbon-filtered product, or a combination thereof through a strong acid cation ion exchange resin to produce a first ion exchange treated product;
 g. passing the first ion exchange treated product, the first carbon-filtered product, the first nanofiltered product, the second carbon-filtered product, or a combination thereof through a weak base anion ion exchange resin to produce a second ion exchange treated product;
 h. adjusting the second ion exchange treated product pH, the first ion exchange treated product pH, the first carbon-filtered product pH, the first nanofiltered product pH, the second carbon-filtered product pH, or a combination thereof to a pH less than 5.5, or less than 5.3, or less than 5.0, or less than 4.8, or less than 4.7, or less than 4.6, or less than 4.5, or less than 4.4, or less than 4.3, or less than 4.1, or less than 4.0, or less than 3.9, or less than 3.5, or less than 3.2, or less than 3.0, or less than 2.9, or less than 2.8, or less than 2.7, or less than 2.6, or less than 2.5, or less than 2.4, or less than 2.3 to produce a pH adjusted product;
 i. concentrating the pH adjusted product produce a concentrated MIMO product;
 j. filtering the concentrated MIMO product through a microfilter to produce a microfiltered MIMO product; and
 i. pasteurizing the microfiltered MIMO product to produce a pasteurized MIMO product.

12) The method of statement 11, wherein the cell-free fermentation broth is passed through a carbon filter to produce a carbon filtered product that is then passed through at least one 200 dalton to 700 dalton molecular weight cut-off nanofiltration unit to produce a carbon filtered and nanofiltered product.

13) The method of statement 1-11 or 12, wherein the dextransucrase-producing microorganism is *Leuconostoc* spp (specifically *mesenteroides, citreum, gasicomitatum, carnosum, gelidum, inhae,* and *kimchi*), *Weissella* spp (specifically *confusa, kimchi*), *Lactococcus* spp., *Streptococcus* spp. (specifically *mutans*), *Lactobacillus* spp. (e.g. *reuteri*), *Pediococcus* spp. (specifically *pentosaceus*), and certain mutant *E. coli*.

14) The method of statement 1-12 or 13, wherein the dextransucrase-producing microorganism is *Leuconostoc mesenteroides, Leuconostoc citreum, Leuconostoc gasicomitatum,* or *Leuconostoc kimchii.*

15) The method of statement 1-13, or 14, wherein the dextransucrase-producing microorganism is *Leuconostoc mesenteroides* ATCC 13146.

16) The method of statement 1-14 or 15, wherein the culture media comprises mannitol, organic acids, salts, glycerol, or combinations thereof.

17) The method of statement 1-15 or 16, wherein the culture media comprises one or more of the following organic acids: lactic acid, propionic acid, acetic acid, or formic acid.

18) The method of statement 1-16 or 17, where the fermentation broth was generated from a fermentation reaction comprising fermenting one or more sugars selected from glucose, sucrose, maltose, or a combination thereof.

19) The method of statement 1-17 or 18, where the fermentation broth was generated from a fermentation reaction comprising sucrose and maltose with a ratio of sucrose to maltose ranging from about 2.0 to about 4.5, or about 2.1 to about 4.0, or about 2.2 to about 3.5, or about 2.3 to about 3.0, or about 2.5 to about 3.0, or about 2.5 to about 2.9, or about 2.5 to about 2.8, or about 2.75 at the time of inoculation of the dextransucrase/alternansucrase-producing microorganisms.

20) The method of statement 1-18 or 19, where the fermentation broth was generated from a fermentation reaction comprising sucrose and maltose with a ratio of sucrose to maltose ranging from about 2.5 to about 3.5, or about 2.75.

21) The method of statement 1-19 or 20, wherein step a is operably connected to step b, step b is operably connected to step c, step c is operably connected to step d, step d is operably connected to step e, step e is operably connected to step f, step f is operably connected to step g, step g is operably connected to step h, step h is operably connected to step i, or a combination thereof.

22) The method of statement 1-20 or 21, which is continuous.

23) The method of statement 1-21 or 22, wherein removing the microorganisms from the fermentation broth comprises filtering the fermentation broth, sedimenting cells from the fermentation broth, centrifuging the fermentation broth, or a combination thereof.

24) The method of statement 1-22 or 23, wherein removing the microorganisms from the fermentation broth comprises centrifuging the fermentation broth at about 10,000 g to 15,000 g, or at about 13,000 g to about 14,000 g.

25) The method of statement 1-23 or 24, wherein removing the microorganisms from the fermentation broth comprises filtering the fermentation broth through at least one microfilter comprising a 0.1 µm to 0.4 µm pose size.

26) The method of statement 1-24 or 25, wherein passing the cell-free fermentation broth or the carbon filtered broth through at least one 200 dalton to 700 dalton molecular weight cut-off nanofiltration unit comprises passing the cell-free fermentation broth or the carbon filtered broth through at least one 500 daltons nanofiltration unit.

27) The method of statement 1-25 or 26, wherein passing the cell-free fermentation broth or the carbon filtered broth through at least one 200 daltons to 700 daltons molecular weight cut-off nanofiltration unit comprises passing the cell-free fermentation broth or the carbon filtered through at least one nanofiltration unit comprising 1 to 10 filtration membranes.

28) The method of statement 1-26 or 27, wherein the strong acid cation ion exchange resin is an exchange resin with sulfonic acid groups.

29) The method of statement 1-27 or 28, wherein passing the nanofiltered product through a strong acid cation ion exchange resin removes metal ions.

30) The method of statement 1-28 or 29, wherein the weak base anion ion exchange resin comprises tertiary amine groups.

31) The method of statement 1-29 or 30, wherein passing the first ion exchange treated product through a weak base anion ion exchange resin removes organic acids.

32) The method of statement 1-30 or 31, wherein adjusting the second ion exchange treated product pH comprises adjusting the pH to less than 5.4, or less than 5.3, or less than 5.0, or less than 4.8, or less than 4.6, or less than 4.5, or less than 4.4, or less than 4.3, or less than 4.1, or less than 4.0, or less than 3.9.

33) The method of statement 1-31 or 32, wherein adjusting the second ion exchange treated product pH comprises adjusting the pH to less than 4.6.

34) The method of statement 1-32 or 33, wherein filtering the pH adjusted product through a microfilter comprises filtering the pH adjusted product through at least one microfilter with a molecular weight cut-off of 0.1 µm to 0.5 µm.

35) The method of statement 1-33 or 34, wherein concentrating the pH adjusted product produce a concentrated MIMO product comprises evaporating solvent (e.g., water) from the pH adjusted product.

36) The method of statement 1-34 or 35, wherein filtering the concentrated MIMO product through a microfilter comprises filtering the concentrated MIMO product through at least one microfilter with a molecular weight cut-off of 0.1 µm to 0.5 µm.

37) The method of statement 1-35 or 36, wherein filtering the concentrated MIMO product through a microfilter comprises filtering the concentrated MIMO product through at least one microfilter with a molecular weight cut-off of 0.3 µm and through at least one microfilter with a molecular weight cut-off of 0.2 µm.

38) The method of statement 1-36 or 37, wherein pasteurizing the microfiltered product comprising heating the microfiltered product to about 55° C. to 80° C. for about 15 minutes to about 60 minutes.

39) The method of statement 1-37 or 38, wherein pasteurizing the microfiltered product comprising heating the microfiltered product to about 70° C. for about 30 minutes.

40) The method of statement 1-38 or 39, comprising:
  a. generating a culture medium comprising a sucrose to maltose ratio (S/M) of more than 2.5, more than 2.6, more than 2.7, more than 2.8, or more than 2.9;
  b. initiating a fermentation reaction within the culture medium by adding 5% to 15% w/w dextransucrase/alternansucrase-producing microorganisms to the culture medium;
  c. conducting fermentation within the culture medium for 16-24 hours to generate a fermentation broth;
  d. removing the microorganisms from the fermentation broth by passing the fermentation broth through at least one 0.2 µm microfilter to produce a cell-free fermentation broth;
  e. passing the cell-free fermentation broth through a 500 Da molecular weight cut-off nanofiltration system to produce a nanofiltered product;
  f. passing the nanofiltered product through strong acid cation ion exchange resin to produce a first ion exchange treated product;
  g. passing the first ion exchange treated product through a weak base anion ion exchange resin to produce a second ion exchange treated product;
  h. adjusting the second ion exchange treated product pH to a pH less than 4.6 to produce a pH adjusted product;
  i. filtering the pH adjusted product through at least one microfilter with a molecular weight cut-off of 0.3 µm and through at least one microfilter with a molecular weight cut-off of 0.2 µm.;
  j. concentrating the microfiltered product to produce a concentrated MIMO product; and
  k. pasteurizing the concentrated MIMO product to produce a pasteurized MIMO product.

41) The method of statement 40, wherein the cell-free fermentation broth is passed through a carbon filter to produce a carbon filtered product that is then passed through at least one 200 dalton to 700 dalton molecular weight cut-off nanofiltration unit to produce a carbon filtered and nanofiltered product.

42) The method of statement 40, further comprising passing nanofiltered product through a carbon filter to provide a nanofiltered and carbon filtered product.

43) The method of statement 41 or 42, further comprising passing the nanofiltered and carbon filtered product through a strong acid cation ion exchange resin to produce a first ion exchange treated product.

44) The method of statement 1-42 or 43, further comprising packaging the pasteurized MIMO product.

45) The method of statement 1-43 or 44, wherein the fermentation broth is generated in a fermentation reaction initiated by introduction of a 5%-15% w/w inoculum of the dextransucrase-producing microorganism and the fermentation reaction proceeds for 15-25 hours.

46) The method of statement 1-44 or 45, wherein the fermentation broth is generated in a fermentation reaction initiated by introduction of a 10% w/w inoculum of the dextransucrase-producing microorganism.

47) The method of statement 1-45 or 46, wherein the fermentation broth is generated in a fermentation reaction that proceeds for 16-25 hours.

48) The method of statement 1-46 or 47, wherein the fermentation broth is generated in a fermentation reaction that proceeds for 17-25 hours.

49) The method of statement 1-47 or 48, wherein the fermentation broth is generated in a fermentation reaction that proceeds for 16-18 hours.

50) The method of statement 1-48 or 49, wherein the fermentation broth is generated in a fermentation reaction that proceeds for 22-25 hours.

51) The method of statement 1-49 or 50, wherein the fermentation broth is generated in a fermentation reaction, which at the time of initiation (i.e., at the time of addition of an inoculum of the dextransucrase-producing microorganism) has a sucrose to maltose ratio (S/M) that is more than 2.5, more than 2.6, more than 2.7, more than 2.8, or more than 2.9.

52) The method of statement 1-50 or 51, wherein the fermentation broth is generated in a fermentation reaction, which at the time of initiation (i.e., at the time of addition of an inoculum of the dextransucrase-producing microorganism) has a sucrose to maltose ratio (S/M) that is about 2.90 to 2.92.

53) A manufacturing system comprising:
   a. a first microfilter unit comprising at least one microfilter comprising a molecular weight cut-off of 0.1 µm to 0.4 µm;
   b. a nanofilter unit comprising at least one nanofilter comprising a molecular weight cut-off of 300 daltons to 700 daltons;
   c. a strong acid cation ion exchange resin unit;
   d. a weak base anion ion exchange resin unit;
   e. a pH adjustment unit;
   f. a liquid concentration unit;
   g. a second microfiltration unit comprising at least one microfilter with a molecular weight cut-off of 0.1 µm to 0.4 µm;
   h. a pasteurization unit; or
   a combination thereof 54) The manufacturing system of statement 53, wherein the first microfilter unit of step a is operably connected to the nanofilter unit of step b, the nanofilter unit of step b is operably connected to the strong acid cation ion exchange resin unit of step c, the strong acid cation ion exchange resin unit of step c is operably connected to the weak base anion ion exchange resin unit of step d, the weak base anion ion exchange resin unit of step d is operably connected to the pH adjustment unit of step e, the pH adjustment unit of step e is operably connected to the liquid concentration unit of step f, the liquid concentration unit of step f is operably connected to the second microfiltration unit of step g, the second microfiltration unit of step g is operably connected to the pasteurization unit of step h, the pasteurization unit of step h is operably connected to a packaging unit (step i), or a combination thereof.

55) The manufacturing system of statement 53 or 54, wherein the first microfilter unit removes microorganisms from a fermentation broth.

56) The manufacturing system of statement 53, 54 or 55, wherein the first microfilter unit comprises at least one microfilter comprising a molecular weight cut-off of 0.1 µm to 0.4 µm.

57) The manufacturing system of statement 53-55 or 56, wherein the nanofilter unit comprises at least one nanofilter membrane.

58) The manufacturing system of statement 53-56 or 57, wherein the nanofilter unit comprises 1 to 10 nanofilters, or 2 to 9 nanofilters, or 3 to 9 nanofilters.

59) The manufacturing system of statement 53-57 or 58, wherein the nanofilter unit comprises single tube, or a module containing 15-20 tubes.

60) The manufacturing system of statement 53-58 or 59, wherein the nanofilter unit comprises or a unit containing several filtration modules.

61) The manufacturing system of statement 53-59 or 60, wherein the nanofilter unit comprises at least one membrane with a molecular weight cut-off of 200 to 700 daltons.

62) The manufacturing system of statement 53-60 or 61, wherein the nanofilter unit comprises at least one membrane with a molecular weight cut-off of 450-500 daltons.

63) The manufacturing system of statement 53-61 or 62, wherein the strong acid cation ion exchange resin unit comprises an exchange resin with sulfonic acid groups.

64) The manufacturing system of statement 53-62 or 63, wherein strong acid cation ion exchange resin removes metal ions.

65) The manufacturing system of statement 53-63 or 64, wherein the weak base anion ion exchange resin comprises tertiary amine groups.

66) The manufacturing system of statement 53-64 or 65, wherein the weak base anion ion exchange resin removes organic acids.

67) The manufacturing system of statement 53-65 or 66, wherein pH adjustment unit adjusts the pH of a liquid to less than 5.4, or less than 5.3, or less than 5.0, or less than 4.8, or less than 4.6, or less than 4.5, or less than 4.4, or less than 4.3, or less than 4.1, or less than 4.0, or less than 3.9.

68) The manufacturing system of statement 53-66 or 67, wherein pH adjustment unit adjusts the pH of a liquid to less than 4.6.

69) The manufacturing system of statement 53-67 or 68, wherein the second microfiltration unit comprises at least one microfilter with a molecular weight cut-off of 0.1 µm to 0.5 µm.

70) The manufacturing system of statement 53-68 or 69, wherein the second microfiltration unit comprises at least one microfilter with a molecular weight cut-off of 0.2 µm to 0.5 µm and at least one microfilter with a molecular weight cut-off of 0.1 µm to 0.4 µm.

71) The manufacturing system of statement 53-69 or 70, wherein the second microfiltration unit comprises at least one microfilter with a molecular weight cut-off of 0.3 µm and at least one microfilter with a molecular weight cut-off of 0.2 µm.

72) The manufacturing system of statement 53-70 or 71, wherein the concentration unit comprises an evaporator.

73) The manufacturing system of statement 53-71 or 72, wherein the concentration unit comprises an evaporator that can remove solvent (e.g., water).

74) The manufacturing system of statement 53-72 or 73, wherein the concentration unit heats liquid to about 55° C. to 80° C. for about 15 minutes to about 60 minutes.

75) The manufacturing system of statement 53-73 or 74, wherein the concentration unit heats liquid to about 70° C. for about 30 minutes.

76) The manufacturing system of statement 53-74 or 75, further comprising a packaging unit.

77) The manufacturing system of statement 53-75 or 76, further comprising a fermentation vessel.

78) The manufacturing system of statement 53-76 or 77, further comprising a fermentation vessel operably linked to a purification system comprising:
   a. a first microfilter unit comprising at least one microfilter comprising a molecular weight cut-off of 0.1 µm to 0.4 µm;
   b. a nanofilter unit comprising at least one nanofilter comprising a molecular weight cut-off of 300 daltons to 700 daltons;
   c. a strong acid cation ion exchange resin unit;
   d. a weak base anion ion exchange resin unit;
   e. a pH adjustment unit;
   f. a liquid concentration unit;
   g. a second microfiltration unit comprising at least one microfilter with a molecular weight cut-off of 0.1 µm to 0.4 µm;
   h. a pasteurization unit; or a combination thereof.

79) A fermentation broth comprising: (a) broth components; (b) a mixture of oligosaccharides having a mass average molecular weight distribution (MWD) of 760-780 Da, each oligosaccharide comprising 3 to 9 glucose subunits linked by α-(1-6) glucosyl linkages and terminated with a maltose subunit linked to the terminal glucose subunit by an α-(1→4) glucosyl linkage; and (c) fructose and mannitol in a ratio of about 1.69:1 or about 20.4:12.1%/brix.

The specific methods and systems described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications can be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound" or "an oligosaccharide" or "a maltose" includes a plurality of such compounds, oligosaccharides, or maltose sugars, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed is:

1. A method, comprising:
   (a) providing a production fermentation comprising a mixture for culturing a dextransucrase/alternansucrase-producing microorganism;
   (b) generating a seed inoculum comprising the microorganism in a culture media containing a sucrose to maltose weight ratio (S/M) of more than 2.7;
   (c) initiating a fermentation reaction within the production fermentation by adding the seed inoculum at a 5% to 15% w/w inoculation to obtain log-growth phase of the microorganism in the production fermentation;
   (d) removing the microorganism from the fermentation broth to provide a cell-free fermentation broth comprising maltosyl-isomaltooligosaccharides ("MIMOs"); and
   (e) passing the cell-free fermentation broth through a nanofiltration unit selected from at least one membrane having a molecular weight cut-off of 450-500 Da to produce a nanofiltered product.

2. The method of claim 1, further comprising passing the cell-free fermentation broth before the nanofiltration or the nanofiltered product in step (e) through a strong acid cation ion exchange resin, a weak anion ion exchange resin, or both to respectively produce ion exchange treated products.

3. The method of claim 2, further comprising adjusting pH of the ion exchange treated product to a pH less than 5.5 thereby producing a pH adjusted product.

4. The method of claim 3, further comprising concentrating the pH adjusted product to produce a concentrated MIMO product.

5. The method of claim 4, further comprising filtering the concentrated MIMO product through a microfilter to produce a microfiltered MEM product.

6. The method of claim 5, further comprising pasteurizing the microfiltered MIMO product to produce a pasteurized MIMO product.

7. The method of claim 5, further comprising filtering one or more of the nanofiltered product, ion exchange treated product, pH adjusted product, concentrated MIMO product, or microfiltered MIMO product through a carbon filter.

8. The method of claim 1, further comprising:
(a) concentrating the nanofiltered product to produce a concentrated nanofiltered product,
(b) optionally adjusting the pH of the nanofiltered product to produce a pH adjusted concentrated nanofiltered product,
(c) optionally filtering the concentrated nanofiltered product or the pH adjusted concentrated nanofiltered product through a carbon filter to produce respective carbon filtered nanofiltered products,
(d) optionally filtering the concentrated nanofiltered product, the pH adjusted concentrated nanofiltered product, or the carbon filtered nanofiltered product through a microfilter to produce respective microfiltered nanofiltered products, and
e) pasteurizing the concentrated nanofiltered product or the microfiltered nanofiltered product to produce respective pasteurized nanofiltered products.

9. The method of claim 2, further comprising:
(a) concentrating the ion exchange treated product to produce a concentrated ion exchange treated product,
(b) optionally adjusting the pH of the concentrated ion exchange treated product to produce a pH adjusted concentrated ion exchange treated product,
(c) optionally filtering the concentrated ion exchange treated product before the pH adjusting or the pH adjusted concentrated ion exchange treated product through a carbon filter to produce respective carbon filtered ion exchange treated products,
(d)optionally filtering the concentrated ion exchange treated product, the pH adjusted concentrated ion exchange treated product before the carbon filtering or the carbon filtered ion exchange treated product through respective microfilter to produce a microfiltered ion exchange treated products, and
(e) pasteurizing the concentrated ion exchange treated product or the microfiltered ion exchange treated product to produce a pasteurized concentrated or microfiltered ion exchange treated product.

10. The method of claim 1, wherein the method comprises:
in step (e) passing the cell-free fermentation broth a first carbon-filtered product through at least one 500-dalton molecular weight cut-off nanofiltration unit to produce respective first nanofiltered products, wherein the first carbon-filtered product is produced by passing the cell-free fermentation broth through a carbon filter; and optionally further passing
the first carbon-filtered product or the respective first nanofiltered products through a second carbon filter to produce respective second carbon-filtered products; passing
the first carbon-filtered product, the respective first nanofiltered product, the respective second carbon-filtered product, or a combination thereof through one or more of a strong acid cation ion exchange resin or a weak base anion ion exchange resin to produce a respective ion exchange treated products; passing the respective ion exchange treated products through a third carbon filter to produce respective third carbon-filtered products; adjusting the respective ion exchange treated products, or the respective third carbon-filtered products to respective pH adjusted products; concentrating the respective pH adjusted products to produce respective concentrated MIMO products; filtering the respective concentrated MI MO products through a microfilter to produce respective microfiltered MIMO products; and pasteurizing the respective microfiltered MIMO products to produce respective pasteurized MI MO products.

11. The method of claim 1, wherein the microorganism is *Leuconostoc* spp., *Weissella* spp., *Lactococcus* spp., *Streptococcus* spp., *Lactobacillus* spp., or *Pediococcus*,spp.

12. The method of claim 1, wherein the microorganism is *Leuconostoc mesenteroides, Leuconostoc citreum, Leuconostoc gasicomitatum Leuconostoc kimchii*, Weissella confusa, *Pediococcus pentosaceus, Leuconostoc amelibiosum, Lactobacillus sanfranciscensis*, or a combination thereof.

13. The method of claim 1, wherein the microorganism is *Leuconostoc mesenteroides* ATCC 13146.

14. The method of claim 1, wherein removing the microorganism from the fermentation broth comprises filtering the fermentation broth, sedimenting microorganismal cells from the fermentation broth, centrifuging the fermentation broth, or a combination thereof.

15. The method of claim 1, wherein the step (e) comprises passing the cell-free fermentation broth through at least one 500 daltons nanofiltration unit.

16. The method of claim 10, wherein the step (e) comprises passing the cell-free fermentation broth or the first carbon filtered product through at least one nanofiltration unit comprising 1 to 10 filtration membranes.

17. The method of claim 5, wherein pH adjusted product is passed one or more times through at least one microfilter with a molecular weight cut-off of 0.5 microns to 5 microns.

18. The method of claim 6, wherein pasteurizing the microfiltered product comprising heating the microfiltered product to about 55° C. to 80° C. for about 15 minutes to about 60 minutes.

19. The method of claim 1, further comprising packaging the r a ° filtered product to produce a packaged product.

20. The method of claim 1, wherein the sucrose to maltose weight ratio (S/M) of about 2.90 to 2.92.

21. The method of claim 1, wherein generating the seed inoculum takes 10-24 hours.

22. The method of claim 1, wherein the fermentation reaction takes 10-24 hours.

23. The method of claim 1, wherein the microorganism is a dextransucrase- or an alternansucrase-producing microorganism.

* * * * *